(12) United States Patent
Davis

(10) Patent No.: US 7,417,039 B2
(45) Date of Patent: Aug. 26, 2008

(54) USE OF SUBSTITUTED AZETIDINONE COMPOUNDS FOR THE TREATMENT OF SITOSTEROLEMIA

(75) Inventor: Harry R. Davis, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 1159 days.

(21) Appl. No.: 10/057,629

(22) Filed: Jan. 25, 2002

(65) Prior Publication Data

US 2002/0169134 A1  Nov. 14, 2002

Related U.S. Application Data

(60) Provisional application No. 60/264,645, filed on Jan. 26, 2001.

(51) Int. Cl.
*A61K 31/33* (2006.01)
*A61K 31/35* (2006.01)

(52) U.S. Cl. ........................................ 514/183; 514/451

(58) Field of Classification Search ................ 514/183, 514/461, 451
See application file for complete search history.

(56) References Cited

U.S. PATENT DOCUMENTS

| | | | |
|---|---|---|---|
| 2,809,194 A | 10/1957 | Novello |
| 3,108,097 A | 10/1963 | Ugi |
| 3,152,173 A | 10/1964 | Ehrhart |
| 3,267,104 A | 8/1966 | Hermans |
| 3,399,192 A | 8/1968 | Regnier |
| 3,692,895 A | 9/1972 | Nelson |
| 3,716,583 A | 2/1973 | Nakamura |
| 3,781,328 A | 12/1973 | Witte |
| 3,948,973 A | 4/1976 | Phillips |
| 4,072,705 A | 2/1978 | Mieville |
| 4,075,000 A | 2/1978 | Abdulla |
| 4,144,232 A | 3/1979 | Koppel |
| 4,148,923 A | 4/1979 | Giudicelli |
| 4,166,907 A | 9/1979 | Krapcho |
| 4,178,695 A | 12/1979 | Erbeia |
| 4,179,515 A | 12/1979 | Mieville |
| 4,235,896 A | 11/1980 | Mieville |
| 4,239,763 A | 12/1980 | Milavec |
| 4,250,191 A | 2/1981 | Edwards |
| 4,260,743 A | 4/1981 | Bose |
| 4,304,718 A | 12/1981 | Kamiya |
| 4,375,475 A | 3/1983 | Willard |
| 4,443,372 A | 4/1984 | Luo |
| 4,444,784 A | 4/1984 | Hoffman |
| 4,472,309 A | 9/1984 | Kamiya |
| 4,479,900 A | 10/1984 | Luo |
| 4,500,456 A | 2/1985 | Spitzer |
| 4,534,786 A | 8/1985 | Luo |
| 4,564,609 A | 1/1986 | Tamura |
| 4,567,195 A | 1/1986 | Schwarz |
| 4,576,748 A | 3/1986 | Greenlee |
| 4,576,749 A | 3/1986 | Zahler |
| 4,576,753 A | 3/1986 | Kamiya |
| 4,581,170 A | 4/1986 | Mueller |
| 4,595,532 A | 6/1986 | Miller |
| 4,602,003 A | 7/1986 | Malinow |
| 4,602,005 A | 7/1986 | Malinow |
| 4,614,614 A | 9/1986 | Ernest |
| 4,616,047 A | 10/1986 | Lafon |
| 4,620,867 A | 11/1986 | Luo |
| 4,626,549 A | 12/1986 | Molloy |
| 4,633,017 A | 12/1986 | Mueller |
| 4,642,903 A | 2/1987 | Davies |
| 4,654,362 A | 3/1987 | Lommen |
| 4,675,399 A | 6/1987 | Miller |
| 4,680,289 A | 7/1987 | Applezweig |
| 4,680,391 A | 7/1987 | Firestone |
| 4,687,777 A | 8/1987 | Meguro et al. |
| 4,739,101 A | 4/1988 | Bourgogne |
| 4,778,883 A | 10/1988 | Yoshioka |
| 4,784,734 A | 11/1988 | Torii |
| 4,794,108 A | 12/1988 | Kishimoto |
| 4,800,079 A | 1/1989 | Boyer |
| 4,803,266 A | 2/1989 | Kawashima |
| 4,814,354 A | 3/1989 | Ghebre-Sellassie |
| 4,834,846 A | 5/1989 | Abramson |
| 4,871,752 A | 10/1989 | Ilg et al. |
| 4,876,365 A | 10/1989 | Kirkup |
| 4,879,301 A | 11/1989 | Umio |

(Continued)

FOREIGN PATENT DOCUMENTS

BE  884722 A  12/1980

(Continued)

OTHER PUBLICATIONS

Berge et al., Seience, 2000; 290:1771-1775.*

(Continued)

*Primary Examiner*—San-ming Hui
(74) *Attorney, Agent, or Firm*—Mark W. Russell

(57) ABSTRACT

The present invention is directed to the use of sterol absorption inhibiting compounds, pharmaceutical compositions thereof, therapeutic combinations and their use in combination with other lipid lowering agents to treat or prevent sitosterolemia and/or to lower the concentration of sterol(s) other than cholesterol in plasma or tissue of a mammal. Methods of treating or preventing vascular disease and coronary events also are provided.

53 Claims, No Drawings

U.S. PATENT DOCUMENTS

| | | | |
|---|---|---|---|
| 4,895,726 A | 1/1990 | Curtet |
| 4,925,672 A | 5/1990 | Gremm |
| 4,937,267 A | 6/1990 | Holloway |
| 4,939,248 A | 7/1990 | Yoshioka |
| 4,952,689 A | 8/1990 | Kawashima |
| 4,961,890 A | 10/1990 | Boyer |
| 4,983,597 A | 1/1991 | Yang |
| 4,990,535 A | 2/1991 | Cho |
| 5,021,461 A | 6/1991 | Robinson et al. |
| 5,030,628 A | 7/1991 | Joyeau |
| 5,073,374 A | 12/1991 | McCarty |
| 5,091,525 A | 2/1992 | Brennan |
| 5,093,365 A | 3/1992 | Berge |
| 5,099,034 A | 3/1992 | Yoshida |
| 5,100,675 A | 3/1992 | Cho |
| 5,106,833 A | 4/1992 | Broze |
| 5,110,730 A | 5/1992 | Edgington |
| 5,112,616 A | 5/1992 | McCarty |
| 5,120,713 A | 6/1992 | Mugica |
| 5,120,729 A | 6/1992 | Chabala |
| 5,130,333 A | 7/1992 | Pan |
| 5,145,684 A | 9/1992 | Liversidge |
| 5,157,025 A | 10/1992 | Aberg |
| 5,162,117 A | 11/1992 | Stupak |
| 5,178,878 A | 1/1993 | Wehling |
| 5,188,825 A | 2/1993 | Iles |
| 5,190,970 A | 3/1993 | Pan |
| 5,204,461 A | 4/1993 | Murayama |
| 5,219,574 A | 6/1993 | Wehling |
| 5,223,264 A | 6/1993 | Wehling |
| 5,229,362 A | 7/1993 | Kirst |
| 5,229,381 A | 7/1993 | Doherty |
| 5,229,510 A | 7/1993 | Knight |
| 5,260,305 A | 11/1993 | Dennick |
| 5,278,176 A | 1/1994 | Lin |
| H1286 H | 2/1994 | Eisman |
| 5,286,631 A | 2/1994 | Boeck |
| 5,298,497 A | 3/1994 | Tschollar |
| 5,306,817 A | 4/1994 | Thiruvengadam |
| 5,318,767 A | 6/1994 | Liversidge |
| 5,348,953 A | 9/1994 | Doherty |
| 5,350,868 A | 9/1994 | Yoshida |
| 5,358,852 A | 10/1994 | Wu |
| 5,384,124 A | 1/1995 | Courteille |
| 5,385,885 A | 1/1995 | Gasic |
| 5,399,363 A | 3/1995 | Liversidge |
| 5,401,513 A | 3/1995 | Wehling |
| 5,412,092 A | 5/1995 | Rey |
| 5,429,824 A | 7/1995 | June |
| 5,446,464 A | 8/1995 | Feldle |
| 5,461,039 A | 10/1995 | Tschollar |
| 5,464,632 A | 11/1995 | Cousin |
| 5,494,683 A | 2/1996 | Liversidge |
| 5,503,846 A | 4/1996 | Wehling |
| 5,510,118 A | 4/1996 | Bosch |
| 5,510,466 A | 4/1996 | Krieger |
| 5,518,187 A | 5/1996 | Bruno |
| 5,518,738 A | 5/1996 | Eickhoff |
| 5,545,628 A | 8/1996 | Deboeck |
| 5,550,229 A | 8/1996 | Iwasaki |
| 5,552,160 A | 9/1996 | Liversidge |
| 5,561,227 A | 10/1996 | Thiruvengadam |
| 5,563,264 A | 10/1996 | Kume |
| 5,567,439 A | 10/1996 | Myers |
| 5,576,014 A | 11/1996 | Mizumoto |
| 5,587,172 A | 12/1996 | Cherukuri |
| 5,587,180 A | 12/1996 | Allen |
| 5,591,456 A | 1/1997 | Franson |
| 5,593,971 A | 1/1997 | Tschollar |
| 5,595,761 A | 1/1997 | Allen |
| 5,607,697 A | 3/1997 | Alkire |
| 5,612,353 A | 3/1997 | Ewing |
| 5,612,367 A | 3/1997 | Timko |
| 5,612,378 A | 3/1997 | Tianbao |
| 5,618,707 A | 4/1997 | Homann |
| 5,622,719 A | 4/1997 | Myers |
| 5,622,985 A | 4/1997 | Olukotun |
| 5,624,920 A | 4/1997 | McKittrick |
| 5,627,176 A | 5/1997 | Kirkup |
| 5,631,023 A | 5/1997 | Kearney |
| 5,631,365 A | 5/1997 | Rosenblum |
| 5,633,246 A | 5/1997 | McKittrick |
| 5,635,210 A | 6/1997 | Allen |
| 5,639,475 A | 6/1997 | Bettman |
| 5,639,739 A | 6/1997 | Dominguez |
| 5,656,624 A | 8/1997 | Vaccaro |
| 5,661,145 A | 8/1997 | Davis |
| 5,674,893 A | 10/1997 | Behounek |
| 5,688,785 A | 11/1997 | Vaccaro |
| 5,688,787 A | 11/1997 | Burnett |
| 5,688,990 A | 11/1997 | Shankar |
| 5,691,375 A | 11/1997 | Behounek |
| 5,698,527 A | 12/1997 | Kim |
| 5,698,548 A | 12/1997 | Dugar |
| 5,703,188 A | 12/1997 | Mandeville |
| 5,703,234 A | 12/1997 | Iwasaki |
| 5,709,886 A | 1/1998 | Bettman |
| 5,718,388 A | 2/1998 | Czekai |
| 5,728,827 A | 3/1998 | Thiruvengadam et al. |
| 5,734,077 A | 3/1998 | Regnier |
| 5,739,321 A | 4/1998 | Wu |
| 5,744,467 A | 4/1998 | McKittrick |
| 5,747,001 A | 5/1998 | Wiedmann |
| 5,753,254 A | 5/1998 | Khan |
| 5,756,470 A | 5/1998 | Yumibe |
| 5,759,865 A | 6/1998 | Bruns |
| 5,767,115 A * | 6/1998 | Rosenblum et al. ..... 514/210.02 |
| 5,776,491 A | 7/1998 | Allen |
| 5,807,576 A | 9/1998 | Allen |
| 5,807,577 A | 9/1998 | Ouali |
| 5,807,578 A | 9/1998 | Acosta-Cuello |
| 5,807,834 A | 9/1998 | Morehouse |
| 5,808,056 A | 9/1998 | Amato |
| 5,817,806 A | 10/1998 | Rossi |
| 5,827,536 A | 10/1998 | Laruelle |
| 5,827,541 A | 10/1998 | Yarwood |
| 5,831,091 A | 11/1998 | Ohmizu |
| 5,843,984 A | 12/1998 | Clay |
| 5,846,966 A * | 12/1998 | Rosenblum et al. ..... 514/210.02 |
| 5,847,008 A | 12/1998 | Doebber |
| 5,847,115 A | 12/1998 | Iwasaki |
| 5,851,553 A | 12/1998 | Myers |
| 5,856,473 A | 1/1999 | Shankar |
| 5,858,409 A | 1/1999 | Karetny |
| 5,859,051 A | 1/1999 | Adams |
| 5,862,999 A | 1/1999 | Czekai |
| 5,866,163 A | 2/1999 | Myers |
| 5,869,098 A | 2/1999 | Misra |
| 5,871,781 A | 2/1999 | Myers |
| 5,880,148 A | 3/1999 | Edgar |
| 5,883,109 A | 3/1999 | Gregg |
| 5,886,171 A | 3/1999 | Wu |
| 5,919,672 A | 7/1999 | Homann |
| 5,925,333 A | 7/1999 | Krieger |
| 5,952,003 A | 9/1999 | Guentensberger |
| 5,952,321 A | 9/1999 | Doherty |
| 5,959,123 A | 9/1999 | Singh |
| 5,972,389 A | 10/1999 | Shell |
| 5,976,570 A | 11/1999 | Greaves |
| 5,985,936 A | 11/1999 | Novak |
| 5,990,102 A | 11/1999 | Hickey |
| 5,994,554 A | 11/1999 | Kliewer |
| 5,998,441 A | 12/1999 | Palkowitz |
| 6,008,237 A | 12/1999 | Sahoo |

| | | | | | | |
|---|---|---|---|---|---|---|
| 6,027,747 | A | 2/2000 | Terracol | EP | 0010299 B1 | 2/1984 |
| 6,028,109 | A | 2/2000 | Wilson | EP | 0179559 A2 | 4/1986 |
| 6,030,990 | A | 2/2000 | Maeda et al. | EP | 0199630 A1 | 10/1986 |
| 6,033,656 | A | 3/2000 | Mikami | EP | 0264231 A1 | 4/1988 |
| 6,040,147 | A | 3/2000 | Ridker | EP | 0266896 B1 | 5/1988 |
| 6,043,257 | A | 3/2000 | Dominguez | EP | 0274873 B1 | 7/1988 |
| 6,056,975 | A | 5/2000 | Mitra | EP | 0288973 B1 | 11/1988 |
| 6,057,342 | A | 5/2000 | Fevig | EP | 0311366 B1 | 4/1989 |
| 6,063,764 | A | 5/2000 | Creasey | EP | 0333268 A1 | 9/1989 |
| 6,066,653 | A | 5/2000 | Gregg | EP | 0337549 A1 | 10/1989 |
| 6,071,899 | A | 6/2000 | Hickey | EP | 0365364 A2 | 4/1990 |
| 6,074,670 | A | 6/2000 | Stamm | EP | 0369686 A1 | 5/1990 |
| 6,080,767 | A | 6/2000 | Klein | EP | 0375527 A1 | 6/1990 |
| 6,080,778 | A | 6/2000 | Yankner | EP | 0199630 B1 | 9/1990 |
| 6,084,082 | A | 7/2000 | Ravikumar | EP | 0401705 A3 | 12/1990 |
| 6,090,830 | A | 7/2000 | Myers | EP | 0415487 A2 | 3/1991 |
| 6,090,839 | A | 7/2000 | Adams | EP | 0455042 A1 | 11/1991 |
| 6,093,812 | A | 7/2000 | Thiruvengadam | EP | 0457514 A1 | 11/1991 |
| 6,096,883 | A | 8/2000 | Wu | EP | 0461548 A3 | 12/1991 |
| 6,099,865 | A | 8/2000 | Augello | EP | 0462667 A2 | 12/1991 |
| 6,103,705 | A | 8/2000 | Uzan | EP | 0475148 A1 | 3/1992 |
| 6,110,493 | A | 8/2000 | Guentensberger | EP | 0475755 B1 | 3/1992 |
| 6,117,429 | A | 9/2000 | Bucci | EP | 0481671 A1 | 4/1992 |
| 6,121,319 | A | 9/2000 | Somers | EP | 0482498 A3 | 4/1992 |
| 6,127,424 | A | 10/2000 | Martin | EP | 0524595 A1 | 1/1993 |
| 6,133,001 | A | 10/2000 | Homann | EP | 0337549 B1 | 10/1995 |
| 6,139,873 | A | 10/2000 | Hughes | EP | 0720599 B1 | 7/1996 |
| 6,140,354 | A | 10/2000 | Dax | EP | 0457514 B1 | 8/1996 |
| 6,143,885 | A | 11/2000 | Choi | EP | 0 753 298 A1 | 1/1997 |
| 6,147,090 | A | 11/2000 | DeNinno | EP | 0793958 A2 | 9/1997 |
| 6,147,109 | A | 11/2000 | Liao | EP | 0814080 A1 | 12/1997 |
| 6,147,250 | A | 11/2000 | Somers | EP | 0904781 A2 | 3/1999 |
| 6,159,997 | A | 12/2000 | Tsujita | EP | 1 036 563 A1 | 9/2000 |
| 6,162,805 | A | 12/2000 | Hefti | EP | 1048295 A2 | 11/2000 |
| 6,166,049 | A | 12/2000 | Smith | FR | 1103113 | 10/1955 |
| 6,174,665 | B1 | 1/2001 | Dullien | FR | 2779347 | 12/1997 |
| 6,180,138 | B1 | 1/2001 | Engh | GB | 861367 | 2/1961 |
| 6,180,625 | B1 | 1/2001 | Persson | GB | 902658 | 8/1962 |
| 6,180,660 | B1 | 1/2001 | Whitney | GB | 1415295 | 11/1975 |
| 6,191,117 | B1 | 2/2001 | Kozachuk | GB | 2329334 A | 3/1999 |
| 6,191,159 | B1 | 2/2001 | Pinto | JP | 136485 | 5/1981 |
| 6,200,998 | B1 | 3/2001 | Sahoo | JP | 028057 | 10/1981 |
| 6,207,697 | B1 | 3/2001 | Han | JP | 180212 | 3/1986 |
| 6,207,699 | B1 | 3/2001 | Rothman | JP | 121479 | 12/1986 |
| 6,207,822 | B1 | 3/2001 | Thiruvengadam | JP | 61280295 A | 12/1986 |
| 6,214,831 | B1 | 4/2001 | Yokoo | JP | 219681 | 4/1987 |
| 6,235,706 | B1 | 5/2001 | Gould | JP | 63017859 A | 1/1988 |
| 6,242,605 | B1 | 6/2001 | Raveendranath | JP | 91068020 | 10/1991 |
| 6,245,743 | B1 | 6/2001 | Marlowe | JP | 4054182 A | 2/1992 |
| 6,248,781 | B1 | 6/2001 | Jeppesen | JP | 4266869 A | 9/1992 |
| 6,251,852 | B1 | 6/2001 | Gould | JP | 4356195 A | 12/1992 |
| 6,262,042 | B1 | 7/2001 | Cook | JP | 4356495 | 12/1992 |
| 6,262,047 | B1 | 7/2001 | Zhu | JP | 5058993 A | 3/1993 |
| 6,262,098 | B1 | 7/2001 | Huebner | JP | 5194209 A | 8/1993 |
| 6,277,584 | B1 | 8/2001 | Chu | JP | 5239020 A | 9/1993 |
| 6,316,029 | B1 | 11/2001 | Jain | JP | 94047573 | 6/1994 |
| RE37,721 | E | 5/2002 | Rosenblum | JP | 95051558 B2 | 6/1995 |
| 2001/0028895 | A1 | 10/2001 | Bisgaier | WO | WO82/01649 | 5/1982 |
| 2002/0006919 | A1 | 1/2002 | Thosar | WO | WO87/04429 | 7/1987 |
| 2002/0039774 | A1 | 4/2002 | Kramer et al. | WO | WO88/04656 | 6/1988 |
| 2002/0128252 | A1 | 9/2002 | Glombik et al. | WO | WO88/05296 | 7/1988 |
| 2002/0128253 | A1 | 9/2002 | Glombik et al. | WO | WO91/03249 | 3/1991 |
| 2002/0132855 | A1 | 9/2002 | Nelson et al. | WO | WO92/13837 | 8/1992 |
| 2002/0137689 | A1 | 9/2002 | Glombik et al. | WO | WO93/02048 | 2/1993 |
| 2003/0153541 | A1 | 8/2003 | Dudley et al. | WO | WO93/07167 | 4/1993 |
| | | | | WO | WO93/11150 | 6/1993 |
| | | FOREIGN PATENT DOCUMENTS | | WO | WO94/00480 | 1/1994 |
| | | | | WO | WO94/14433 | 7/1994 |
| CA | | 2253769 | 11/1999 | WO | WO94/17038 | 8/1994 |
| DE | | 2046823 A | 3/1972 | WO | WO94/20535 | 9/1994 |
| DE | | 2521113 A | 3/1976 | WO | WO94/26738 | 11/1994 |
| EP | | 0002151 A1 | 5/1979 | WO | WO95/04533 | 2/1995 |
| EP | | 0002151 B1 | 5/1979 | WO | WO95/06470 | 3/1995 |

| | | | | | | |
|---|---|---|---|---|---|---|
| WO | WO95/08532 | 3/1995 | | WO | WO 00/38726 | 7/2000 |
| WO | WO95/18143 | 7/1995 | | WO | WO 00/38727 | 7/2000 |
| WO | WO95/26334 | 10/1995 | | WO | WO 00/38728 | 7/2000 |
| WO | WO95/28919 | 11/1995 | | WO | WO 00/38729 | 7/2000 |
| WO | WO 95/35277 | 12/1995 | | WO | WO 00/40247 | 7/2000 |
| WO | WO96/00288 | 1/1996 | | WO | WO 00/45817 | 8/2000 |
| WO | WO96/09827 | 4/1996 | | WO | WO 00/50392 | 8/2000 |
| WO | WO96/16037 | 5/1996 | | WO | WO 00/53149 | 9/2000 |
| WO | WO96/19450 | 6/1996 | | WO | WO 00/53173 | 9/2000 |
| WO | WO96/19987 | 7/1996 | | WO | WO 00/53563 | 9/2000 |
| WO | WO96/40255 | 12/1996 | | WO | WO 00/56403 | 9/2000 |
| WO | WO97/16455 | 5/1997 | | WO | WO 00/57859 | 10/2000 |
| WO | WO97/18304 | 5/1997 | | WO | WO 00/57918 | 10/2000 |
| WO | WO97/21676 | 6/1997 | | WO | WO 00/60107 | 10/2000 |
| WO | WO97/25042 | 7/1997 | | WO | WO 00/63153 | 10/2000 |
| WO | WO 97/28149 | 8/1997 | | WO | WO 00/63161 | 10/2000 |
| WO | WO97/28149 | 8/1997 | | WO | WO 00/63190 | 10/2000 |
| WO | WO97/31907 | 9/1997 | | WO | WO 00/63196 | 10/2000 |
| WO | WO97/35576 | 10/1997 | | WO | WO 00/63209 | 10/2000 |
| WO | WO97/41098 | 11/1997 | | WO | WO 00/63703 | 10/2000 |
| WO | WO97/46238 | 12/1997 | | WO | WO 00/69412 | 11/2000 |
| WO | WO98/01100 | 1/1998 | | WO | WO 00/69445 | 11/2000 |
| WO | WO98/05331 | 2/1998 | | WO | WO 00/72825 | 12/2000 |
| WO | WO98/14179 | 4/1998 | | WO | WO 00/72829 | 12/2000 |
| WO | WO98/31360 | 7/1998 | | WO | WO 00/75103 | 12/2000 |
| WO | WO98/31361 | 7/1998 | | WO | WO 00/76482 | 12/2000 |
| WO | WO98/31366 | 7/1998 | | WO | WO 00/76488 | 12/2000 |
| WO | WO98/43081 | 10/1998 | | WO | WO 00/78312 | 12/2000 |
| WO | WO98/46215 | 10/1998 | | WO | WO 00/78313 | 12/2000 |
| WO | WO98/47518 | 10/1998 | | WO | WO 01/00579 | 1/2001 |
| WO | WO98/57652 | 12/1998 | | WO | WO 01/00603 | 1/2001 |
| WO | WO99/06035 | 2/1999 | | WO | WO 01/08686 | 2/2001 |
| WO | WO99/06046 | 2/1999 | | WO | WO 01/12176 | 2/2001 |
| WO | WO99/08501 | 2/1999 | | WO | WO 01/12187 | 2/2001 |
| WO | WO99/09967 | 3/1999 | | WO | WO 01/12612 | 2/2001 |
| WO | WO99/11260 | 3/1999 | | WO | WO 01/14349 | 3/2001 |
| WO | WO99/12534 | 3/1999 | | WO | WO 01/14350 | 3/2001 |
| WO | WO99/04815 | 4/1999 | | WO | WO 01/14351 | 3/2001 |
| WO | WO99/15159 | 4/1999 | | WO | WO 01/15744 | 3/2001 |
| WO | WO99/15520 | 4/1999 | | WO | WO 01/16120 | 3/2001 |
| WO | WO99/18072 | 4/1999 | | WO | WO 01/17994 | 3/2001 |
| WO | WO99/20275 | 4/1999 | | WO | WO 01/18210 | 3/2001 |
| WO | WO99/20614 | 4/1999 | | WO | WO 01/21181 | 3/2001 |
| WO | WO99/22728 | 5/1999 | | WO | WO 01/21259 | 3/2001 |
| WO | WO99/29300 | 6/1999 | | WO | WO 01/21578 | 3/2001 |
| WO | WO99/38498 | 8/1999 | | WO | WO 01/21647 | 3/2001 |
| WO | WO99/38845 | 8/1999 | | WO | WO 01/22962 | 4/2001 |
| WO | WO99/38850 | 8/1999 | | WO | WO 01/25225 | 4/2001 |
| WO | WO99/46232 | 9/1999 | | WO | WO 01/25226 | 4/2001 |
| WO | WO99/47123 | 9/1999 | | WO | WO 01/30343 | 5/2001 |
| WO | WO99/48488 | 9/1999 | | WO | WO 01/32161 | 5/2001 |
| WO | WO99/66929 | 12/1999 | | WO | WO 01/34148 | 5/2001 |
| WO | WO99/66930 | 12/1999 | | WO | WO 01/35970 | 5/2001 |
| WO | WO 00/04011 | 1/2000 | | WO | WO 01/40192 | 6/2001 |
| WO | WO 00/07617 | 2/2000 | | WO | WO 01/45676 | 6/2001 |
| WO | WO 00/16749 | 3/2000 | | WO | WO 01/49267 | 7/2001 |
| WO | WO 00/18395 | 4/2000 | | WO | WO 01/60807 | 8/2001 |
| WO | WO 00/23415 | 4/2000 | | WO | WO 01/64221 | 9/2001 |
| WO | WO 00/23416 | 4/2000 | | WO | WO 01/76632 | 10/2001 |
| WO | WO 00/23425 | 4/2000 | | WO | WO 01/96347 | 12/2001 |
| WO | WO 00/23445 | 4/2000 | | WO | WO 02/08188 | 1/2002 |
| WO | WO 00/23451 | 4/2000 | | WO | WO 02/26729 | 4/2002 |
| WO | WO 00/28981 | 5/2000 | | WO | WO 02/50027 | 6/2002 |
| WO | WO 00/31548 | 6/2000 | | WO | WO 02/50060 | 6/2002 |
| WO | WO 00/32189 | 6/2000 | | WO | WO 02/50068 | 6/2002 |
| WO | WO 00/34240 | 6/2000 | | WO | WO 02/50090 | 6/2002 |
| WO | WO 00/37057 | 6/2000 | | WO | WO 02/058685 | 8/2002 |
| WO | WO 00/37078 | 6/2000 | | WO | WO 02/058696 | 8/2002 |
| WO | WO 00/38721 | 7/2000 | | WO | WO 02/058731 | 8/2002 |
| WO | WO 00/38722 | 7/2000 | | WO | WO 02/058732 | 8/2002 |
| WO | WO 00/38723 | 7/2000 | | WO | WO 02/058733 | 8/2002 |
| WO | WO 00/38724 | 7/2000 | | WO | WO 02/058734 | 8/2002 |
| WO | WO 00/38725 | 7/2000 | | WO | WO 02/064094 | 8/2002 |

| | | |
|---|---|---|
| WO | WO 02/064130 | 8/2002 |
| WO | WO 02/064549 | 8/2002 |
| WO | WO 02/064664 | 8/2002 |
| WO | WO 02/072104 | 9/2002 |
| WO | WO 02/081454 | 10/2002 |
| WO | WO 03/018024 | 3/2003 |
| WO | WO 03/018059 | 3/2003 |
| WO | WO 03/039542 | 5/2003 |
| WO | WO 03/074101 | 9/2003 |
| WO | WO 03/088962 | 10/2003 |

OTHER PUBLICATIONS

Hidaka et al., J. Atheroscler. Thromb., 1995;2(1):60-65.*
Belamarich et al., Pediatrics, 1990;86(6):977-981.*
H.R. Casdorph, "Hypercholesteremia: Treatment with Cholestyramine, a Bile Acid Sequestering Resin," California Medicine, vol. 106, pp. 293-295 (1967).*
U.S. Appl. No. 10/057,534, filed Jan. 25, 2002, Harry R. Davis et al.
U.S. Appl. No. 10/057,646, filed Jan. 25, 2002, Harry R. Davis et al.
U.S. Appl. No. 10/057,629, filed Jan. 25, 2002, Harry R. Davis.
U.S. Appl. No. 10/154,106, filed May 22, 2002, Harry R. Davis et al.
U.S. Appl. No. 10/057,323, filed Jan. 25, 2002, Harry R. Davis et al.
U.S. Appl. No. 10/136,968, filed May 1, 2002, Wing-Kee Philip Cho et al.
U.S. Appl. No. 10/057,339, filed Jan. 25, 2002, Teddy Kosoglou et al.
U.S. Appl. No. 10/247,032, filed Jan. 25, 2002, Harry R. Davis.
U.S. Appl. No. 10/056,680, filed Jan. 25, 2002, Teddy Kosoglou et al.
U.S. Appl. No. 10/247,099, filed Sep. 19, 2002, Harry R. Davis et al.
U.S. Appl. No. 10/247,085, filed Sep. 19, 2002, John T. Strony.
U.S. Appl. No. 10/247,095, filed Sep. 19, 2002, Harry R. Davis.
U.S. Appl. No. 10/246,996, filed Sep. 19, 2002, Alexandre P. Lebeaut et al.
U.S. Appl. No. 10/247,397, filed Sep. 19, 2002, Harry R. Davis et al.
U.S. Appl. No. 10/166,942, filed Jun. 11, 2002, Anima Ghosal et al.
Vaccaro, W.D. et al , "Sugar-substituted 2-azetidinone cholesterol absorption inhibitors: enhanced potency by modification of the sugar" Bioorganic & Medicinal Chemistry Ltrs., Oxford, G.B., 8:313-318 (1998).
Vaccaro, W.D. et al., "Carboxy-substituted 2-azetidinones as cholesterol absorption inhibitors", Biorganic & Medicinal Chem. Ltrs. Oxford, G.B. 8:319-322 (1998).
H. Davis et al., "Ezetimibe, a Potent Cholesterol Absorption Inhibitor, Inhibits the Developmentof Aterosclerosis in Apo E Knockout Mice", Arterioscler, Thromb. Vasc. Biol 21:2032-2038, (Dec. 2001).
Simova, E., "Aldol-type addition of hydrocinnamic acid esters to benzylideneaniline", Chemical Abstracts No. 15, 86 (Apr. 11, 1997).
Otto et al., Stereochemistry of dehydration and halogenation fo αR* and αS* isomeric 3-(α-hydroxybenzyl)-1,4 diphenyl=2 azetidinones, Chemical Abstracts No. 19, 99 (Nov. 7, 1983).
T. Durst et al, "Metallation of N-Substituted β-Lactams. A Method of the Introduction of 3-substituents into β-Lactams" Canadian Journal of Chemistry, 50:3196-3201 (1971).
Nobuki, O. et al., "Stereoselective syntheses of b-lactam derivatives by ultrasound promoted Reformatskii reaction" Chemical Abstracts No. 106, 17 (Apr. 27, 1987).
M. Hoekman, et al., "Synthesis of Homologues of 4,5-Dihydroxy- and 4-Hydroxy-5-oxohexanoic Acid γ-Lactones", J. Agric. Food Chem., 30:920-924 (1982).
H. Otto et al. "Darstellung and Stereochemie von 3-(α-Hydroxybenzyl)-1,4-diphenyl-2-azetidononen",Liebigs Ann. Chem. 1152-1161 (1983).
G. George et al. "3-(1-Hydroxyethyl)-2-Azetidinones From 3-Hydroxybutyrates and N-Arylaldimines" Tetrahedron Letters, 26:3903-3906 (1985).
Hart et al. "An Enantioselective Approach to Carbapenem Antibodies: Formal Synthesis of (+)-Thienamycin", 26 Tetrahedron Letters, 45:5493-5496 (1985).
Panfil, I. et al. "Synthesis of β-Lactams from α, β-Unsaturated Sugar δ-Lactones" 24 Heterocycles 6: 1609-1617 (1986).
D. Roger Illingworth, "An Overview of Lipid-Lower Drugs" Drugs 36:63:71 (1988).

Joseph L. Witztum, M.D., "Current Approaches to Drug Therapy for the Hyercholesterolemic Patient" Circulation 80:1101-1114 (1989).
B. Ram et al. "Potential Hypolipidemic agents:Part V", 29B Indian J. Chem. 1134-37 (1990).
Schnitzer-Polokoff, R. et al., "Effects of Acyl-CoA: Choleseraol O-Acyltransferase Inhibition on Cholesterol Absorption and Plasma Lipoprotein Composition in Hamsters" Comp. Biochem. Physiol. 99A:665-670 (1991).
Horie, M. et al, "Hypolipidemic effects of NB-598 in dogs" Atherosclerosis 88:183-192 (1991).
Baxter, A., "Squalestatin 1, a Potent Inhibitor of Squalene Synthase, Which Lowers Serum Cholesterol in Vivo", The Journal of Biological Chemistry 267:11705-11708 (1992).
Summary Factfile, "Anti-Antherosclerotic Agents" Current Drugs Ltd. (1992).
Harwood H. James, "Pharmacologic consequences of cholesterol absorption inhibition: alteration in cholesterol metabolism and reduction in plasma cholesterol concentration induced by the synthetic saponin β-tigogenin cellobioside (CP-88818; tiqueside) 1" Journal of Lipid Research 34:377-395 (1993).
Salisbury, B. et al., "Hypocholesterolemic activity of a novel inhibitor of cholesterol absorption, SCH 48461" Atherosclerosis 115:45-63 (1995).
Clader, J. W. et al., "Substituted (1,2-Diarylethyl)amide Acyl-CoA;Cholesterol Acyltransferase Inhibitors: Effect of Polar Groups in Vitro and in Viro Activity" Journal of Medicinal Chemistry 38:1600-1607 (1995).
Sybertz, E., "Sch 48461, a novel inhibitor of cholesterol absorption" Atherosclerosis pp. 311-315 (1995).
Vaccaro, W , et al, "2-Azetidinone Cholesterol Absorption Inhibitors; Increased Potency by Substitution of the C-4 Phenyl Ring", Bioorg. & Med. Chem. 6:1429-1437 (1998).
G. Wu et al, A Novel One-Step Diastereo-and enantioselective formation of transazetidinones and its application to the total synthesis of cholesterol absorption inhibitors A.C.S. (Apr. 21, 1999).
B. Staels, "New Roles for PPARS in Cholesterol Homeostasis", Trends in Pharmacological Sciences, 22:9 p. 444 (Sep. 2001).
Abbott et al, "Tricor® Capsules, Micronized", Physicians Desk Reference, Jan. 8, 2001.
M. Feher et al., 1991, Lipids and Lipid Disorders, p. 1-87 (1991).
M. Ricote et al., "New Roles for PPAR in Cholesterol Homeostakis", Trends in Pharmacological Science, vol. 22, No. 9 441-443 (2001).
C. Dujovne et al, "Reduction of LDL Cholesteral in Patients with Primary Hypercholesterolemia by SCH 48461: Results of a mutlicenter Dose-Ranging Study", J. Clin,. Pharm. 41:1 70-78 (Jan. 2001).
W. Oppolzer et al., "Asymmetric Diels—Alder Reactions, Facile Preparation and Structure of Sulfonamido—Isobornyl Acrylates", Tetrahedron Letters No. 51, 25:5885-5888 (1984).
M. Davidson et al., "Colesevelam Hydischloride: a non-absorbed, polymeric cholesterol lowing agent", Expert Opinion Investigating Drugs, 11:2663-71, (Nov. 2000).
M. Davidson et al., "Colesevelam hydrochloride (cholestagel): a new, potent bileacid sequestrant associated with a low incidence of gastrointestinal effects", 159 Arch. Intern. Med. 16 1893-900 (Sep. 1999).
I. Wester, "Cholesterol—Lowering effect of plant sterols", Euro. J.Lipid, Sci. Tech. 37-44 (2000).
A. Andersson et al., "Cholesterol—lowering effects of a stanol estercontaining low fat margarine used in conjunction with a strict lipid-lowering diet", 1 European Heart. J. Supplements S80-S90 (1999).
H. Gylling et al, Reduction of Serum Cholesterol in Postmenopausal Women with Previous Myocardial Infarction and Cholesterol Malabsorption induced by Dietary Sitostarol Ester Margarine, 96 Circulation12 4226-4231 (Dec. 16, 1997).
T. Miettinen et al, "Reduction of Serum Cholesterol with Sitostanol-Ester Margarine in a Mildly Hypercholesterolemic Population", New England Journal of Med. 333 1308-1312 (Nov. 16, 1995).
T. Bocan et al., "The ACAT Inhibitor Avasimibe Reduces Macrophages and Matrix Metalloproteinase Expression in Atherosclerotic Lesions of Hypercholesterolemic Rabbits", Arterioscler Thromb Vasc. Biol. 70-79 (Jan. 2000).

M. Van Heek et al., "In Vivo Metabolism-Based Discovery of a Potent Cholesterol Absorption Inhibitor, SCH 58235, in the Rat and Rhesus Monkey through the indentification of the active metabolites of SCH48461," 283 *J. Pharma and Experimental Therapeutics 1* 157-163 (1997).

H. Davis et al., "The Cholesterol Absorption Inhibitor Ezetimible Inhibits the Development of Atherosclerosis in apo E knockout (-/-) mice fed low fat and western diets," *151 Atherosclerosis 1*:133 (Jul. 2000).

L. Nguyen et al., "Unexpected Failure of Bile Acid Malabsorption to Stimulate Cholesterol Synthesis in Sitosterolemia with Xanthomatosis", *10 Atherosclerosis 2*, 289-297 (1990).

L. Nguyen et al. "Regulation of Cholesterol Biosynthesisin Sitosterolemia: effects of lovastatin, Cholestyramine, and dietary sterol restriction," *32 J.Lipid Res*. 1941-1948 (1991).

M. Cobb et al., "Sitosterolemia: Opposing Effects of cholestyramine and Lovastatin on Plasma Sterol Levels in a Homozygous Girl and Her Heterozygous Father," *45 Metabolism 6* 673-679 (Jun. 1996).

M. Huettinger et al., "Hypolipidemic Activity of HOE-402 is mediated by Stimulation of the LDL Receptor Pathway", *13 Arteriosclerosis and Thrombosis 7* 1005-1012 (Jul. 1993).

J. Best et al., "Diabetic Dyslipidaemia", *59 Drugs 5* 1101-1111 (May 2000).

P. Chong, et al, "Current, New and Future Treatment in Dyslipidaemia and Atherosclerosis", *60 Drugs 1* 55-93 (Jul. 2000).

M. Brown et al, "A Receptor—Mediated Pathway for Cholesterol Homeostasis", *232 Science* 34-47 (Apr. 4, 1986).

L. Lipka et al., "Reduction of LDL-Cholesterol and Elevation of HDL-Cholesterol in Subjects with Primary Hypercholesterolemia by SCH 58235: Pooled Analysis of Two Phase II Studies", *JACC* 257A (Feb. 2000).

Medical Economics, Co., Inc., *Physician's Desk Reference*, 207-208, 2054 (55th Ed. 2001).

K. Fassbender et al., "Simvastatin Strongly Reduces Levels of Alzheimer's Disease β-Amyloid Peptides Aβ 42 and Aβ40 in vitro and in vivo", *PNAs Early Edition*, www.phas.org/cgi/doi/10,1073/phas.081620098 (2001).

Andrx Announces Results of Alzheimer's Disease Clinical Study, *Andrx Corporate Release* (Apr. 11, 2001).

Andrx (ADRX): Pos Phase II Results Using Avicor in Alzheimer's: Str Buy; $130,*US Bancorp Piper*, Apr. 12, 2001.

Statins May Protect Against Alzheimer's Disease; much research needed, *Geriatrics* Feb. 2001.

Dementia and Statins, *The Lancet* Mar. 17, 2001.

Research & Development: Andrx Says Cholestrol Drug May Treat Alzheimers, *Reuters* Apr. 11, 2001.

Cholesterol Drugs Ease Alzheimer's Damage; www.usatoday.com Apr. 10, 2001.

Lovastation XL of Use Alzheimer's? News Edge (May 2, 2001).

L. Refolo et al, Hypercholesterolemia Accelerates the Alzheimer's Amyloid Pathology in a Transgenic Morse Model, *Neurobiology of Disease* 321-331 (2000).

D. Kang et al., "Modulation of Amyloid β-protein Clearance and Alheimer's Disease Susceptibility by the LDL Receptor—Related Protein Pathway", *Journal of Clinical Investigation* 106:9, 1159-1166 (Nov. 2000).

Y.A. Kesaniewmi, "Intestinal Cholesterol Absorption Efficiency in Man is Related to Apoprotein E Phenotype", *J. Clin. Invest.* 80(2) 578-81 (Aug. 1987).

J. Busciglio et al., "Generation of β-amyloid in the secretary pathway in neuronal and nonneuronal cells", *90 Proc. Nat'l. Acad. Sci, USA*, 2092-2096 *Neurobiology* (Mar. 1993).

L. Farrer et al., "Assessment of Genetic Risk for Alzheimer's Disease Among first Degree Relatives", *Annals of Neurology* 25:5, 485-493 (May 1989).

A. Goate et al., "Segregation of a Missense Mutation in the Amyloid Precursor Protein Gene with Familial Alzheimer's Disease", *349 Nature No. 6311*, 704-706 (Feb. 21, 1991).

D. Mann et al., "The Pattern of Acquisition of Plaques and Tangle in the Brains of Patients Under 50 years of Age with Down's Syndrome", *89 J. Neuro. Sci.*, 169-179 (Feb. 1989).

G. McKhann et al., "Clinical Diagnosis of Alzheimer's Disease", *34 Neurology No. 7*, 939-944 (Jul. 1984).

D. Selokoe, "Alzheimer's Disease: Genotypes, Pheontype and Treatments", *275 Science*, 630-631 (Jan. 31, 1997).

C. Van Duijn, et al., "Familial Aggregation of Alzheimer's Disease and Related Disorders: A collaborative Re-Analysis of Case-Control Studies", *20 Int'l J. Epidemiology No. 2* (Suppl. 2), 513-520 (1991).

T Nagahara et al., "Dibasic (Amidcinoaryl) Propanoic Acid Derivatives as Novel Blood Coagulation Factor Xa Inhibitors", J. Med. Chem 37:1200-1207 (1994).

Mellott et al., "Acceleration of Recombinant Tissue-Type Plasminogen Activator Induced Reperfusion and Prevention of Reocculsion by Recombinant Antistasin, a selective factor Xa Inhibitor, in a Canine Model of Femoral Arterial Thrombosis", *Circulation Research*, 70:1152-1160 (1992).

Sitko et al., "Conjunctive Enhancement of Enzymatic Thrombolysis and Prevention of Thrombotic Reocclusion With the Selective Factor Xa Inhibitor, Tick Anticoagulant Peptide", *Circulation*, 85:805-815 (1992).

Seymour et al., 1994, *Biochemistry*, 33:3949-3959.

Markwardt, 1994, *Thrombosis and Hemostasis*, 72:477-479.

Mendall et al., "C-Reactive Protein and its relation to cardiovascular risk factor: A population based cross sectional study", *BMJ*; 312:1061-1065 (Apr. 27, 1996).

Ridker P. et al., "Prospective Studies of C-Reactive Protein as a risk factor for cardiovascular disease", 46 *J. Investig. Med.*; 8:391-395 (1998).

L. Gruberb, 2000, "Inflammatory Markers in Acute Coronary Syndromes: C-reative protein (CRP) and Chlamydia", *American Heart Association Scientific Sessions*.

Waters, D. et al., "A Controlled Clinical Trial to Assess the Effect of a Calcium Channel Blocker on the Progression of Coronary Atherosclerosis", *Circulation*; 82:1940-1953 (1990).

Fleckenstein, 1985, *Cir. Res*. vol. 52 (Suppl. 1) 3-16.

Fleckenstein, 1983, "Experimental Facts and Therapeutic Prospects", *John Wiley*, New York, pp. 286-313.

McCall, D., 1985, *Curr. Pract. Cardiol*. vol. 10, 1-11.

Remington 1995, The Science and Practice of Pharmacy, (19th Ed. 1995) p. 963.

M. Christie et al., "Early—Onset Amyloid Deposition and Cognitive Deficits in Transgenic Mice Expressing a Double Mutant Form of Amyloid Precursor Protein 695", *276 J. Biol. Chem. No. 24*; 21562-70 (Jun. 15, 2001).

C. Janus et al., "Aβ Peptide Immunization Reduces Behavioral impairment and Plaques in a Model of Alzheimer's Disease", *408 Nature 21/28*; 979-982 (Dec. 2000).

Manual of Laboratory Operations, Lipids Research Clinics Program Report, Washington, D.C., *U.S. Dept. of Health, Education and Welfare Publication*; 1:75-628 (1974).

Steiner, PM et al., Standardization of Micromethods for Plasma Cholesterol, Triglyceride and HDL-Cholesterol with the Lipid Clinic's Methodology [abstract], *J. Clin. Chem. Clin. Bichem*; 19:850 (1981).

Steele WG, et al., Enzymatic Determinations of Cholesterol in High Density Lipoprotein Fractions Prepared by Precipitation Technique,*22 Clin. Chem.*; 1:98-101 (1976).

Salen et al., "Increased Sitosterol Absorption, Decreased Removal and Expanded Body Pools Compensate for Reduced Choelsterol Syntheses in Sitosterolemia with Xanthomatosis", *J. Lipd Res*.,; 30:1319-1330 (1989).

Lutjohann et al., "Sterol Absorption and Sterol Balance in Phytosterolemia Evaluated by Deuterium-Labeled Sterols: Effect of Sitostanol Treatment", *J. Lipid Res.*; 36:8; 1763-1773 (1995).

Zhang et al., "Calpain Inhibitor I Increases B- Amyloid Peptide by Inhibiting the Degradation of the Substrate of γ- Secretase" 274 *J. Biol, Chem.*, 13:8966-8972 (1999).

Zhang et al., "Biochemical Characterization of the γ-Secretase Activity that Produces B-Amyloid Peptides", Biochemistry 40:5049-5055 (2001).

Ida et al., "Analysis of Heterogeneous BA4 Peptides in Human Cerebrospinal Fluid and Blood by a Newly Developed Sensitive Western Blot Assay", 271 *J. Biol, Chem.*; 37:22908-22914 (1996).

Lichtlen, P.R. et al., 1990, *Lancet*; 335:1109-1113.

Bays et al., "Effectiveness and Tolerability of Ezetimibe in Patients with Primary Hypercholesterolemia: Pooled Analysis of Two Phase II Studies", *Clinical Therapeutics*, 23:1209-1230 (2001).

E. Leitersdorf et al., "Cholesterol absorption inhibition: filling an unmet need in lipid-lowering management", *European Heart Journal Suppliment*, 3:E17-E23 (Jun. 2001).

Bauer et al., "Ezetimibe Does not Affect the Pharmacokinetics or Pharmacodynamics of Warfarin", *Clinical Pharmacology and Therapeutics*, 69:2 p. 5 (Mar. 6-10, 2001).

Keung et al., Ezetimibe Does Not Affect the Pharmacokinetics of oral Contraceptives, *Clinical Pharmacology and Therapeutics*, 69:2 p. 55 (Mar. 6-10, 2001).

Kosoglou et al., "Pharmacodynamic interaction between fenofibrate and the Cholesterol Absorption Inhibitor Ezetimibe", *Workshops Lipid Lowering Drugs 72nd EAS Congress*, p. 38 (May 21-23, 2001).

T. Kosoglou et al., "Coadministration of Ezetimibe and Fenofibrate Leads to Favorable Effects On Apo CII and LDL Subfractions", *Posters 11. Lipid Lowering Drugs/Novel, 72nd EAS Congress*, p. 89 (May 21-23, 2001).

L. Reyderman et al., "Assessment of a Multiple-Dose Drug Interaction Between Ezetimibe and Gemfibrozil", Presented at XIV Int'l Symp. on Drugs Affecting Lipid Metabolism (DALM) N.Y. (Sep. 9-12, 2001).

P. Statkevich et al., "Ezetimibe Does Not Affect the Pharmacokinetics and Pharmacodynamics of Glipizide",*Clinical Pharmacology & Therapeutics*, 69:67 (Mar. 6-10, 2001).

Knopp et al, "Effect of Ezetimibe on Serum Concentrations of Lipid-Soluble Vitamins", *Posters 11. Lipid Lowering Drug/Novel 72nd EAS Congress*, p. 90 (May 21-23, 2001).

Kosoglou et al., "Pharmacodynamic Interaction Between Fenofibrate and the Cholesterol Absorption Inhibitor Ezetimibe", *Workshops Lipid Lowering Drugs, 72nd EAS Congress*, p. 38 (Mar. 6-10, 2001).

Bays et al., "Low-Density Lipoprotein Cholesterol Reduction By SCH 58235 (Ezetimibe), A Novel Inhibitor of Intestinal Cholesterol Absorption, in 243 Hypercholesterolemic Subjects: Results of a Dose-Response Study", *XII International Symposium on Atherosclerosis*, Stockholm, Sweden (Jun. 25-29, 2000).

Castaner et al, "Ezetimibe-Hypolipidemic Cholesterol Absorption Inhibitor", *Drugs of the Future*, 25(7):679-685 (2000).

Lipka et al., "Reduction of LDL-Cholesterol and Elevation of HDL-Cholesterol in Subjects with Primary Hypercholesterolemia by Ezetimibe (SCH 58235): Pooled Analysis of Two Phase II Studies", *American College of Cardiology Annual Meeting*, Anaheim, CA (Mar. 12-15, 2000).

Van Heek et al., "Comparison of the activity and disposition of the novel cholesterol absorption inhibitor , SCH58235, and its glucuronide, SCH60663", *British Journal of Pharmacology*, 129:1748-1754 (2000).

Van Heek et al., 2000, "The potent cholesterol absorption inhibitor, ezetimibe, is glucuronidated in the intestine, localizes to the intestine, and circulates enterohepatically", *XII International Symposium of Atherosclerosis*, Stockholm Sweden (Jun. 25-29, 2000).

Iannucci et al., "Metabolism of SCH 58235 in the Human, Rat and Dog", *47th ASMS Conference on Mass Spectrometry and Allied Topics*, Dallas, TX (Jun. 13-17, 1999).

Reiss et al., "An Enzymatic Synthesis of Glucuronides of Azetidinone-based Cholesterol Absorption Inhibitors", *Bioorganics & Medicinal Chemistry*, 7:2199-2202 (1999).

Rosenblum et al., "Discovery of 1-(4-Flurophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem.* 41:973-980 (1998).

Vaccaro et al., "Sugar-Substituted 2-Azetidinone Cholesterol Absorption Inhibitors: Enhanced Potency by Modification of the Sugar", *Bioorganic & Medicinal Chemistry Letters*, 8:313-318 (1998).

Zaks et al., "Enzymatic Glucuronidation of a Novel Cholesterol Absorption Inhibitor, SCH 58235", *Applied Biochemistry and Biotechnology*, 73:205-214 (1998).

W. Insull et al., Postmenopausal Hypercholesterolemic Women Derive Additive Benefit from Raloxifene and Simvastatin on Lipid Parameters , *World Heart Federation 6th International Symposium on Global Risk of Coronary Heart Disease and Stroke—Abstract Book*, p. 35 (Jun. 12-15, 2002).

L. Simons et al., 2002, "Ezetimibe added to on-going statin therapy for treatment of primary hypercholesterolemia: Efficacy and safety in patients with Type 2 diabetes mellitus", presented at the 38th Annual Meeting of the EASD, Sep. 1-5, 2002.

C. Allain et al, 1974, "Enzymatic Determination of Total Serum Cholesterol", *Clinical Chemical*, 20:470-475.

R. Mayrhofer et al., 1980, "Simple-Preparation of 3-Benzylidene-2-azetilidinones", *Synthesis*, 247-248.

Burrier, R.E. et al., 1994, "Demonstration of a Direct Effect on Hepatic Acyl CoA:Cholesterol Acyl Transferase (ACAT) Activity By An Orally Administered Enzyme Inhibitor in the Hamster", *Biochemical Pharmacology* 47:1545-1551.

Burrier, R.E. et al., 1994, "The Effect of Acyl CoACholesterol Acyltransferase Inhibitor on the Uptake, Esterification and Secretion of Cholesterol by the Hamster Small Intestine", *The Journal of Pharmacology and Experimental Therapeutics* 272:156-163.

E.F. Binder et al., "Effects of Hormone Replacement Therapy on Serum Lipids in Elderly Women. A Randomized, Placebo-Controlled Trial", *134 Ann. Intern. Med.* 9:754-760 (May 1, 2001).

MR Haymart et al., "Optimal Management of Dyslipidemia in Women and Men", 2 *J. Gend. Specif. Med.* 6:37-42 (Nov.-Dec. 1997).

"Framingham Heart Study Analysis Reveals Some Primary Prevention Subgroups Are Being Overlooked", *Heartwire* (Apr. 12, 2001).

"Detection Evaluation, and Treatment of High Blood Cholesterol in Adults (Adult Treatment Panel III), Third Report of the National Cholesterol Education Program (NCEP)", *NIH Publication No. 01-3670* (May 2001).

Van Heek et al., "Ezetimibe, A Potent Cholesterol Absorption Inhibitor, Normalizes Combined Dyslipidemia in Obese Hyperinsulinemic Hamsters", 50 *Diabetes* 1330-1335 (Jun. 2001).

"Additional Statins Show Anti-Inflammatory Effect", 103 *Circulation* 1933-35 (Apr. 17, 2001).

H. Hauser, et al, "Identification of a Receptor Mediating Absorption of Dietary Cholesterol in the Intestine", *Biochemistry* 37:17843-17850, 1998.

G. Salen, et al., "Sitosterolemia", *Journal of Lipid Research* 33:945-955, 1992.

Stedman's Medical Dictionary, 27th Edition, p. 1381.

P.F. Belamarich et al., "Response to Diet and Cholestyramine in a Patient with Sitosterolemia", *Pediatrics*, 977-981, (Dec. 1990).

G. Salen et al., "Lethal Atherosclerosis Associated With Abnormal Plasma and Tissue Sterol Composition in Sitosterolemia With Xanthomatosis", *Journal of Lipid Research*, 1126-1133, (Sep. 1985).

G.R. Thompson et al., Novel Lipid-Regulation Drugs, Exp. Opin. Invest. Drugs, 9(11):2619-2628, 2000.

International Search Report dated Dec. 18, 2002 corresponding to PCT Application No. PCT/US02/01195.

Exhibit A: SCH 58235 Micronized (ezetimibe), Drug Formulation Development Summary.

Exhibit B: SCH 58235 (ezetimibe), Drug Formulation Development Summary.

Exhibit C: SCH 58235 (ezetimibe), Drug Formulation Development Summary.

Exhibit D: SCH 58235 (ezetimibe), Drug Formulation Development Summary.

Exhibit E: SCH 58235 (ezetimibe), Drug Formulation Development Summary.

Exhibit F: SCH 58235 (ezetimibe), Drug Formulation Development Summary.

Exhibit G: SCH 58235 (ezetimibe), Drug Formulation Development Summary.

Exhibit H: SCH 58235 (ezetimibe), Drug Formulation Development Summary.

Exhibit 1: Master Sheet for the SCH 58235 and Lovastatin Research Study, *Schering-Plough Research Institute* (Protocol No. C906-411), p. 1576-1585.

Exhibit 2: Medical Research Study #1055/97, SCH 58235: Bioavailability of Single Oral Doses of Two Prototype Tablet Formulations and the Reference Capsule Formulation of SCH 58235 in Normal Male Volunteers: A Four Way Crossover Study #C97-221-01, Informed Consent, *Peninsular Testing Corporation*, p. 106-112.

Exhibit 3: Consent Form to Participate in a Research Study, "A Phase II Double Blind Dose Response Investigation of Efficacy and Safety of Four Doses of SCH 58235 Compared to Placebo in Subjects with Primary Hypercholesterolemia," *Schering-Plough Research Institute* (Protocol No. C98-010), p. 1558-1566.

Exhibit 4: Medical Research Study #1096/99, SCH 58235: Pharmacokinetic Pharmacodynamic Drug Interaction Study with Digoxin in Healthy Volunteers #C98-114, Informed Consent, *Peninsular Testing Corporation*, p. 124-130.

Exhibit 5: Informed Consent, "SCH 58235: Assessment of Multiple-Dose Drug Interaction Between 58235 and Gemfibrozil in Healthy Volunteers," *Schering-Plough Research Institute*, p. 1-8.

Thompson, G.R. et al., "Novel lipid-regulating drugs" *Expert Opinion on Investigational Drugs* 9(11):2619-2628 (2000), XP008011782 abstract; figure 8.

Kosoglou, T. et al., "Coadministration of ezetimibe and fenofibrate leads to favorable effects on Apo CII and LDL subfractions" *Atherosclerosis* 2:89 (2001), XP1132089 abstract.

Luis Gruberg, MD, Inflammatory Markers in Acute Coronary Syndromes: C-reactive Protein (CRP) and Chlamydia, American Heart Association Scientific Sessions 2000.

Nguyen LB, et al., "A molecular defect in hepatic cholesterol biosynthesis in sitosterolemia with xanthomatosis" J Clin Invest, 86: 923-931 (1990).

Lien B. Nguyen, et al., "Regulation of Cholesterol biosynthesis in sitosterolemia: effects of lovastatin, cholestyramine, and dietary sterol restriction" Journal of Lipid Research, vol. 32, pp. 1941-1948 (1991).

T.A. Miettinen, "Inhibition of cholesterol absorption by HMG-CoA reductase inhibitor" Eur J Clin Pharmacol (1991) 40 [Suppl 1]: S19-S 21.

H. Vanhanen, et al., "Pravastatin Lowers Serum Cholesterol, Cholesterol-Precursor Sterols, Fecal Steroids, and Cholesterol Absorption in Man", Metabolism, vol. 47, No. 6 (Jun. 1992), pp. 588-595.

Matti I.J. Uusitupa, et al., "Lathosterol and Other Noncholesterol Sterols During Treatment of Hypercholesterolemia With Lovastatin Alone and With Cholestyramine or Guar Gum" Arteriosclerosis and Thrombosis, vol. 12, No. 7, 807-813 (1992).

Zetia Product Brochure, Merck/Schering-Plough Pharmaceuticals (Oct. 2002).

R. Steiner et al., "Sitosterolemia", http://www.emedicine.com/ped/topic 2110.htm (Apr. 5, 2005).

Sorbera et al., Netoglitazone, *Drugs of the Future*, 2002, 27(2): 132-139.

Michel Farnier, Nouvelles approaches médicamenteuses dans le traitement des dyslipidémies, *MT Endocrinologie*, 2002, 4:252-259.

Berger et al., Physiological and Therapeutic Roles of Peroxisome Proliferator-Activated Receptors, *Diabetes Technology & Therapeutics*, 2002, 4:163-174.

Stuart B. Rosenblum et al., Discovery of 1-(4-Fluorophenyl)-(3R)-[3-(fluorophenyl)-(3S)-hydroxypropyl]-(4S)-(4-hydroxyphenyl)-2-azetidinone (SCH 58235): A Designed, Potent, Orally Active Inhibitor of Cholesterol Absorption, *J. Med. Chem.* 41:973-980 (1998).

Gilbert R. Thompson et al., Novel lipid-regulating drugs, *Exp. Opin. Invest. Drugs* 9(11):2619-2628 (2000).

T. Kosoglou et al., Coadministration of Ezetimibe and Fenofibrate Leads to Favorable Effects on Apo CIII and LDL Subfractions, *Atherosclerosis* 2:89 (2001).

Harry R. Davis et al., The Synergistic Hypocholesterolemic Activity of the Potent Cholesterol Absorption Inhibitor, Ezetimibe, in Combination With 3-Hydroxy-3-Methylglutaryl Coenzyme A Reductase Inhibitors in Dogs, *Metabolism* 50 (10):1234-1241 (2001).

Study Showed Ezetimibe Significantly Reduced Levels of LDL Cholesterol or "Bad" Cholesterol in Patients, Schering-Plough Press Release.

T. Kosoglou et al., Pharmacodynamic Interaction Between Fenofibrate and the Cholesterol Absorption Inhibitor Ezetimibe, *Atherosclerosis* (2):38 (2001).

Remington's Pharmaceutical Sciences, 18th ed. 1990 p. 1319, 1633-1647.

Baker S G et al., Treatment of homozygous familial hypercholesterolaemia with probucol, *South African Medical Journal* (1982).

R. Milanese et al., Xantomi E Ipercolesterolemia: Prevalenza, Diagnosi e Terapia, *Chron. Derm*. 455-61 (1990).

Wo-Ju Lee, "A drug useful for treating atherosclerosis and lipoproteinemia", A Lecture of Pharmacology, vol. III, 411 (1993)—Medical Culture History.

* cited by examiner

USE OF SUBSTITUTED AZETIDINONE COMPOUNDS FOR THE TREATMENT OF SITOSTEROLEMIA

CROSS-REFERENCE TO RELATED APPLICATION

This application claims the benefit of U.S. Provisional Application Ser. No. 60/264,645 filed Jan. 26, 2001.

FIELD OF THE INVENTION

The present invention provides methods and pharmaceutical compositions for treating or preventing sitosterolemia by administering to a mammal in need of such treatment an effective amount of at least one treatment composition comprising at least one sterol absorption inhibitor and optionally, an effective amount of at least one bile acid sequestrant or other lipid lowering agent.

BACKGROUND OF THE INVENTION

Sitosterolemia is a genetic lipid storage disorder characterized by increased levels of sitosterol and other plant sterols in the plasma and other tissues due to increased non-selective intestinal absorption of sterols and decreased hepatic removal. Individuals having sitosterolemia can exhibit one or more of the following conditions: tendon and tuberous xanthomas, arthritis, hemolytic episodes, accelerated atherosclerosis and myocardial infarctions, and can die at an early age due to extensive coronary atherosclerosis. See Nguyen et al., "Regulation of cholesterol biosynthesis in sitosterolemia: effects of lovastatin, cholestyramine, and dietary sterol restriction", Vol 32, *Journal of Lipid Research*, pp. 1941-1948, (1991), incorporated by reference herein.

Sitosterolemia can be treated with bile acid sequestrants (such as cholestyramine, colesevelam hydrochloride and colestipol), however, these compounds have a tendency to cause constipation in patients and therefore compliance with this treatment is difficult. Bile acid sequestrants (insoluble anion exchange resins) bind bile acids in the intestine, interrupting the enterohepatic circulation of bile acids and causing an increase in the fecal excretion of steroids. Use of bile acid sequestrants is desirable because of their non-systemic mode of action. Bile acid sequestrants can lower intrahepatic cholesterol and promote the synthesis of apo B/E (LDL) receptors which bind LDL from plasma to further reduce cholesterol levels in the blood.

Alternative treatments include ileal bypass surgery and selective low density lipoprotein plasmapheresis, which are physically undesirable for the patient.

An improved treatment for sitosterolemia is needed which can reduce the concentration of sterols in plasma and tissues and inhibit associated debilitating physical effects. Also, treatments which reduce the plasma or tissue concentration of non-cholesterol sterols such as phytosterols and 5α-stanols are needed.

SUMMARY OF THE INVENTION

The present invention provides a method of treating or preventing sitosterolemia, comprising administering to a mammal in need of such treatment an effective amount of at least one sterol absorption inhibitor, or pharmaceutically acceptable salt or solvate of the least one sterol absorption inhibitor, or prodrug of the at least one sterol absorption inhibitor or pharmaceutically acceptable salt or solvate of the least one sterol absorption inhibitor, or mixture thereof.

In another embodiment, the present invention provides a method of treating or preventing sitosterolemia, comprising administering to a mammal in need of such treatment: (1) an effective amount of at least one sterol absorption inhibitor, or pharmaceutically acceptable salt or solvate of the least one sterol absorption inhibitor, or prodrug of the least one sterol absorption inhibitor or pharmaceutically acceptable salt or solvate of the least one sterol absorption, or mixture thereof; and (2) an effective amount of at least one bile acid sequestrant or other lipid lowering agent.

In another embodiment, the present invention provides a method of treating or preventing sitosterolemia comprising administering to a mammal in need of such treatment: (1) an effective amount of at least one sterol absorption inhibitor, or pharmaceutically acceptable salt or solvate of the least one sterol absorption inhibitor, or prodrug of the least one sterol absorption or pharmaceutically acceptable salt or solvate of the least one sterol absorption inhibitor, or mixture thereof; and (2) at least one sterol biosynthesis inhibitor.

Other embodiments of the present invention include pharmaceutical compositions for the treatment or prevention of sitosterolemia comprising an effective amount of the compositions or combinations used in the methods described above in a pharmaceutically acceptable carrier.

Another embodiment of the present invention is a method of reducing plasma or tissue concentration of at least one non-cholesterol sterol (such as a phytosterol), 5α-stanol, or mixture thereof, comprising administering to a mammal in need of such treatment an effective amount of at least one treatment composition comprising an effective amount of at least one sterol absorption inhibitor or at least one stanol absorption inhibitor, or pharmaceutically acceptable salt or solvate of the least one sterol absorption inhibitor or the at least one stanol absorption inhibitor, or prodrug of the least one sterol absorption inhibitor or the at least one stanol absorption inhibitor or pharmaceutically acceptable salt or solvate of the least one sterol absorption inhibitor or the at least one stanol absorption inhibitor, or mixture thereof.

Yet another embodiment of the present invention is a method of reducing plasma or tissue concentration of at least one non-cholesterol sterol, 5α-stanol, or mixture thereof, comprising administering to a sitosterolemic mammal in need of such treatment an effective amount of at least one treatment composition comprising an effective amount of at least one sterol absorption inhibitor or at least one stanol absorption inhibitor, or pharmaceutically acceptable salt or solvate of the least one sterol absorption inhibitor or the at least one stanol absorption inhibitor, or prodrug of the least one sterol absorption inhibitor or the at least one stanol absorption inhibitor or pharmaceutically acceptable salt or solvate of the least one sterol absorption inhibitor or the at least one stanol absorption inhibitor, or mixture thereof.

In another embodiment, the present invention provides a method of treating vascular disease, arteriosclerosis and/or atherosclerosis, comprising administering to a mammal in need of such treatment an effective amount of at least one treatment composition comprising an effective amount of at least one sterol absorption inhibitor or at least one stanol absorption inhibitor, or pharmaceutically acceptable salt or solvate of the least one sterol absorption inhibitor or the at least one stanol absorption inhibitor, or prodrug of the least one sterol absorption inhibitor or the at least one stanol absorption inhibitor or pharmaceutically acceptable salt or solvate of the least one sterol absorption inhibitor or the at least one stanol absorption inhibitor, or mixture thereof to reduce plasma or tissue concentration of at least one non-cholesterol sterol, 5α-stanol or mixture thereof.

In another embodiment, the present invention provides a method of preventing or reducing risk of a cardiovascular event comprising administering to a mammal an effective amount of at least one treatment composition comprising an effective amount of at least one sterol absorption inhibitor or at least one stanol absorption inhibitor, or pharmaceutically acceptable salt or solvate of the least one sterol absorption inhibitor or the at least one stanol absorption inhibitor, or prodrug of the least one sterol absorption inhibitor or the at least one stanol absorption inhibitor or pharmaceutically acceptable salt or solvate of the least one sterol absorption inhibitor or the at least one stanol absorption inhibitor, or mixture thereof to reduce plasma or tissue concentration of at least one non-cholesterol sterol, 5α-stanol or mixture thereof.

In another embodiment, the present invention provides a method of preventing or reducing risk of a cardiovascular event comprising administering an effective amount of at least one treatment composition as described above to reduce plasma or tissue concentration of at least one non-cholesterol sterol, 5α-stanol or mixture thereof to a mammal having no history of clinically evident coronary heart disease prior to the initial administration.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

The present invention provides methods, pharmaceutical compositions and combinations for treating or preventing sitosterolemia and conditions or symptoms associated with sitosterolemia such as are discussed above. Another aspect of the present invention provides methods, pharmaceutical compositions and combinations for reducing the plasma or tissue concentration of non-cholesterol sterols, such as phytosterol(s), and/or 5α-stanol(s), or mixtures thereof, in a mammal which can be useful in the treatment and/or prevention of vascular conditions or disease, such as vascular inflammation, arteriosclerosis, atherosclerosis, hypercholesterolemia and sitosterolemia, and cardiovascular events, stroke and/or obesity.

Useful treatment compositions comprise one or more sterol absorption inhibitors and/or stanol absorption inhibitors such as are represented by Formulae (I-XI) shown below.

In one embodiment one or more sterol absorption inhibitors and/or stanol absorption inhibitors useful in the methods, compositions or combinations of this invention are represented by Formula (I):

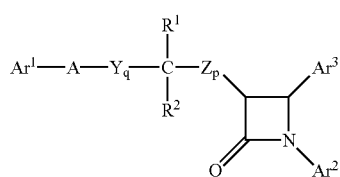

(I)

or isomers of the compounds of Formula (I), or pharmaceutically acceptable salts or solvates of the compounds of Formula (I) or of the isomers of the compounds of Formula (I), or prodrugs of the compounds of Formula (I) or of the isomers, salts or solvates of the compounds of Formula (I), wherein in Formula (I):

$Ar^1$ is $R^3$-substituted aryl;
$Ar^2$ is $R^4$-substituted aryl;
$Ar^3$ is $R^5$-substituted aryl;
Y and Z are independently selected from the group consisting of —$CH_2$—, —CH(lower alkyl)- and —C(dilower alkyl)-;
A is —O—, —S—, —S(O)— or —S(O)$_2$—;
$R^1$ is selected from the group consisting of —$OR^6$, —O(CO)$R^6$, —O(CO)$OR^9$ and —O(CO)$NR^6R^7$; $R^2$ is selected from the group consisting of hydrogen, lower alkyl and aryl; or $R^1$ and $R^2$ together are =O;
q is 1, 2 or 3;
p is 0, 1, 2, 3 or 4;
$R^5$ is 1-3 substituents independently selected from the group consisting of —$OR^6$, —O(CO)$R^6$, —O(CO)$OR^9$, —O($CH_2$)$_{1-5}OR^9$, —O(CO)$NR^6R^7$, —$NR^6R^7$, —$NR^6$(CO)$R^7$, —$NR^6$(CO)$OR^9$, —$NR^6$(CO)$NR^7R^8$, —$NR^6SO_2$-lower alkyl, —$NR^6SO_2$-aryl, —$CONR^6R^7$, —$COR^6$, —$SO_2NR^6R^7$, S(O)$_{0-2}$-alkyl, S(O)$_{0-2}$-aryl, —O($CH_2$)$_{1-10}$—$COOR^6$, —O($CH_2$)$_{1-10}CONR^6R^7$, o-halogeno, m-halogeno, o-lower alkyl, m-lower alkyl, -(lower alkylene)-$COOR^6$, and —CH=CH—$COOR^6$;
$R^3$ and $R^4$ are independently 1-3 substituents independently selected from the group consisting of $R^5$, hydrogen, p-lower alkyl, aryl, —$NO_2$, —$CF_3$ and p-halogeno;
$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferred compounds of Formula I include those in which $Ar^1$ is $R^3$-substituted phenyl, especially (4-$R^3$)-substituted phenyl. $Ar^2$ is preferably $R^4$-substituted phenyl, especially (4-$R^4$)-substituted phenyl. $Ar^3$ is preferably $R^5$-substituted phenyl, especially (4-$R^5$)-substituted phenyl. Mono-substitution of each of $Ar^1$, $Ar^2$ and $Ar^3$ is preferred.

Y and Z are each preferably —$CH_2$—. $R^2$ is preferably hydrogen. $R^1$ is preferably —$OR^6$ wherein $R^6$ is hydrogen, or a group readily metabolizable to a hydroxyl (such as —O(CO)$R^6$, —O(CO)$OR^9$ and —O(CO)$NR^6R^7$, defined above). Also preferred are compounds wherein $R^1$ and $R^2$ together are =O.

The sum of q and p is preferably 1 or 2, more preferably 1. Preferred are compounds wherein p is zero and q is 1. More preferred are compounds wherein p is zero, q is 1, Y is —$CH_2$— and $R^1$ is —$OR^6$, especially when $R^6$ is hydrogen.

Another group of preferred compounds is that in which $Ar^1$ is $R^3$-substituted phenyl, $Ar^2$ is $R^4$-substituted phenyl and $Ar^3$ is $R^5$-substituted phenyl.

Also preferred are compounds wherein $Ar^1$ is $R^3$-substituted phenyl, $Ar^2$ is $R^4$-substituted phenyl, $Ar^3$ is $R^5$-substituted phenyl, and the sum of p and q is 1 or 2, especially 1. More preferred are compounds wherein $Ar^1$ is $R^3$-substituted phenyl, $Ar^2$ is $R^4$-substituted phenyl, $Ar^3$ is $R^5$-substituted phenyl, p is zero and q is 1.

A is preferably —O—.

$R^3$ is preferably —$COOR^6$, —$CONR^6R^7$, —$COR^6$, —$SO_2NR^6R^7$, S(O)$_{0-2}$-alkyl, S(O)$_{0-2}$-aryl, $NO_2$ or halogeno. A more preferred definition for $R^3$ is halogeno, especially fluoro or chloro.

$R^4$ is preferably hydrogen, lower alkyl, —$OR^6$, —O(CO)$R^6$, —O(CO)$OR^9$, —O(CO)$NR^6R^7$, —$NR^6R^7$, $COR^6$ or halogeno, wherein $R^6$ and $R^7$ are preferably independently hydrogen or lower alkyl, and $R^9$ is preferably lower alkyl. A more preferred definition for $R^4$ is hydrogen or halogeno, especially fluoro or chloro.

$R^5$ is preferably —$OR^6$, —$O(CO)R^6$, —$O(CO)OR^9$, —$O(CO)NR^6R^7$, —$NR^6R^7$, -(lower alkylene-$COOR^6$ or —CH=CH—$COOR^6$, wherein $R^6$ and $R^7$ are preferably independently hydrogen or lower alkyl, and $R^9$ is preferably lower alkyl. A more preferred definition for $R^5$ is —$OR^6$, -(lower alkylene)-$COOR^6$ or —CH=CH—$COOR^6$, wherein $R^6$ is preferably hydrogen or lower alkyl.

In another embodiment, one or more sterol absorption inhibitors and/or stanol absorption inhibitors useful in the methods, compositions or combinations of this invention are represented by Formula (II):

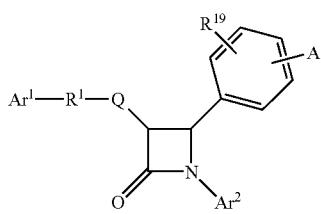

(II)

or isomers of the compounds of Formula (II), or pharmaceutically acceptable salts or solvates of the compounds of Formula (II) or of the isomers of the compounds of Formula (II), or prodrugs of the compounds of Formula (II) or of the isomers, salts or solvates of the compounds of Formula (II), wherein in Formula (II) above:

A is selected from the group consisting of $R^2$-substituted heterocycloalkyl, $R^2$-substituted heteroaryl, $R^2$-substituted benzofused heterocycloalkyl, and $R^2$-substituted benzofused heteroaryl;

$Ar^1$ is aryl or $R^3$-substituted aryl;
$Ar^2$ is aryl or $R^4$-substituted aryl;
Q is a bond or, with the 3-position ring carbon of the azetidinone, forms the spiro group

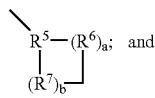

$R^1$ is selected from the group consisting of:
—$(CH_2)_q$—, wherein q is 2-6, provided that when Q forms a spiro ring, q can also be zero or 1;
—$(CH_2)_e$-G-$(CH_2)_r$—, wherein G is —O—, —C(O)—, phenylene, —$NR^8$— or —$S(O)_{0-2}$—, e is 0-5 and r is 0-5, provided that the sum of e and r is 1-6;
—($C_2$-$C_6$ alkenylene)-; and
—$(CH_2)_f$—V—$(CH_2)_g$—, wherein V is $C_3$-$C_6$ cycloalkylene, f is 1-5 and g is 0-5, provided that the sum of f and g is 1-6;

$R^5$ is

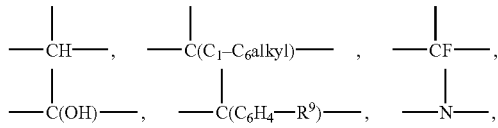

or 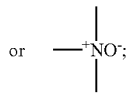

$R^6$ and $R^7$ are independently selected from the group consisting of —$CH_2$—, —CH($C_1$-$C_6$ alkyl)-, —C(di-($C_1$-$C_6$) alkyl), —CH=CH— and —C($C_1$-$C_6$ alkyl)=CH—; or $R^5$ together with an adjacent $R^6$, or $R^5$ together with an adjacent $R^7$, form a —CH=CH— or a —CH=C($C_1$-$C_6$ alkyl)- group;

a and b are independently 0, 1, 2 or 3, provided both are not zero; provided that when $R^6$ is —CH=CH— or —C($C_1$-$C_6$ alkyl)=CH—, a is 1; provided that when $R^7$ is —CH=CH— or —C($C_1$-$C_6$ alkyl)=CH—, b is 1; provided that when a is 2 or 3, the $R^6$'s can be the same or different; and provided that when b is 2 or 3, the $R^7$'s can be the same or different;

and when Q is a bond, $R^1$ also can be:

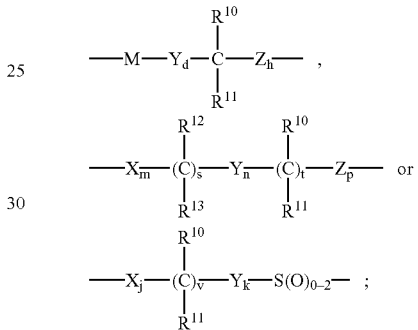

M is —O—, —S—, —S(O)— or —$S(O)_2$—;
X, Y and Z are independently selected from the group consisting of —$CH_2$—, —CH($C_1$-$C_6$ alkyl) and —C(di-($C_1$-$C_6$)alkyl);
$R^{10}$ and $R^{12}$ are independently selected from the group consisting of —$OR^{14}$, —$O(CO)R^{14}$, —$O(CO)OR^{16}$ and —$O(CO)NR^{14}R^{15}$;
$R^{11}$ and $R^{13}$ are independently selected from the group consisting of hydrogen, ($C_1$-$C_6$)alkyl and aryl; or $R^{10}$ and $R^{11}$ together are =O, or $R^{12}$ and $R^{13}$ together are =O;
d is 1, 2 or 3;
h is 0, 1, 2, 3 or 4;
s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1, the sum of m, t and n is 1-5;
v is 0 or 1;
j and k are independently 1-5, provided that the sum of j, k and v is 1-5;
$R^2$ is 1-3 substituents on the ring carbon atoms selected from the group consisting of hydrogen, ($C_1$-$C_{10}$)alkyl, ($C_2$-$C_{10}$)alkenyl, ($C_2$-$C_{10}$)alkynyl, ($C_3$-$C_6$)cycloalkyl, ($C_3$-$C_6$)cycloalkenyl, $R^{17}$-substituted aryl, $R^{17}$-substituted benzyl, $R^{17}$-substituted benzyloxy, $R^{17}$-substituted aryloxy, halogeno, —$NR^{14}R^{15}$, $NR^{14}R^{15}$($C_1$-$C_6$ alkylene)-, $NR^{14}R^{15}C(O)(C_1$-$C_6$ alkylene)-, —NHC(O)$R^{16}$, OH, $C_1$-$C_6$ alkoxy, —OC(O)$R^{16}$, —$COR^{14}$, hydroxy($C_1$-$C_6$)alkyl, ($C_1$-$C_6$)alkoxy($C_1$-$C_6$)alkyl, $NO_2$, —$S(O)_{0-2}R^{16}$, —$SO_2NR^{14}R^{15}$ and —($C_1$-$C_6$ alkylene)$COOR^{14}$; when $R^2$ is a substituent on a heterocycloalkyl ring, $R^2$ is as defined, or is =O or

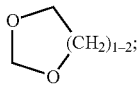

and, where R² is a substituent on a substitutable ring nitrogen, it is hydrogen, $(C_1-C_6)$alkyl, aryl, $(C_1-C_6)$alkoxy, aryloxy, $(C_1-C_6)$alkylcarbonyl, arylcarbonyl, hydroxy, $-(CH_2)_{1-6}CONR^{18}R^{18}$,

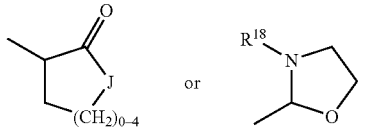

wherein J is $-O-$, $-NH-$, $-NR^{18}-$ or $-CH_2-$;

$R^3$ and $R^4$ are independently selected from the group consisting of 1-3 substituents independently selected from the group consisting of $(C_1-C_6)$alkyl, $-OR^{14}$, $-O(CO)R^{14}$, $-O(CO)OR^{16}$, $-O(CH_2)_{1-5}OR^{14}$, $-O(CO)NR^{14}R^{15}$, $-NR^{14}R^{15}$, $-NR^{14}(CO)R^{15}$, $-NR^{14}(CO)OR^{16}$, $-NR^{14}(CO)NR^{15}R^{19}$, $-NR^{14}SO_2R^{16}$, $-COOR^{14}$, $-CONR^{14}R^{15}$, $-COR^{14}$, $-SO_2NR^{14}R^{15}$, $S(O)_{0-2}R^{16}$, $-O(CH_2)_{1-10}-COOR^{14}$, $-O(CH_2)_{1-10}CONR^{14}R^{15}$, $-(C_1-C_6 \text{ alkylene})-COOR^{14}$, $-CH=CH-COOR^{14}$, $-CF_3$, $-CN$, $-NO_2$ and halogen;

$R^8$ is hydrogen, $(C_1-C_6)$alkyl, aryl$(C_1-C_6)$alkyl, $-C(O)R^{14}$ or $-COOR^{14}$;

$R^9$ and $R^{17}$ are independently 1-3 groups independently selected from the group consisting of hydrogen, $(C_1-C_6)$alkyl, $(C_1-C_6)$alkoxy, $-COOH$, $NO_2$, $-NR^{14}R^{15}$, OH and halogeno;

$R^{14}$ and $R^{15}$ are independently selected from the group consisting of hydrogen, $(C_1-C_6)$alkyl, aryl and aryl-substituted $(C_1-C_6)$alkyl;

$R^{16}$ is $(C_1-C_6)$alkyl, aryl or $R^{17}$-substituted aryl;

$R^{18}$ is hydrogen or $(C_1-C_6)$alkyl; and $R^{19}$ is hydrogen, hydroxy or $(C_1-C_6)$alkoxy.

As used in Formula (II) above, "A" is preferably an R²-substituted, 6-membered heterocycloalkyl ring containing 1 or 2 nitrogen atoms. Preferred heterocycloalkyl rings are piperidinyl, piperazinyl and morpholinyl groups. The ring "A" is preferably joined to the phenyl ring through a ring nitrogen. Preferred R² substituents are hydrogen and lower alkyl. $R^{19}$ is preferably hydrogen.

Ar² is preferably phenyl or R⁴-phenyl, especially (4-R⁴)-substituted phenyl. Preferred definitions of R⁴ are lower alkoxy, especially methoxy, and halogeno, especially fluoro.

Ar¹ is preferably phenyl or R³-substituted phenyl, especially (4-R³)-substituted phenyl.

There are several preferred definitions for the —R¹-Q-combination of variables:

Q is a bond and R¹ is lower alkylene, preferably propylene;

Q is a Spiro group as defined above, wherein preferably R⁶ and R⁷ are each ethylene and R⁵ is

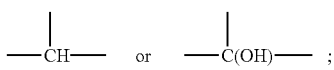

Q is a bond and R¹ is

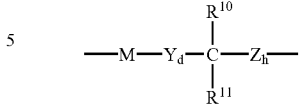

wherein the variables are chosen such that R¹ is $-O-CH_2-CH(OH)-$;

Q is a bond and R¹ is

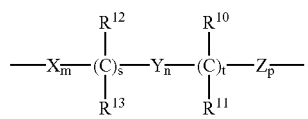

wherein the variables are chosen such that R¹ is $-CH(OH)-(CH_2)_2-$; and

Q is a bond and R¹ is

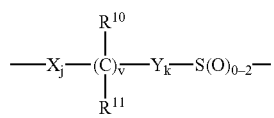

wherein the variables are chosen such that R¹ is $-CH(OH)-CH_2-S(O)_{0-2}-$.

In another embodiment, one or more sterol absorption inhibitors and/or stanol absorption inhibitors useful in the methods, compositions or combinations of this invention are represented by Formula (III):

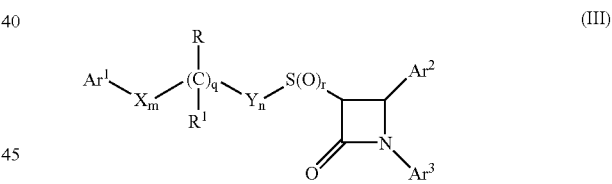

or isomers of the compounds of Formula (III), or pharmaceutically acceptable salts or solvates of the compounds of Formula (III) or of the isomers of the compounds of Formula (III), or prodrugs of the compounds of Formula (III) or of the isomers, salts or solvates of the compounds of Formula (III), wherein in Formula (III) above:
Ar¹ is aryl, $R^{10}$-substituted aryl or heteroaryl;
Ar² is aryl or R⁴-substituted aryl;
Ar³ is aryl or R⁵-substituted aryl;
X and Y are independently selected from the group consisting of $-CH_2-$, $-CH(\text{lower alkyl})-$ and $-C(\text{dilower alkyl})-$;
R is $-OR^6$, $-O(CO)R^6$, $-O(CO)OR^9$ or $-O(CO)NR^6R^7$; R¹ is hydrogen, lower alkyl or aryl; or R and R¹ together are $=O$;
q is 0 or 1;
r is 0, 1 or 2;
m and n are independently 0, 1, 2, 3, 4 or 5; provided that the sum of m, n and q is 1, 2, 3, 4 or 5;

$R^4$ is 1-5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}COOR^6$, —$O(CH_2)_{1-10}CONR^6R^7$, -(lower alkylene)$COOR^6$ and —CH=CH—$COOR^6$;

$R^5$ is 1-5 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}COOR^6$, —$O(CH_2)_{1-10}CONR^6R^7$, —$CF_3$, —CN, —$NO_2$, halogen, -(lower alkylene)$COOR^6$ and —CH=CH—$COOR^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1-5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}COOR^6$, —$O(CH_2)_{1-10}CONR^6R^7$, —$CF_3$, —CN, —$NO_2$ and halogen.

Within the scope of Formula III, there are two preferred structures. In Formula IIIA, q is zero and the remaining variables are as defined above, and in Formula IIIB, q is 1 and the remaining variables are as defined above:

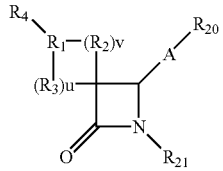

IIIA

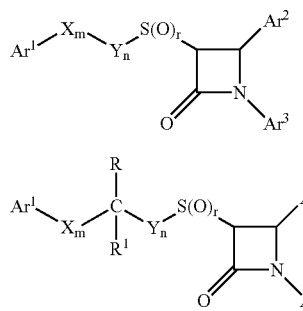

IIIB $R^4$, $R^5$ and $R^{10}$ are each preferably 1-3 independently selected substituents as set forth above. Preferred are compounds of Formula (III) wherein $Ar^1$ is phenyl, $R^{10}$-substituted phenyl or thienyl, especially (4-$R^{10}$)-substituted phenyl or thienyl. $Ar^2$ is preferably $R^4$-substituted phenyl, especially (4-$R^4$)-substituted phenyl. $Ar^3$ is preferably phenyl or $R^5$-substituted phenyl, especially (4-$R^5$)-substituted phenyl. When $Ar^1$ is $R^{10}$-substituted phenyl, $R^{10}$ is preferably halogeno, especially fluoro. When $Ar^2$ is $R^4$-substituted phenyl, $R^4$ is preferably —$OR^6$, especially wherein $R^6$ is hydrogen or lower alkyl. When $Ar^3$ is $R^5$-substituted phenyl, $R^5$ is preferably halogeno, especially fluoro. Especially preferred are compounds of Formula III wherein $Ar^1$ is phenyl, 4-fluorophenyl or thienyl, $Ar^2$ is 4-(alkoxy or hydroxy)phenyl, and $Ar^3$ is phenyl or 4-fluorophenyl.

X and Y are each preferably —$CH_2$—. The sum of m, n and q is preferably 2, 3 or 4, more preferably 2. When q is 1, n is preferably 1 to 5.

Preferences for X, Y, $Ar^1$, $Ar^2$ and $Ar^3$ are the same in each of Formulae IIIA and IIIB.

In compounds of Formula IIIA, the sum of m and n is preferably 2, 3 or 4, more preferably 2. Also preferred are compounds wherein the sum of m and n is 2, and r is 0 or 1.

In compounds of Formula IIIB, the sum of m and n is preferably 1, 2 or 3, more preferably 1. Especially preferred are compounds wherein m is zero and n is 1. $R^1$ is preferably hydrogen and R is preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above), or R and $R^1$ together form a =O group.

In another embodiment, one or more sterol absorption inhibitors and/or stanol absorption inhibitors useful in the methods, compositions or combinations of this invention are represented by Formula (IV):

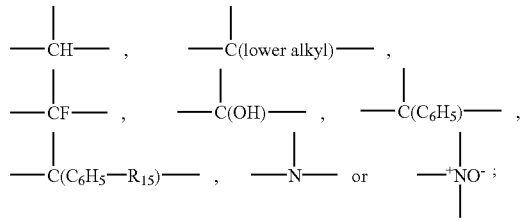

(IV)

or isomers of the compounds of Formula (IV), or pharmaceutically acceptable salts or solvates of the compounds of Formula (IV) or of the isomers of the compounds of Formula (IV), or prodrugs of the compounds of Formula (IV) or of the isomers, salts or solvates of the compounds of Formula (IV), wherein in Formula (IV) above:

$R_1$ is $$\begin{array}{c} | \\ -CH- \\ | \end{array}, \quad \begin{array}{c} | \\ -C(\text{lower alkyl})- \\ | \end{array},$$

$$\begin{array}{c} | \\ -CF- \\ | \end{array}, \quad \begin{array}{c} | \\ -C(OH)- \\ | \end{array}, \quad \begin{array}{c} | \\ -C(C_6H_5)- \\ | \end{array},$$

$$\begin{array}{c} | \\ -C(C_6H_5-R_{15})- \\ | \end{array}, \quad \begin{array}{c} | \\ -N- \\ | \end{array} \text{ or } \begin{array}{c} | \\ -{}^+NO^-- \\ | \end{array};$$

$R_2$ and $R_3$ are independently selected from the group consisting of: —$CH_2$—, —CH(lower alkyl)-, —C(di-lower alkyl)-, —CH=CH— and —C(lower alkyl)=CH—; or $R_1$ together with an adjacent $R_2$, or $R_1$ together with an adjacent $R_3$, form a —CH=CH— or a —CH=C(lower alkyl)- group;

u and v are independently 0, 1, 2 or 3, provided both are not zero;

provided that when $R_2$ is —CH=CH— or —C(lower alkyl)=CH—, v is 1;

provided that when $R_3$ is —CH=CH— or —C(lower alkyl)=CH—, u is 1;

provided that when v is 2 or 3, the $R_2$'s can be the same or different;

and provided that when u is 2 or 3, the $R_3$'s can be the same or different;

$R_4$ is selected from B—$(CH_2)_mC(O)$—, wherein m is 0, 1, 2, 3, 4 or 5;

B—$(CH_2)_q$—, wherein q is 0, 1, 2, 3, 4, 5 or 6;

B—$(CH_2)_e$-Z-$(CH_2)_r$—, wherein Z is —O—, —C(O)—, phenylene, —N($R_8$)— or —S(O)$_{0-2}$—, e is 0, 1, 2, 3, 4 or 5 and r is 0, 1, 2, 3, 4 or 5, provided that the sum of e and r is 0, 1, 2, 3, 4, 5 or 6;

B—($C_2$-$C_6$ alkenylene)-;
B—($C_4$-$C_6$ alkadienylene)-;
B—$(CH_2)_t$-Z-($C_2$-$C_6$ alkenylene)-, wherein Z is as defined above, and wherein t is 0, 1, 2 or 3, provided that the sum of t and the number of carbon atoms in the alkenylene chain is 2, 3, 4, 5 or 6;
B—$(CH_2)_f$—V—$(CH_2)_g$—, wherein V is $C_3$-$C_6$ cycloalkylene, f is 1, 2, 3, 4 or 5 and g is 0, 1, 2, 3, 4 or 5, provided that the sum of f and g is 1, 2, 3, 4, 5 or 6;
B—$(CH_2)_t$—V—($C_2$-$C_6$ alkenylene)- or
B—($C_2$-$C_6$ alkenylene)—V—$(CH_2)_t$—, wherein V and t are as defined above, provided that the sum of t and the number of carbon atoms in the alkenylene chain is 2, 3, 4, 5 or 6;
B—$(CH_2)_a$-Z-$(CH_2)_b$—V—$(CH_2)_d$—, wherein Z and V are as defined above and a, b and d are independently 0, 1, 2, 3, 4, 5 or 6, provided that the sum of a, b and d is 0, 1, 2, 3, 4, 5 or 6; or
T-$(CH_2)_s$—, wherein T is cycloalkyl of 3-6 carbon atoms and s is 0, 1, 2, 3, 4, 5 or 6; or
$R_1$ and $R_4$ together form the group

B is indanyl, indenyl, naphthyl, tetrahydronaphthyl, heteroaryl or W-substituted heteroaryl, wherein heteroaryl is selected from the group consisting of: pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

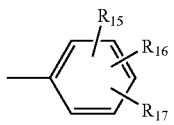

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —$CF_3$, —$OCF_3$, benzyl, $R_7$-benzyl, benzyloxy, $R_7$-benzyloxy, phenoxy, $R_7$-phenoxy, dioxolanyl, $NO_2$, —$N(R_8)(R_9)$, $N(R_8)(R_9)$-lower alkylene-, $N(R_8)(R_9)$-lower alkylenyloxy-, OH, halogeno, —CN, —$N_3$, —NHC(O)$OR_{10}$, —NHC(O)$R_{10}$, $R_{11}O_2$SNH—, $(R_{11}O_2S)_2$N—, —$S(O)_2NH_2$, —$S(O)_{0-2}R_8$, tert-butyldimethyl-silyloxymethyl, —C(O)$R_{12}$, —$COOR_{19}$, —$CON(R_8)(R_9)$, —CH=CHC(O)$R_{12}$, -lower alkylene-C(O)$R_{12}$, $R_{10}$C(O)(lower alkylenyloxy)-, $N(R_8)(R_9)$C(O)(lower alkylenyloxy)- and

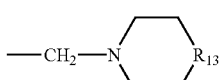

for substitution on ring carbon atoms, and the substituents on the substituted heteroaryl ring nitrogen atoms, when present, are selected from the group consisting of lower alkyl, lower alkoxy, —C(O)$OR_{10}$, —C(O)$R_{10}$, OH, $N(R_8)(R_9)$-lower alkylene-, $N(R_8)(R_9)$-lower alkylenyloxy-, —$S(O)_2NH_2$ and 2-(trimethylsilyl)-ethoxymethyl;

$R_7$ is 1-3 groups independently selected from the group consisting of lower alkyl, lower alkoxy, —COOH, $NO_2$, —$N(R_8)(R_9)$, OH, and halogeno;

$R_8$ and $R_9$ are independently H or lower alkyl;

$R_{10}$ is lower alkyl, phenyl, $R_7$-phenyl, benzyl or $R_7$-benzyl;

$R_{11}$ is OH, lower alkyl, phenyl, benzyl, $R_7$-phenyl or $R_7$-benzyl;

$R_{12}$ is H, OH, alkoxy, phenoxy, benzyloxy,

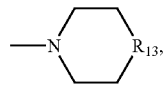

—$N(R_8)(R_9)$, lower alkyl, phenyl or $R_7$-phenyl;

$R_{13}$ is —O—, —$CH_2$—, —NH—, —N(lower alkyl)- or —NC(O)$R_{19}$;

$R_{15}$ $R_{16}$ and $R_{17}$ are independently selected from the group consisting of H and the groups defined for W; or $R_{15}$ is hydrogen and $R_{16}$ and $R_{17}$, together with adjacent carbon atoms to which they are attached, form a dioxolanyl ring;

$R_{19}$ is H, lower alkyl, phenyl or phenyl lower alkyl; and $R_{20}$ and $R_{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzofused heteroaryl and cyclopropyl, wherein heteroaryl is as defined above.

One group of preferred compounds of Formula IV is that in which $R_{21}$ is phenyl, W-substituted phenyl, indanyl, benzofuranyl, benzodioxolyl, tetrahydronaphthyl, pyridyl, pyrazinyl, pyrimidinyl, quinolyl or cyclopropyl, wherein W is lower alkyl, lower alkoxy, OH, halogeno, —$N(R_8)(R_9)$, —NHC(O)$OR_{10}$, —NHC(O)$R_{10}$, $NO_2$, —CN, —$N_3$, —SH, —$S(O)_{0-2}$-(lower alkyl), —$COOR_{19}$, —$CON(R_8)(R_9)$, —$COR_{12}$, phenoxy, benzyloxy, —$OCF_3$, —CH=C(O)$R_{12}$ or tert-butyldimethylsilyloxy, wherein $R_8$, $R_9$, $R_{10}$, $R_{12}$ and $R_{19}$ are as defined for Formula IV. When W is 2 or 3 substituents, the substituents can be the same or different.

Another group of preferred compounds of Formula IV is that in which $R_{20}$ is phenyl or W-substituted phenyl, wherein preferred meanings of W are as defined above for preferred definitions of $R_{21}$.

More preferred are compounds of Formula IV wherein $R_{20}$ is phenyl or W-substituted phenyl and $R_{21}$ is phenyl, W-substituted phenyl, indanyl, benzofuranyl, benzodioxolyl, tetrahydronaphthyl, pyridyl, pyrazinyl, pyrimidinyl, quinolyl or cyclopropyl;

wherein W is lower alkyl, lower alkoxy, OH, halogeno, —$N(R_8)(R_9)$, —NHC(O)$OR_{10}$, —NHC(O)$R_{10}$, $NO_2$, —CN, —$N_3$, —SH, —$S(O)_{0-2}$-(lower alkyl), —$COOR_{19}$, —CON$(R_8)(R_9)$, —$COR_{12}$, phenoxy, benzyloxy, —CH=CHC(O)$R_{12}$, —$OCF_3$ or tert-butyl-dimethyl-silyloxy, wherein when W is 2 or 3 substituents, the substituents can be the same or different, and wherein $R_8$, $R_9$, $R_{10}$, $R_{12}$ and $R_{19}$ are as defined in Formula IV.

Also preferred are compounds of Formula IV wherein $R_1$ is

Another group of preferred compounds of Formula IV is that wherein $R_2$ and $R_3$ are each —$CH_2$— and the sum of u and v is 2, 3 or 4, with u=v=2 being more preferred.

$R_4$ is preferably B—$(CH_2)_q$— or B—$(CH_2)_e$-Z-$(CH_2)_r$—, wherein B, Z, q, e and r are as defined above. B is preferably

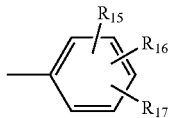

wherein $R_{16}$ and $R_{17}$ are each hydrogen and wherein $R_{15}$ is preferably H, OH, lower alkoxy, especially methoxy, or halogeno, especially chloro.

Preferably Z is —O—, e is 0, and r is 0.

Preferably q is 0-2.

$R_{20}$ is preferably phenyl or W-substituted phenyl.

Preferred W substituents for $R_{20}$ are lower alkoxy, especially methoxy and ethoxy, OH, and —$C(O)R_{12}$, wherein $R_{12}$ is preferably lower alkoxy.

Preferred definitions for $R_{21}$ are phenyl, lower alkoxy-substituted phenyl and F-phenyl.

Especially preferred are compounds of Formula IV wherein $R_1$ is

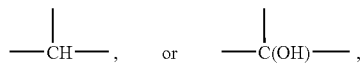

$R_2$ and $R_3$ are each —$CH_2$—, u=v=2, $R_4$ is B—$(CH_2)_q$—, wherein B is phenyl or phenyl substituted by lower alkoxy or chloro, q is 0-2, $R_{20}$ is phenyl, OH-phenyl, lower alkoxy-substituted phenyl or lower alkoxycarbonyl-substituted phenyl, and $R_{21}$ is phenyl, lower alkoxy-substituted phenyl or F-phenyl.

In another embodiment, one or more sterol absorption inhibitors and/or stanol absorption inhibitors useful in the methods, compositions or combinations of this invention are represented by Formulae (VA) and (VB):

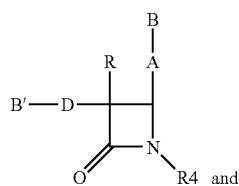

(VA)

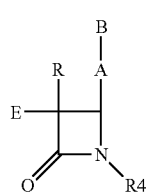

(VB)

or isomers thereof, or pharmaceutically acceptable salts or solvates of the compounds of Formulas (VA) and (VB) or of the isomers of the compounds of Formulas (VA) and (VB), or prodrugs of the compounds of Formulas (VA) and (VB) or of the isomers, salts or solvates of the compounds of Formulas (VA) and (VB), wherein in Formulae (VA) and (VB) above:

A is —CH═CH—, —C≡C— or —$(CH_2)_p$— wherein p is 0, 1 or 2;

B is

B' is

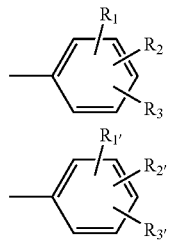

D is —$(CH_2)_mC(O)$— or —$(CH_2)_q$— wherein m is 1, 2, 3 or 4 and q is 2, 3 or 4;

E is $C_{10}$ to $C_{20}$ alkyl or —C(O)—($C_9$ to $C_{19}$)-alkyl, wherein the alkyl is straight or branched, saturated or containing one or more double bonds;

R is hydrogen, $C_1$-$C_{15}$ alkyl, straight or branched, saturated or containing one or more double bonds, or B—$(CH_2)_r$—, wherein r is 0, 1, 2, or 3;

$R_1$, $R_2$, $R_3$, $R_{1'}$, $R_{2'}$, and $R_{3'}$ are independently selected from the group consisting of hydrogen, lower alkyl, lower alkoxy, carboxy, $NO_2$, $NH_2$, OH, halogeno, lower alkylamino, dilower alkylamino, —NHC(O)$OR_5$, $R_6O_2$SNH— and —$S(O)_2NH_2$;

$R_4$ is

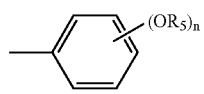

wherein n is 0, 1, 2 or 3;

$R_5$ is lower alkyl; and $R_6$ is OH, lower alkyl, phenyl, benzyl or substituted phenyl wherein the substituents are 1-3 groups independently selected from the group consisting of lower alkyl, lower alkoxy, carboxy, $NO_2$, $NH_2$, OH, halogeno, lower alkylamino and dilower alkylamino.

Preferred are compounds of Formula (VA) wherein R is hydrogen, saturated or mono-unsaturated $C_1$-$C_{10}$ alkyl or phenyl. Another group of preferred compounds of Formula (VA) is that wherein D is propyl (i.e., —$(CH_2)_q$— and q is 3). A third group of preferred compounds of Formula (VA) is that wherein $R_4$ is p-methoxyphenyl or 2,4,6-trimethoxyphenyl. Still another group of preferred compounds of Formula (VA) is that wherein A is ethylene or a bond (i.e., —$(CH_2)_p$— wherein p is zero). $R_{1'}$, $R_{2'}$, and $R_{3'}$ are preferably each hydrogen, and preferably $R_1$ is hydrogen, hydroxy, nitro, lower alkoxy, amino or t-butoxycarbonyl-amino and $R_2$ and $R_3$ are each hydrogen.

Especially preferred are compounds of Formula (VA) wherein $R_{1'}$, $R_{2'}$, and $R_{3'}$ are each hydrogen; $R_1$ is hydrogen, hydroxy, nitro, lower alkoxy, amino or t-butoxycarbonyl-amino and $R_2$ and $R_3$ are each hydrogen; R is hydrogen, ethyl or phenyl; D is propyl; $R_4$ is p-methoxyphenyl or 2,4,6-trimethoxyphenyl; and A is ethylene or a bond.

Preferred compounds of Formula (VA), wherein B' is phenyl, are shown in the following table:

| D | R | A | B | $R_4$ |
|---|---|---|---|---|
| —$(CH_2)_3$— | H | — | p-MeO-phenyl | p-MeO-phenyl |
| —$CH_2C(O)$— | phenyl | — | phenyl | p-MeO-phenyl |
| —$(CH_2)_3$— | H | — | phenyl | p-MeO-phenyl |
| —$(CH_2)_3$— | H | — | p-OH-phenyl | p-MeO-phenyl |
| —$(CH_2)_3$— | H | ethylene | p-MeO-phenyl | p-MeO-phenyl |
| —$(CH_2)_3$— | H | — | 3-MeO-phenyl | p-MeO-phenyl |
| —$(CH_2)_3$— | ethyl | — | phenyl | p-MeO-phenyl |
| —$(CH_2)_3$— | phenyl | — | phenyl | p-MeO-phenyl |
| —$(CH_2)_3$— | ethyl | — | phenyl | 2,4,6-tri-MeO-phenyl |
| —$(CH_2)_3$— | methyl | — | phenyl | p-MeO-phenyl |
| —$(CH_2)_3$— | H | — | p-$NH_2$-phenyl | p-MeO-phenyl |

The first-listed compound in the above table having the (3R,4S) absolute stereochemistry is more preferred.

Preferred compounds of Formula (VB) are those wherein R is hydrogen, methyl, ethyl, phenyl or phenylpropyl. Another group of preferred compounds of Formula (VB) is that wherein $R_4$ is p-methoxyphenyl or 2,4,6-trimethoxyphenyl. Still another group of preferred compounds of Formula (VB) is that wherein A is ethylene or a bond. Yet another group of preferred compounds of Formula (VB) is that wherein E is decyl, oleoyl or 7-Z-hexadecenyl. Preferably $R_1$, $R_2$ and $R_3$ are each hydrogen.

Especially preferred compounds of Formula (VB) are those wherein R is hydrogen, methyl, ethyl, phenyl or phenylpropyl; $R_4$ is p-methoxyphenyl or 2,4,6-trimethoxyphenyl; A is ethylene or a bond; E is decyl, oleoyl or 7-Z-hexadecenyl; and $R_1$, $R_2$ and $R_3$ are each hydrogen.

An especially preferred compound of Formula (VB) is that wherein E is decyl, R is hydrogen, B-A is phenyl and $R_4$ is p-methoxyphenyl.

In another embodiment, one or more sterol absorption inhibitors and/or stanol absorption inhibitors useful in the methods, compositions or combinations of this invention are represented by Formula (VI):

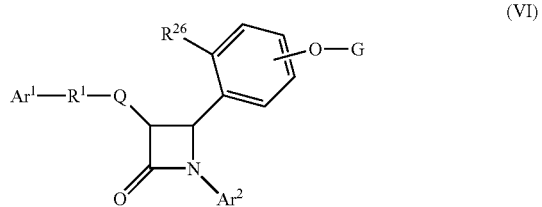

(VI)

or isomers thereof, or pharmaceutically acceptable salts or solvates of the compounds of Formula (VI) or of the isomers of the compounds of Formula (VI), or prodrugs of the compounds of Formula (VI) or of the isomers, salts or solvates of the compounds of Formula (VI), wherein in Formula (VI):

$R^{26}$ is H or $OG^1$;

G and $G^1$ are independently selected from the group consisting of H,

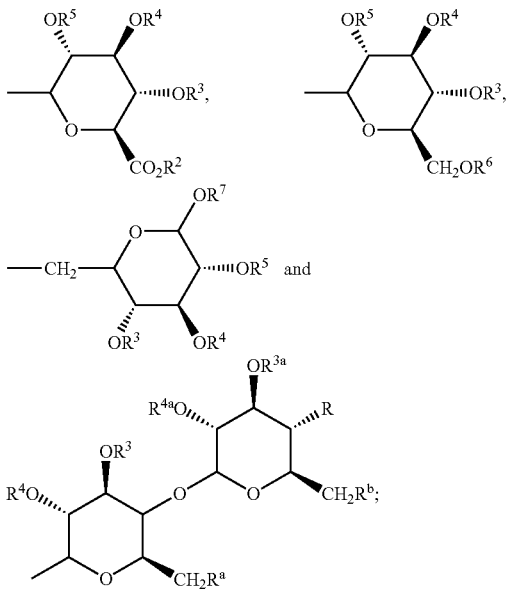

provided that when $R^{26}$ is H or OH, G is not H;

R, $R^a$ and $R^b$ are independently selected from the group consisting of H, —OH, halogeno, —$NH_2$, azido, ($C_1$-$C_6$)alkoxy($C_1$-$C_6$)-alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$-$C_6$)alkyl, aryl and aryl($C_1$-$C_6$)alkyl;

$R^3$, $R^4$, $R^5$, $R^7$, $R^{3a}$ and $R^{4a}$ are independently selected from the group consisting of H, ($C_1$-$C_6$)alkyl, aryl($C_1$-$C_6$)alkyl, —C(O)($C_1$-$C_6$)alkyl and —C(O)aryl;

$R^{30}$ is selected from the group consisting of $R^{32}$-substituted T, $R^{32}$-substituted-T-($C_1$-$C_6$)alkyl, $R^{32}$-substituted-($C_2$-$C_4$) alkenyl, $R^{32}$-substituted-($C_1$-$C_6$)alkyl, $R^{32}$-substituted-($C_3$-$C_7$)cycloalkyl and $R^{32}$-substituted-($C_3$-$C_7$)cycloalkyl($C_1$-$C_6$)alkyl;

$R^{31}$ is selected from the group consisting of H and ($C_1$-$C_4$) alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1-3 substituents independently selected from the group consisting of halogeno, ($C_1$-$C_4$)alkyl, —OH, phenoxy, —$CF_3$, —$NO_2$, ($C_1$-$C_4$) alkoxy, methylenedioxy, oxo, ($C_1$-$C_4$)alkylsulfanyl, ($C_1$-$C_4$) alkylsulfinyl, ($C_1$-$C_4$)alkylsulfonyl, —N($CH_3$)$_2$, —C(O)—NH($C_1$-$C_4$)alkyl, —C(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

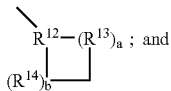

$R^1$ is selected from the group consisting of
—$(CH_2)_q$—, wherein q is 2-6, provided that when Q forms a spiro ring, q can also be zero or 1;
—$(CH_2)_e$-E-$(CH_2)_r$—, wherein E is —O—, —C(O)—, phenylene, —$NR^{22}$— or —$S(O)_{0-2}$—, e is 0-5 and r is 0-5, provided that the sum of e and r is 1-6;
—$(C_2$-$C_6)$alkenylene-; and
—$(CH_2)_f$—V—$(CH_2)_g$—, wherein V is $C_3$-$C_6$ cycloalkylene, f is 1-5 and g is 0-5, provided that the sum of f and g is 1-6;
$R^{12}$ is

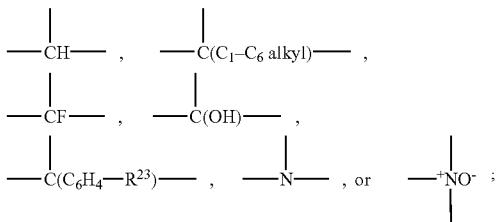

$R^{13}$ and $R^{14}$ are independently selected from the group consisting of —$CH_2$—, —$CH(C_1$-$C_6$ alkyl)-, —$C(di$-$(C_1$-$C_6)$ alkyl), —CH=CH— and —$C(C_1$-$C_6$ alkyl)=CH—; or $R^{12}$ together with an adjacent $R^{13}$, or $R^{12}$ together with an adjacent $R^{14}$, form a —CH=CH— or a —CH=$C(C_1$-$C_6$ alkyl)- group;

a and b are independently 0, 1, 2 or 3, provided both are not zero;

provided that when $R^{13}$ is —CH=CH— or —$C(C_1$-$C_6$ alkyl)=CH—, a is 1;

provided that when $R^{14}$ is —CH=CH— or —$C(C_1$-$C_6$ alkyl)=CH—, b is 1;

provided that when a is 2 or 3, the $R^{13}$'s can be the same or different; and provided that when b is 2 or 3, the $R^{14}$'s can be the same or different;

and when Q is a bond, $R^1$ also can be:

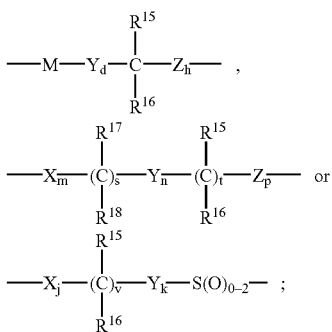

M is —O—, —S—, —S(O)— or —$S(O)_2$—;

X, Y and Z are independently selected from the group consisting of —$CH_2$—, —$CH(C_1$-$C_6)$alkyl- and —$C(di$-$(C_1$-$C_6)$alkyl);

$R^{10}$ and $R^{11}$ are independently selected from the group consisting of 1-3 substituents independently selected from the group consisting of $(C_1$-$C_6)$alkyl, —$OR^{19}$, —$O(CO)R^{19}$, —$O(CO)OR^{21}$, —$O(CH_2)_{1-5}OR^{19}$, —$O(CO)NR^{19}R^{20}$, —$NR^{19}R^{20}$, —$NR^{19}(CO)R^{20}$, —$NR^{19}(CO)OR^{21}$, —$NR^{19}(CO)NR^{20}R^{25}$, —$NR^{19}SO_2R^{21}$, —$COOR^{19}$, —$CONR^{19}R^{20}$, —$COR^{19}$, —$SO_2NR^{19}R^{20}$, $S(O)_{0-2}R^{21}$, —$O(CH_2)_{1-10}$—$COOR^{19}$, —$O(CH_2)_{1-10}CONR^{19}R^{20}$, —$(C_1$-$C_6$ alkylene)-$COOR^{19}$, —CH=CH—$COOR^{19}$, —$CF_3$, —CN, —$NO_2$ and halogen;

$R^{15}$ and $R^{17}$ are independently selected from the group consisting of —$OR^{19}$, —$O(CO)R^{19}$, —$O(CO)OR^{21}$ and —$O(CO)NR^{19}R^{20}$;

$R^{16}$ and $R^{18}$ are independently selected from the group consisting of H, $(C_1$-$C_6)$alkyl and aryl; or $R^{15}$ and $R^{16}$ together are =O, or $R^{17}$ and $R^{18}$ together are =O;

d is 1, 2 or 3;

h is 0, 1, 2, 3 or 4;

s is 0 or 1; t is 0 or 1; m, n and p are independently 0-4;

provided that at least one of s and t is 1, and the sum of m, n, p, s and t is 1-6;

provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

and when Q is a bond and $R^1$ is

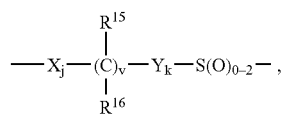

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1$-$C_6)$alkyl, aryl and aryl-substituted $(C_1$-$C_6)$alkyl;

$R^{21}$ is $(C_1$-$C_6)$alkyl, aryl or $R^{24}$-substituted aryl;

$R^{22}$ is H, $(C_1$-$C_6)$alkyl, aryl $(C_1$-$C_6)$alkyl, —$C(O)R^{19}$ or —$COOR^{19}$;

$R^{23}$ and $R^{24}$ are independently 1-3 groups independently selected from the group consisting of H, $(C_1$-$C_6)$alkyl, $(C_1$-$C_6)$alkoxy, —COOH, $NO_2$, —$NR^{19}R^{20}$, —OH and halogeno; and $R^{25}$ is H, —OH or $(C_1$-$C_6)$alkoxy.

$Ar^2$ is preferably phenyl or $R^{11}$-phenyl, especially (4-$R^{11}$)-substituted phenyl. Preferred definitions of $R^{11}$ are lower alkoxy, especially methoxy, and halogeno, especially fluoro.

$Ar^1$ is preferably phenyl or $R^{10}$-substituted phenyl, especially (4-$R^{10}$)-substituted phenyl. A preferred definition of $R^{10}$ is halogeno, especially fluoro.

There are several preferred definitions for the —$R^1$-Q- combination of variables:

Q is a bond and $R^1$ is lower alkylene, preferably propylene;

Q is a spiro group as defined above, wherein preferably $R^{13}$ and $R^{14}$ are each ethylene and $R^{12}$ is

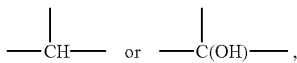

and $R^1$ is —$(CH_2)_q$— wherein q is 0-6;
Q is a bond and $R^1$ is

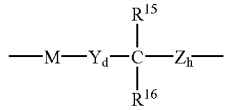

wherein the variables are chosen such that $R^1$ is —O—$CH_2$—CH(OH)—;
Q is a bond and $R^1$

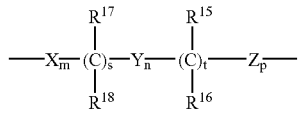

wherein the variables are chosen such that $R^1$ is —CH(OH)—$(CH_2)_2$—; and
Q is a bond and $R^1$ is

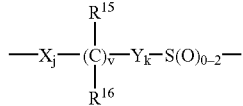

wherein the variables are chosen such that $R^1$ is —CH(OH)—$CH_2$—$S(O)_{0-2}$—.

A preferred compound of Formula (VI) therefore, is one wherein G and $G^1$ are as defined above and in which the remaining variables have the following definitions:

$Ar^1$ is phenyl or $R^{10}$-substituted phenyl, wherein $R^{10}$ is halogeno;

$Ar^2$ is phenyl or $R^{11}$-phenyl, wherein $R^{11}$ is 1 to 3 substituents independently selected from the group consisting of $C_1$-$C_6$ alkoxy and halogeno;

Q is a bond and $R^1$ is lower alkylene; Q, with the 3-position ring carbon of the azetidinone, forms the group

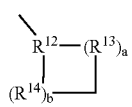

wherein preferably $R^{13}$ and $R^{14}$ are each ethylene and a and b are each 1, and wherein $R^{12}$ is

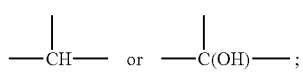

Q is a bond and $R^1$ is —O—$CH_2$—CH(OH)—; Q is a bond and $R^1$ is —CH(OH)—$(CH_2)_2$—; or Q is a bond and $R^1$ is —CH(OH)—$CH_2$—$S(O)_{0-2}$—.

Preferred variables for G and $G^1$ groups of the formulae

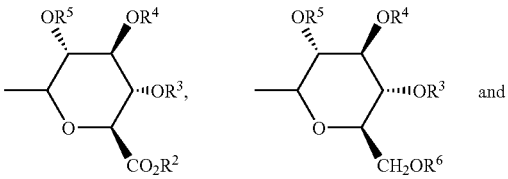

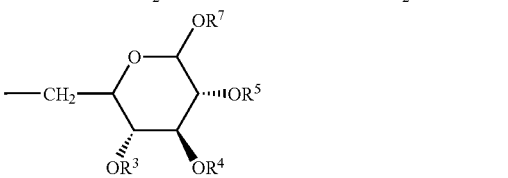

are as follows:
$R^2$, $R^3$, $R^4$, $R^5$, $R^6$ and $R^7$ are independently selected from the group consisting of H, ($C_1$-$C_6$)alkyl, benzyl and acetyl.

Preferred variables for group G or $G^1$ of the formula

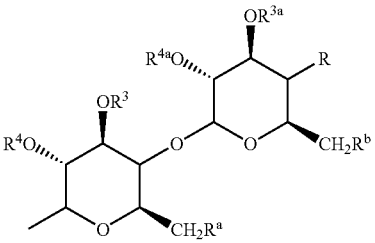

are as follows:
$R^3$, $R^{3a}$, $R^4$ and $R^{4a}$ are selected from the group consisting of H, ($C_1$-$C_6$)alkyl, benzyl and acetyl;

R, $R^a$ and $R^b$ are independently selected from the group consisting of H, —OH, halogeno, —$NH_2$, azido, ($C_1$-$C_6$) alkoxy($C_1$-$C_6$)alkoxy and —W—$R^{30}$, wherein W is —O—C(O)— or —O—C(O)—$NR^{31}$—, $R^{31}$ is H and $R^{30}$ is ($C_1$-$C_6$) alkyl, —C(O)—($C_1$-$C_4$)alkoxy-($C_1$-$C_6$)alkyl, T, T-($C_1$-$C_6$) alkyl, or T or T-($C_1$-$C_6$)alkyl wherein T is substituted by one or two halogeno or ($C_1$-$C_6$)alkyl groups.

Preferred $R^{30}$ substituents are selected from the group consisting of 2-fluorophenyl, 2,4-difluoro-phenyl, 2,6-dichlorophenyl, 2-methyl phenyl, 2-thienylmethyl, 2-methoxy-carbonylethyl, thiazol-2-yl-methyl, 2-furyl, 2-methoxycarbonylbutyl and phenyl.

Preferred combinations of R, $R^a$ and $R^b$ are as follows:
1) R, $R^a$ and $R^b$ are independently —OH or —O—C(O)—NH—$R^{30}$, especially wherein $R^a$ is —OH and R and $R^b$ are —O—C(O)—NH—$R^{30}$ and $R^{30}$ is selected from the preferred substituents identified above, or wherein R and $R^a$ are each —OH and $R^b$ is —O—C(O)—NH—$R^{30}$ wherein $R^{30}$ is 2-fluorophenyl, 2,4-difluoro-phenyl, 2,6-dichlorophenyl;
2) $R^a$ is —OH, halogeno, azido or ($C_1$-$C_6$)-alkoxy($C_{1-6}$) alkoxy, $R^b$ is H, halogeno, azido or ($C_1$-$C_6$)alkoxy($C_1$-$C_6$)-alkoxy, and R is —O—C(O)—NH—$R^{30}$, especially compounds wherein $R^a$ is —OH, $R^b$ is H and $R^{30}$ is 2-fluorophenyl;

3) R, $R^a$ and $R^b$ are independently —OH or —O—C(O)—$R^{30}$ and $R^{30}$ is $(C_1-C_6)$alkyl, T, or T substituted by one or two halogeno or $(C_1-C_6)$alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional classes of preferred compounds are those wherein the $C^{1'}$ anomeric oxy is beta, wherein the $C^{2'}$ anomeric oxy is beta, and wherein the R group is alpha.

G and $G^1$ are preferably selected from:

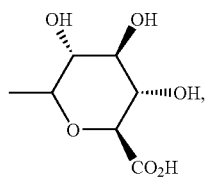
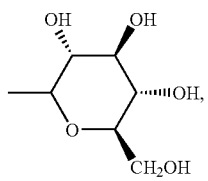
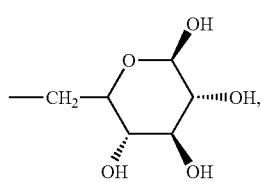
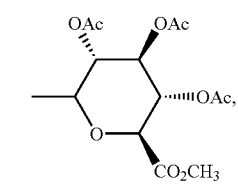
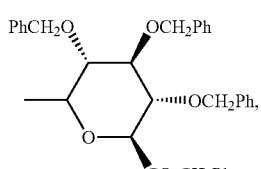
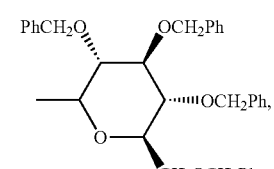
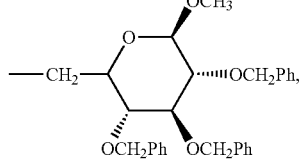
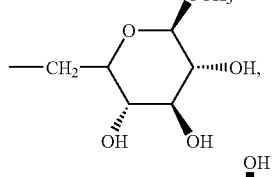
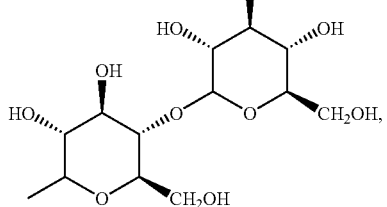

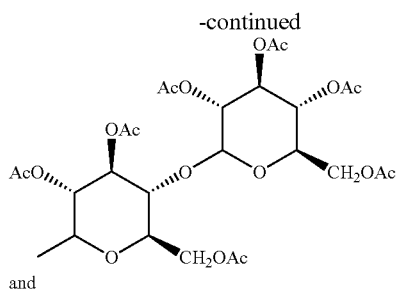

and

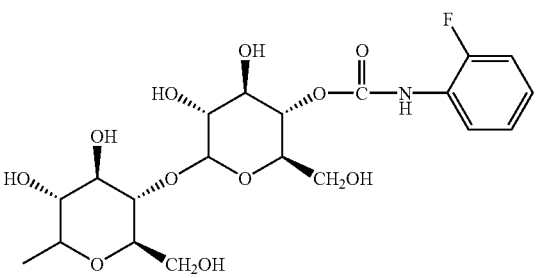

wherein Ac is acetyl and Ph is phenyl.

Preferably, $R^{26}$ is H or OH, more preferably H. The —O—G substituent is preferably in the 4-position of the phenyl ring to which it is attached.

In another embodiment, one or more sterol absorption inhibitors and/or stanol absorption inhibitors useful in the methods, compositions or combinations of this invention are represented by Formula (VII):

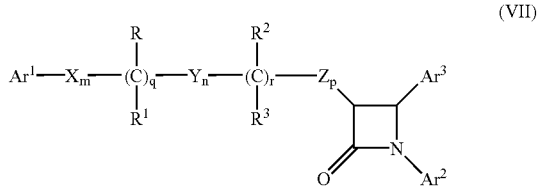

(VII)

or isomers thereof, or pharmaceutically acceptable salts or solvates of the compounds of Formula (VII) or of the isomers of the compounds of Formula (VII), or prodrugs of the compounds of Formula (VII) or of the isomers, salts or solvates of the compounds of Formula (VII), wherein in Formula (VII) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(dilower alkyl)-;

R and $R^2$ are independently selected from the group consisting of —$OR^6$, —O(CO)$R^6$, —O(CO)O$R^9$ and —O(CO)N$R^6R^7$;

$R^1$ and $R^3$ are independently selected from the group consisting of hydrogen, lower alkyl and aryl;

q is 0 or 1; r is 0 or 1; m, n and p are independently 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1-5 substituents independently selected from the group consisting of lower alkyl, $-OR^6$, $-O(CO)R^6$, $-O(CO)OR^9$, $-O(CH_2)_{1-5}OR^6$, $-O(CO)NR^6R^7$, $-NR^6R^7$, $-NR^6(CO)R^7$, $-NR^6(CO)OR^9$, $-NR^6(CO)NR^7R^8$, $-NR^6SO_2R^9$, $-COOR^6$, $-CONR^6R^7$, $-COR^6$, $-SO_2NR^6R^7$, $S(O)_{0-2}R^9$, $-O(CH_2)_{1-10}-COOR^6$, $-O(CH_2)_{1-10}CONR^6R^7$, -(lower alkylene)$COOR^6$, $-CH=CH-COOR^6$, $-CF_3$, $-CN$, $-NO_2$ and halogen;

$R^5$ is 1-5 substituents independently selected from the group consisting of $-OR^6$, $-O(CO)R^6$, $-O(CO)OR^9$, $-O(CH_2)_{1-5}OR^6$, $-O(CO)NR^6R^7$, $-NR^6R^7$, $-NR^6(CO)R^7$, $-NR^6(CO)OR^9$, $-NR^6(CO)NR^7R^8$, $-NR^6SO_2R^9$, $-COOR^6$, $-CONR^6R^7$, $-COR^6$, $-SO_2NR^6R^7$, $S(O)_{0-2}R^9$, $-O(CH_2)_{1-10}-COOR^6$, $-O(CH_2)_{1-10}CONR^6R^7$, -(lower alkylene)$COOR^6$ and $-CH=CH-COOR^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

$R^4$ is preferably 1-3 independently selected substituents, and $R^5$ is preferably 1-3 independently selected substituents.

Preferred compounds of Formula (VII) are those in which $Ar^1$ is phenyl or $R^4$-substituted phenyl, more preferably (4-$R^4$)-substituted phenyl. $Ar^2$ is preferably phenyl or $R^4$-substituted phenyl, more preferably (4-$R^4$)-substituted phenyl. $Ar^3$ is preferably $R^5$-substituted phenyl, more preferably (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or $-OR^6$ and $R^5$ is preferably $-OR^6$, wherein $R^6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably $-CH_2-$. $R^1$ and $R^3$ are each preferably hydrogen. R and $R^2$ are preferably $-OR^6$ wherein $R^6$ is hydrogen, or a group readily metabolizable to a hydroxyl (such as $-O(CO)R^6$, $-O(CO)OR^9$ and $-O(CO)NR^6R^7$, defined above).

The sum of m, n, p, q and r is preferably 2, 3 or 4, more preferably 3. Preferred are compounds wherein m, n and r are each zero, q is 1 and p is 2.

Also preferred are compounds of Formula (VII) wherein p, q and n are each zero, r is 1 and m is 2 or 3. More preferred are compounds wherein m, n and r are each zero, q is 1, p is 2, Z is $-CH_2-$ and R is $-OR^6$, especially when $R^6$ is hydrogen.

Also more preferred are compounds of Formula (VII) wherein p, q and n are each zero, r is 1, m is 2, X is $-CH_2-$ and $R^2$ is $-OR^6$, especially when $R^6$ is hydrogen.

Another group of preferred compounds of Formula (VII) are those wherein, $Ar^1$ is phenyl or $R^4$-substituted phenyl, $Ar^2$ is phenyl or $R^4$-substituted phenyl and $Ar^3$ is $R^5$-substituted phenyl. Also preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and the sum of m, n, p, q and r is 2, 3 or 4, more especially 3. More preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and wherein m, n and r are each zero, q is 1 and p is 2, or wherein p, q and n are each zero, r is 1 and m is 2 or 3.

In a preferred embodiment, a sterol absorption inhibitor and/or stanol absorption inhibitor of Formula (VII) useful in the compositions, combinations and methods of the present invention is represented by Formula (VIII) (ezetimibe) below:

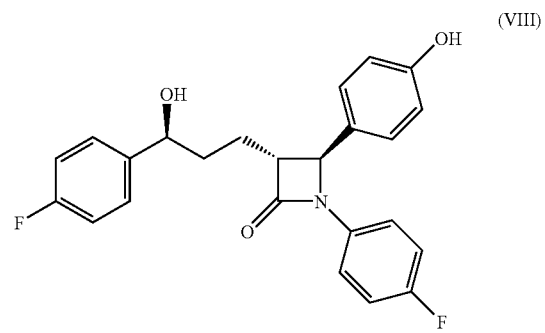

or pharmaceutically acceptable salts or solvates of the compounds of Formula (VIII), or prodrugs of the compound of Formula (VIII) or of the salts or solvates of the compound of Formula (VIII).

In another embodiment, one or more sterol absorption inhibitors and/or stanol absorption inhibitors useful in the methods, compositions or combinations of this invention are represented by Formula (IX):

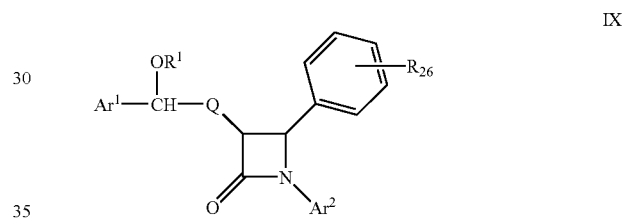

or isomers of the compounds of Formula (IX), or pharmaceutically acceptable salts or solvates of the compounds of Formula (IX) or of the isomers of the compounds of Formula (IX), or prodrugs of the compounds of Formula (IX) or of the isomers, salts or solvates of the compounds of Formula (IX), wherein in Formula (IX) above:

$R^{26}$ is selected from the group consisting of:

a) OH;

b) $OCH_3$;

c) fluorine and d) chlorine.

$R^1$ is selected from the group consisting of

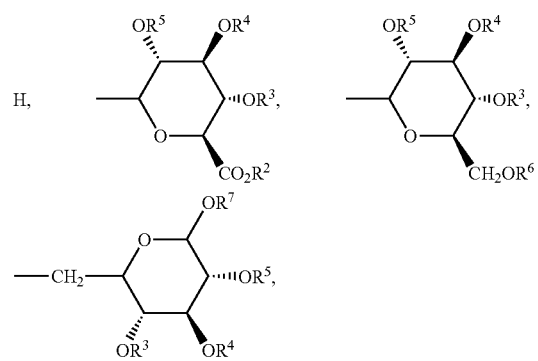

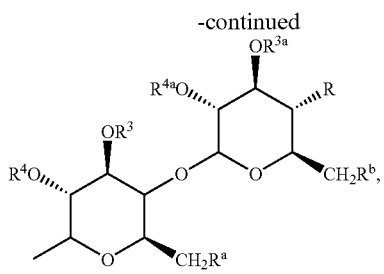

—SO₃H; natural and unnatural amino acids.

R, $R^a$ and $R^b$ are independently selected from the group consisting of H, —OH, halogeno, —NH₂, azido, ($C_1$-$C_6$) alkoxy($C_1$-$C_6$)-alkoxy and —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$-$C_6$)alkyl, aryl and aryl($C_1$-$C_6$)alkyl;

$R^3$, $R^4$, $R^5$, $R^7$, $R^{3a}$ and $R^{4a}$ are independently selected from the group consisting of H, ($C_1$-$C_6$)alkyl, aryl($C_1$-$C_6$) alkyl, —C(O)($C_1$-$C_6$)alkyl and —C(O)aryl;

$R^{30}$ is independently selected from the group consisting of $R^{32}$-substituted T, $R^{32}$-substituted-T-($C_1$-$C_6$)alkyl, $R^{32}$-substituted-($C_2$-$C_4$)alkenyl, $R^{32}$-substituted-($C_1$-$C_6$)alkyl, $R^{32}$-substituted-($C_3$-$C_7$)cycloalkyl and $R^{32}$-substituted-($C_3$-$C_7$) cycloalkyl($C_1$-$C_6$)alkyl;

$R^{31}$ is independently selected from the group consisting of H and ($C_1$-$C_4$)alkyl;

T is independently selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1-3 substituents independently selected from the group consisting of H, halogeno, ($C_1$-$C_4$)alkyl, —OH, phenoxy, —CF₃, —NO₂, ($C_1$-$C_4$) alkoxy, methylenedioxy, oxo, ($C_1$-$C_4$)alkylsulfanyl, ($C_1$-$C_4$) alkylsulfinyl, ($C_1$-$C_4$)alkylsulfonyl, —N(CH₃)₂, —C(O)—NH($C_1$-$C_4$)alkyl, —C(O)—N(($C_1$-$C_4$)alkyl)₂, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is —(CH₂)$_q$—, wherein q is 2-6, or, with the 3-position ring carbon of the azetidinone, forms the spiro group

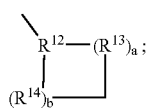

$R^{12}$ is

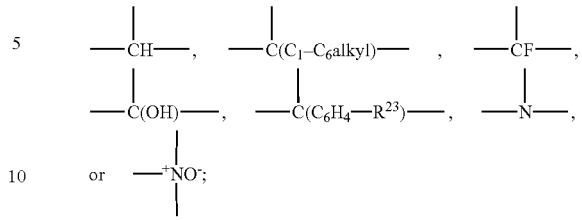

$R^{13}$ and $R^{14}$ are independently selected from the group consisting of —CH₂—, —CH($C_1$-$C_6$ alkyl)-, —C(di-($C_1$-$C_6$) alkyl), —CH=CH— and —C($C_1$-$C_6$ alkyl)=CH—; or $R^{12}$ together with an adjacent $R^{13}$, or $R^{12}$ together with an adjacent $R^{14}$, form a —CH=CH— or a —CH=C($C_1$-$C_6$ alkyl)- group;

a and b are independently 0, 1, 2 or 3, provided both are not zero; provided that when $R^{13}$ is —CH=CH— or —C($C_1$-$C_6$ alkyl)=CH—, a is 1; provided that when $R^{14}$ is —CH=CH— or —C($C_1$-$C_6$ alkyl)=CH—, b is 1; provided that when a is 2 or 3, the $R^{13}$'s can be the same or different; and provided that when b is 2 or 3, the $R^{14}$'s can be the same or different;

$R^{10}$ and $R^{11}$ are independently selected from the group consisting of 1-3 substituents independently selected from the group consisting of ($C_1$-$C_6$)alkyl, —OR$^{19}$, —O(CO)R$^{19}$, —O(CO)OR$^{21}$, —O(CH₂)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$ (CO)NR$^{20}$R$^{25}$, —NR$^{19}$SO₂R$^{21}$, —COOR$^{19}$, —CONR$^{19}$R$^{20}$, —COR$^{19}$, —SO₂NR$^{19}$R$^{20}$, S(O)$_{0-2}$R$^{21}$, —O(CH₂)$_{1-10}$—COOR$^{19}$, —O(CH₂)$_{1-10}$CONR$^{19}$R$^{20}$, —($C_1$-$C_6$ alkylene)—COOR$^{19}$, —CH=CH—COOR$^{19}$, —CF₃, —CN, —NO₂ and halogen;

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, ($C_1$-$C_6$)alkyl, aryl and aryl-substituted ($C_1$-$C_6$)alkyl;

$R^{21}$ is ($C_1$-$C_6$)alkyl, aryl or $R^{24}$-substituted aryl;

$R^{22}$ is H, ($C_1$-$C_6$)alkyl, aryl ($C_1$-$C_6$)alkyl, —C(O)R$^{19}$ or —COOR$^{19}$;

$R^{23}$ and $R^{24}$ are independently 1-3 groups independently selected from the group consisting of H, ($C_1$-$C_6$)alkyl, ($C_1$-$C_6$)alkoxy, —COOH, NO₂, —NR$^{19}$R$^{20}$, —OH and halogeno; and $R^{25}$ is H, —OH or ($C_1$-$C_6$)alkoxy.

$Ar^2$ is preferably phenyl or $R^{11}$-phenyl, especially (4-$R^{11}$)-substituted phenyl. Preferred definitions of $R^{11}$ are lower alkoxy, especially methoxy, and halogeno, especially fluoro.

$Ar^1$ is preferably phenyl or $R^{10}$-substituted phenyl, especially (4-$R^{10}$)-substituted phenyl. A preferred definition of $R^{10}$ is halogeno, especially fluoro.

Preferably Q is a lower alkyl or a spiro group as defined above, wherein preferably $R^{13}$ and $R^{14}$ are each ethylene and $R^{12}$ is

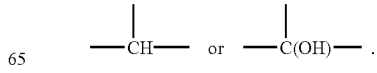

A preferred compound of formula IX, therefore, is one wherein $R^1$ is as defined above and in which the remaining variables have the following definitions:

$Ar^1$ is phenyl or $R^{10}$-substituted phenyl, wherein $R^{10}$ is halogeno;

$Ar^2$ is phenyl or $R^{11}$-phenyl, wherein $R^{11}$ is 1 to 3 substituents independently selected from the group consisting of $C_1$-$C_6$ alkoxy and halogeno;

Q is a lower alkyl (i.e. C-1 to C-2) with Q=C-2 being preferred, or Q, with the 3-position ring carbon of the azetidinone, forms the group

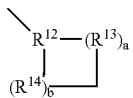

wherein preferably $R^{13}$ and $R^{14}$ are each ethylene and a and b are each 1, and wherein $R^{12}$ is

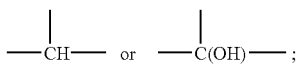

Preferred variables for $R^1$ groups of the formula

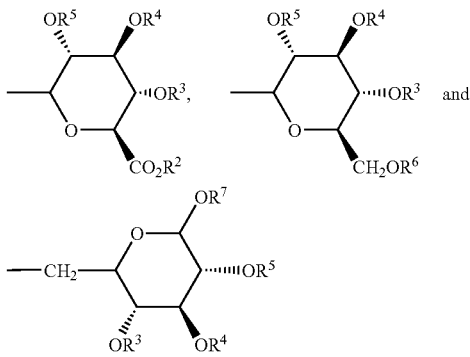

are as follows:

$R^2$, $R^3$, $R^4$, $R^5$, $R^6$ and $R^7$ are independently selected from the group consisting of H, ($C_1$-$C_6$)alkyl, benzyl and acetyl.

Preferred variables for group $R^1$ of the formula

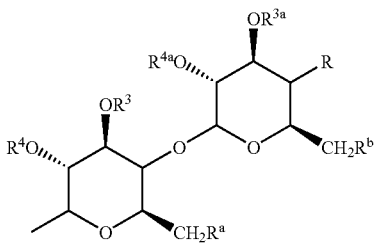

are as follows:

$R^3$, $R^{3a}$, $R^4$ and $R^{4a}$ are selected from the group consisting of H, ($C_1$-$C_6$)alkyl, benzyl and acetyl;

R, $R^a$ and $R^b$ are independently selected from the group consisting of H, —OH, halogeno, —NH$_2$, azido, ($C_1$-$C_6$) alkoxy($C_1$-$C_6$)alkoxy and —W—$R^{30}$, wherein W is —O—C(O)— or —O—C(O)—NR$^{31}$—, $R^{31}$ is H and $R^{30}$ is ($C_1$-$C_6$) alkyl, —C(O)—($C_1$-$C_4$)alkoxy-($C_1$-$C_6$)alkyl, T, T-($C_1$-$C_6$) alkyl, or T or T-($C_1$-$C_6$)alkyl wherein T is substituted by one or two halogeno or ($C_1$-$C_6$)alkyl groups.

Preferred $R^{30}$ substituents are 2-fluorophenyl, 2,4-difluoro-phenyl, 2,6-dichlorophenyl, 2-methylphenyl, 2-thienylmethyl, 2-methoxy-carbonylethyl, thiazol-2-yl-methyl, 2-furyl, 2-methoxycarbonylbutyl and phenyl. Preferred combinations of R, $R^a$ and $R^b$ are as follows: 1) R, $R^a$ and $R^b$ are independently —OH or —O—C(O)—NH—$R^{30}$, especially wherein $R^a$ is —OH and R and $R^b$ are —O—C(O)—NH—$R^{30}$ and $R^{30}$ is selected from the preferred substituents identified above, or wherein R and $R^a$ are —OH and $R^b$ is —O—C(O)—NH—$R^{30}$ wherein $R^{30}$ is 2-fluorophenyl, 2,4-difluorophenyl, 2,6-dichlorophenyl; 2) $R^a$ is —OH, halogeno, azido or ($C_1$-$C_6$)-alkoxy($C_1$-$C_6$)alkoxy, $R^b$ is H, halogeno, azido or ($C_1$-$C_6$)alkoxy($C_1$-$C_6$)-alkoxy, and R is —O—C(O)—NH—$R^{30}$, especially compounds wherein $R^a$ is —OH, $R^b$ is H and $R^{30}$ is 2-fluorophenyl; 3) R, $R^a$ and $R^b$ are independently —OH or —O—C(O)—$R^{30}$ and $R^{30}$ is ($C_1$-$C_6$)alkyl, T, or T substituted by one or two halogeno or ($C_1$-$C_6$)alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional classes of preferred are compounds are those wherein the $C^{1'}$ anomeric oxy is beta, wherein the $C^{2'}$ anomeric oxy is beta, and wherein the R group is alpha.

$R^1$ is preferably selected from:

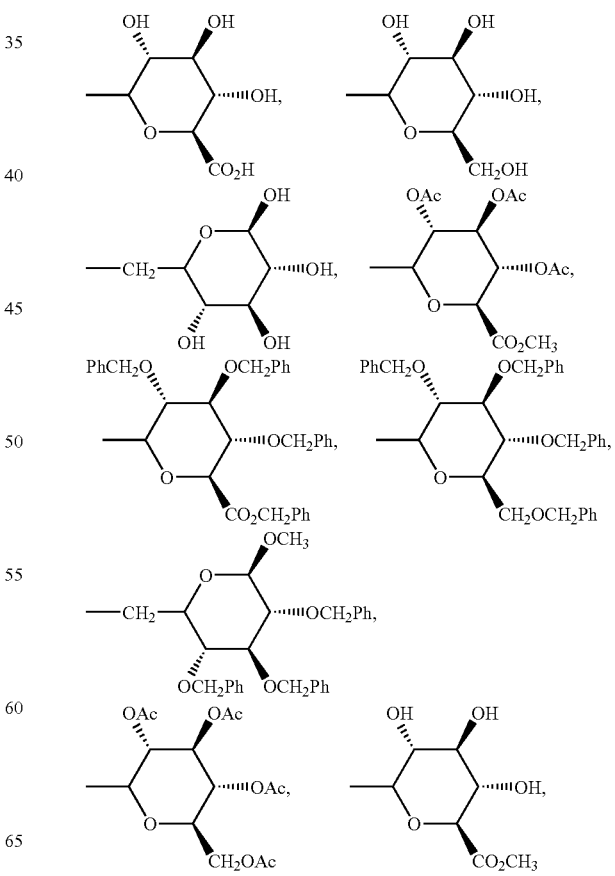

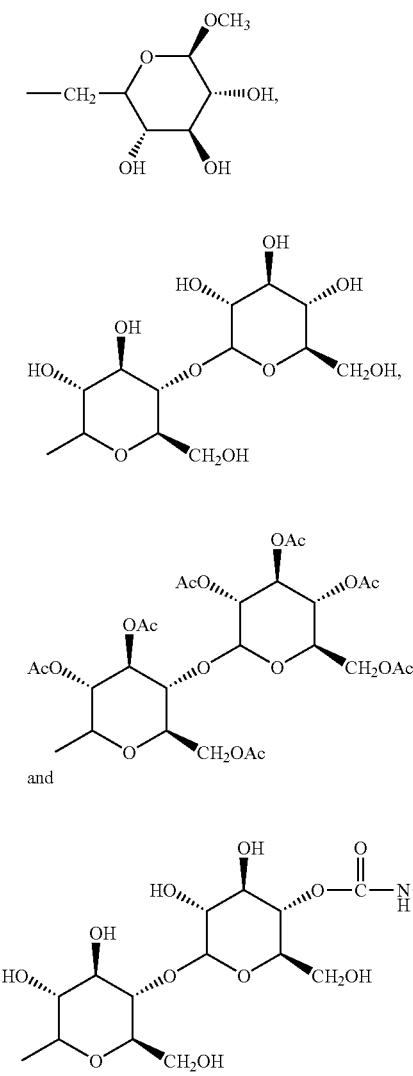

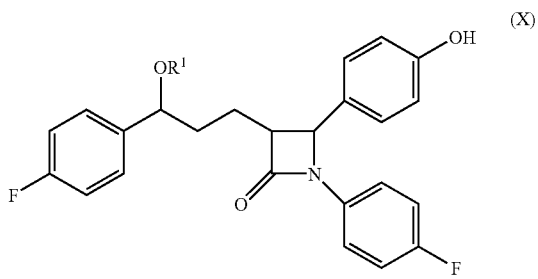

wherein Ac is acetyl and Ph is phenyl.

Thus a preferred compound of this invention is one represented by the Formula (X):

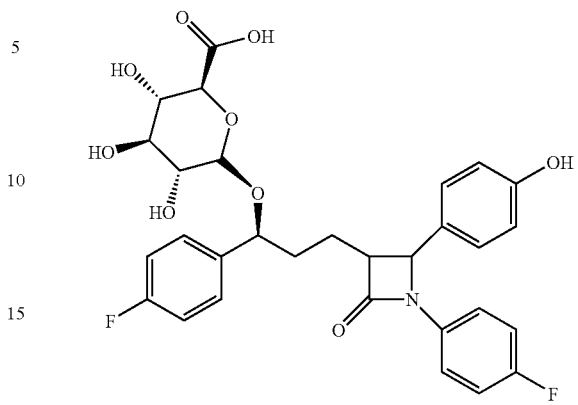

or pharmaceutically acceptable salts or solvates of the compound of Formula (X), or prodrugs of the compound of Formula (X) or of the salts or solvates of the compound of Formula (X), wherein $R^1$ is defined as above.

A more preferred compound is one represented by Formula (XI):

(XI)

or pharmaceutically acceptable salts or solvates of the compound of Formula (XI), or prodrugs of the compound of Formula (XI) or of the salts or solvates of the compound of Formula (XI).

Methods for making the compounds described above and other non-limiting examples of suitable compounds useful in the present invention are disclosed in U.S. Pat. Nos. 5,767,115; 5,846,966; 5,756,470, 5,698,548; 5,624,920; 5,656,624; 5,688,787; 5,688,990, 5,631,365, 6,207,822 and U.S. Provisional Patent Application No. 60/279,288 filed Mar. 28, 2001, each of which is incorporated herein by reference.

Generally, compounds of Formulae I-XI can be prepared by known methods, for example WO 93/02048 describes the preparation of compounds wherein —$R^1$-Q- is alkylene, alkenylene or alkylene interrupted by a hetero atom, phenylene or cycloalkylene; WO 94/17038 describes the preparation of compounds wherein Q is a spirocyclic group; WO 95/08532 describes the preparation of compounds wherein —$R^1$-Q- is a hydroxy-substituted alkylene group; PCT/US95/03196 describes compounds wherein —$R^1$-Q- is a hydroxy-substituted alkylene attached to the $Ar^1$ moiety through an —O— or $S(O)_{0-2}$— group; and U.S. Ser. No. 08/463,619, filed Jun. 5, 1995, describes the preparation of compounds wherein —$R^1$-Q- is a hydroxy-substituted alkylene group attached the azetidinone ring by a —$S(O)_{0-2}$— group, each of which is incorporated herein by reference.

As used herein, the term "alkyl" or "lower alkyl" means straight or branched alkyl chains of 1 to 6 carbon atoms and "alkoxy" similarly refers to alkoxy groups having 1 to 6 carbon atoms. Non-limiting examples of suitable lower alkyl groups include methyl, ethyl, propyl and butyl groups.

"Alkenyl" means straight or branched carbon chains having one or more double bonds in the chain, conjugated or unconjugated. Similarly, "alkynyl" means straight or branched carbon chains having one or more triple bonds in the chain. Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Aryl" means phenyl, naphthyl, indenyl, tetrahydronaphthyl or indanyl.

"Phenylene" means a bivalent phenyl group, including ortho, meta and para-substitution.

The statements wherein, for example, $R^{19}$, $R^{20}$ and $R^{25}$ are said to be independently selected from a group of substituents, means that $R^{19}$, $R^{20}$ and $R^{25}$ are independently selected, but also that where an $R^{19}$, $R^{20}$ or $R^{25}$ variable occurs more than once in a molecule, those occurrences are independently selected (e.g., if $R^{10}$ is —$OR^{19}$ wherein $R^{19}$ is hydrogen, $R^{11}$ can be —$OR^{19}$ wherein $R^{19}$ is lower alkyl). Those skilled in the art will recognize that the size and nature of the substituent(s) will affect the number of substituents which can be present.

Compounds of the invention have at least one asymmetrical carbon atom and therefore all isomers, including enantiomers, stereoisomers, rotamers, tautomers, racemates of the compounds of Formula (I-XI) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulae I-XI. Isomers may also include geometric isomers, e.g., when a double bond is present.

Those skilled in the art will appreciate that for some of the compounds of the Formulas I-XI, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

As used herein, "prodrug" means compounds that are drug precursors which, following administration to a patient, release the drug in vivo via some chemical or physiological process (e.g., a prodrug on being brought to the physiological pH or through enzyme action is converted to the desired drug form).

As used herein, "solvate" means a molecular or ionic complex of molecules or ions of solvent with those of solute (for example, one or more compounds of Formula I-XI, isomers of the compounds of Formula I-XI, and prodrugs of the compounds of Formula I-XI). Non-limiting examples of useful solvents include polar, protic solvents such as water and alcohols (for example methanol).

In an alternative embodiment, the treatment composition can further comprise one or more bile acid sequestrant(s) in coadministration with or in combination with one or more sterol absorption inhibitors.

Non-limiting examples of suitable bile acid sequestrants include cholestyramine (a styrene-divinylbenzene copolymer containing quaternary ammonium cationic groups capable of binding bile acids, such as QUESTRAN® or QUESTRAN LIGHT® which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

The bile acid sequestrant(s) are administered in a therapeutically effective amount to treat the specified condition, for example in a daily dose preferably ranging from about 1 to about 50 grams per day, and more preferably about 2 to about 16 grams per day, given in a single dose or 2-4 divided doses. The exact dose, however, is determined by the attending clinician and is dependent on such factors as the potency of the compound administered, the age, weight, condition and response of the patient.

In yet another alternative embodiment, the treatment composition can further comprise one or more lipid lowering agents such as, for example, sterol biosynthesis inhibitors, in coadministration with or in combination with one or more sterol absorption inhibitors.

Non-limiting lipid lowering agents for use in the treatment compositions of the present invention include HMG CoA reductase inhibitors such as lovastatin, pravastatin, fluvastatin, simvastatin, atorvastatin, rosuvastatin and itavastatin. Preferred HMG CoA reductase inhibitors include lovastatin, atorvastatin and simvastatin. The most preferred HMG CoA reductase inhibitors are atorvastatin and simvastatin.

In another preferred embodiment, the treatment composition comprises the compound of Formula (VIII) in combination with a bile acid sequestrant. In this embodiment, preferably the bile acid sequestrant is selected from cholestyramine, colesevelam hydrochloride and colestipol. Preferably, the treatment composition comprises one or more bile acid sequestrants such as, for example, cholestyramine, colesevelam hydrochloride and colestipol in combination with a compound of Formula (VIII)

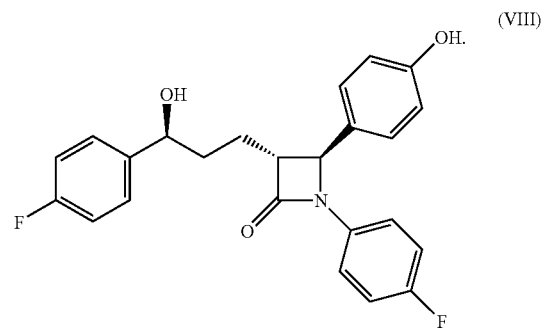

(VIII)

In another preferred embodiment, the treatment composition comprises the compound of Formula (VIII) in combination with another lipid lowering agent. In this embodiment, preferably the lipid lowering agent comprises one or more HMG CoA reductase inhibitors. Preferably, the treatment composition comprises one or more HMG CoA reductase inhibitors such as, for example, lovastatin, atorvastatin and simvastatin in combination with a compound of Formula (VIII)

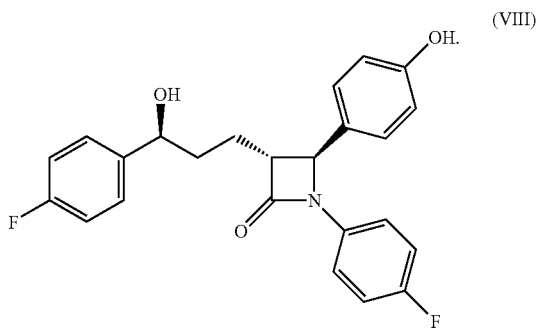

Still even more preferred, the treatment composition comprises compound of formula VIII in combination with atorvastatin and/or simvastatin.

In one embodiment of the invention, the compositions or therapeutic combinations can further comprise one or more pharmacological or therapeutic agents or drugs such as cholesterol biosynthesis inhibitors and/or lipid-lowering agents discussed below.

Also useful with the invention are compositions or therapeutic combinations that can further comprise at least one (one or more) activators for peroxisome proliferator-activated receptors (PPAR). The activators act as agonists for the peroxisome proliferator-activated receptors. Three subtypes of PPAR have been identified, and these are designated as peroxisome proliferator-activated receptor alpha (PPAR), peroxisome proliferator-activated receptor gamma (PPAR) and peroxisome proliferator-activated receptor delta (PPAR). It should be noted that PPAR is also referred to in the literature as PPAR and as NUC1, and each of these names refers to the same receptor.

PPAR regulates the metabolism of lipids. PPAR is activated by fibrates and a number of medium and long-chain fatty acids, and it is involved in stimulating -oxidation of fatty acids. The PPAR receptor subtypes are involved in activating the program of adipocyte differentiation and are not involved in stimulating peroxisome proliferation in the liver. PPAR has been identified as being useful in increasing high density lipoprotein (HDL) levels in humans. See, e.g., WO 97/28149.

PPAR activator compounds are useful for, among other things, lowering triglycerides, moderately lowering LDL levels and increasing HDL levels. Useful examples of PPAR activators include fibric acid derivatives or fibrates.

Non-limiting examples of suitable fibric acid derivatives ("fibrates") include clofibrate (such as ethyl 2-(p-chlorophenoxy)-2-methyl-propionate, for example ATROMID-S® Capsules which are commercially available from Wyeth-Ayerst); gemfibrozil (such as 5-(2,5-dimethylphenoxy)-2,2-dimethylpentanoic acid, for example LOPID® tablets which are commercially available from Parke Davis); ciprofibrate (C.A.S. Registry No. 52214-84-3, see U.S. Pat. No. 3,948, 973 which is incorporated herein by reference); bezafibrate (C.A.S. Registry No. 41859-67-0, see U.S. Pat. No. 3,781, 328 which is incorporated herein by reference); clinofibrate (C.A.S. Registry No. 30299-08-2, see U.S. Pat. No. 3,716, 583 which is incorporated herein by reference); binifibrate (C.A.S. Registry No. 69047-39-8, see BE 884722 which is incorporated herein by reference); lifibrol (C.A.S. Registry No. 96609-16-4); fenofibrate (such as TRICOR® micronized fenofibrate (2-[4-(4-chlorobenzoyl)phenoxy]-2-methyl-propanoic acid, 1-methylethyl ester) which is commercially available from Abbott Laboratories or LIPANTHYL® micronized fenofibrate which is commercially available from Labortoire Founier, France) and mixtures thereof. These compounds can be used in a variety of forms, including but not limited to acid form, salt form, racemates, enantiomers, zwitterions and tautomers.

Other examples of PPAR activators useful with the practice of the present invention include suitable fluorophenyl compounds as disclosed in U.S. Pat. No. 6,028,109 which is incorporated herein by reference; certain substituted phenyl-propionic compounds as disclosed in WO 00/75103 which is incorporated herein by reference; and PPAR activator compounds as disclosed in WO 98/43081 which is incorporated herein by reference.

Non-limiting examples of suitable PPAR activators include derivatives of glitazones or thiazolidinediones, such as, troglitazone (such as REZULIN® troglitazone (-5-[[4-[3, 4-dihydro-6-hydroxy-2,5,7,8-tetramethyl-2H-1-benzopyran-2-yl]methoxy]phenyl]methyl]-2,4-thiazolidinedione) commercially available from Parke-Davis); rosiglitazone (such as AVANDIA® rosiglitazone maleate (-5-[[4-[2-(methyl-2-pyridinylamino)ethoxy]phenyl]methyl]-2,4-thiazolidinedione, (Z)-2-butenedioate) commercially available from SmithKline Beecham) and pioglitazone (such as ACTOS™ pioglitazone hydrochloride (5-[[4-[2-(5-ethyl-2-pyridinyl)ethoxy]phenyl]methyl]-2,4-thiazolidinedione monohydrochloride) commercially available from Takeda Pharmaceuticals). Other useful thiazolidinediones include ciglitazone, englitazone, darglitazone and BRL 49653 as disclosed in WO 98/05331 which is incorporated herein by reference; PPAR activator compounds disclosed in WO 00/76488 which is incorporated herein by reference; and PPARy activator compounds disclosed in U.S. Pat. No. 5,994, 554 which is incorporated herein by reference.

Other useful PPAR activator compounds include certain acetylphenols as disclosed in U.S. Pat. No. 5,859,051 which is incorporated herein by reference; certain quinoline phenyl compounds as disclosed in WO 99/20275 which is incorporated herein by reference; aryl compounds as disclosed by WO 99/38845 which is incorporated herein by reference; certain 1,4-disubstituted phenyl compounds as disclosed in WO 00/63161; certain aryl compounds as disclosed in WO 01/00579 which is incorporated herein by reference; benzoic acid compounds as disclosed in WO 01/12612 and WO 01/12187 which are incorporated herein by reference; and substituted 4-hydroxy-phenylalconic acid compounds as disclosed in WO 97/31907 which is incorporated herein by reference.

PPAR compounds are useful for, among other things, lowering triglyceride levels or raising HDL levels. Non-limiting examples of PPAR activators include suitable thiazole and oxazole derivates, such as C.A.S. Registry No. 317318-32-4, as disclosed in WO 01/00603 which is incorporated herein by reference); certain fluoro, chloro or thio phenoxy phenylacetic acids as disclosed in WO 97/28149 which is incorporated herein by reference; suitable non-β-oxidizable fatty acid analogues as disclosed in U.S. Pat. No. 5,093,365 which is incorporated herein by reference; and PPAR compounds as disclosed in WO 99/04815 which is incorporated herein by reference.

Moreover, compounds that have multiple functionality for activating various combinations of PPAR, PPAR and PPAR are also useful with the practice of the invention. Non-limiting examples include certain substituted aryl compounds as disclosed in U.S. Pat. No. 6,248,781; WO 00/23416; WO 00/23415; WO 00/23425; WO 00/23445; WO 00/23451; and WO 00/63153, all of which are incorporated herein by reference, are described as being useful PPAR and/or PPAR activator compounds. Other non-limiting examples of useful PPAR and/or PPAR activator compounds include activator compounds as disclosed in WO 97/25042 which is incorporated herein by reference; activator compounds as disclosed in WO 00/63190 which is incorporated herein by reference; activator compounds as disclosed in WO 01/21181 which is incorporated herein by reference; biaryl-oxa(thia)zole compounds as disclosed in WO 01/16120 which is incorporated herein by reference; compounds as disclosed in WO 00/63196 and WO 00/63209 which are incorporated herein by reference; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G which are incorporated herein by reference; GW2331 or (2-(4-[difluorophenyl]-1heptylureido)ethyl]phenoxy)-2-methylbutyric compounds as disclosed in WO 98/05331 which is incorporated herein by reference; aryl compounds as disclosed in U.S. Pat. No. 6,166,049 which is incorporated herein by reference; oxazole compounds as disclosed in WO 01/17994 which is incorporated herein by reference; and dithiolane compounds as disclosed in WO 01/25225 and WO 01/25226 which are incorporated herein by reference.

Other useful PPAR activator compounds include substituted benzylthiazolidine-2,4-dione compounds as disclosed in WO 01/14349, WO 01/14350 and WO/01/04351 which are incorporated herein by reference; mercaptocarboxylic compounds as disclosed in WO 00/50392 which is incorporated herein by reference; ascofuranone compounds as disclosed in WO 00/53563 which is incorporated herein by reference; carboxylic compounds as disclosed in WO 99/46232 which is incorporated herein by reference; compounds as disclosed in WO 99/12534 which is incorporated herein by reference; benzene compounds as disclosed in WO 99/15520 which is incorporated herein by reference; o-anisamide compounds as disclosed in WO 01/21578 which is incorporated herein by reference; and PPAR activator compounds as disclosed in WO 01/40192 which is incorporated herein by reference.

The peroxisome proliferator-activated receptor(s) activator(s) are administered in a therapeutically effective amount to treat the specified condition, for example in a daily dose preferably ranging from about 50 to about 3000 mg per day, and more preferably about 50 to about 2000 mg per day, given in a single dose or 24 divided doses. The exact dose, however, is determined by the attending clinician and is dependent on such factors as the potency of the compound administered, the age, weight, condition and response of the patient.

In an alternative embodiment, the compositions or therapeutic combinations of the invention can further comprise one or more ileal bile acid transport ("IBAT") inhibitors (or apical sodium co-dependent bile acid transport ("ASBT") inhibitors) coadministered with or in combination with the sterol absorption inhibitor(s) discussed above. The IBAT inhibitors can inhibit bile acid transport to reduce LDL cholesterol levels. Non-limiting examples of suitable IBAT inhibitors include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference.

Generally, a total daily dosage of IBAT inhibitor(s) can range from about 0.01 to about 1000 mg/day, and preferably about 0.1 to about 50 mg/day in single or 2-4 divided doses.

In another alternative embodiment, the compositions or therapeutic combinations of the invention can further comprise nicotinic acid (niacin) and/or derivatives thereof coadministered with or in combination with the sterol absorption inhibitor(s) discussed above.

As used herein, "nicotinic acid derivative" means a compound comprising a pyridine-3-carboxylate structure or a pyrazine-2-carboxylate structure, including acid forms, salts, esters, zwitterions and tautomers, where available. Examples of nicotinic acid derivatives include niceritrol, nicofuranose and acipimox (5-methyl pyrazine-2-carboxylic acid 4-oxide). Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos.

Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

In another alternative embodiment, the compositions or therapeutic combinations of the invention can further comprise one or more AcylCoA:Cholesterol O-acyltransferase ("ACAT") Inhibitors, which can reduce LDL and VLDL levels, coadministered with or in combination with the sterol absorption inhibitor(s) discussed above. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors include avasimibe ([[2,4,6-tris(1-methylethyl)phenyl]acetyl]sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea). See P. Chang et al., "Current, New and Future Treatments in Dyslipidaemia and Atherosclerosis", *Drugs* 2000 July;60(1); 55-93, which is incorporated by reference herein.

Generally, a total daily dosage of ACAT inhibitor(s) can range from about 0.1 to about 1000 mg/day in single or 2-4 divided doses.

In another alternative embodiment, the compositions or therapeutic combinations of the invention can further comprise one or more Cholesteryl Ester Transfer Protein ("CETP") Inhibitors coadministered with or in combination with the sterol absorption inhibitor(s) discussed above. CETP is responsible for the exchange or transfer of cholesteryl ester carrying HDL and triglycerides in VLDL.

Non-limiting examples of suitable CETP inhibitors are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be coadministered with or in combination with the peroxisome proliferator-activated receptor(s) activator and sterol absorption inhibitor(s) discussed above.

Generally, a total daily dosage of CETP inhibitor(s) can range from about 0.01 to about 1000 mg/day, and preferably about 0.5 to about 20 mg/kg body weight/day in single or divided doses.

In another alternative embodiment, the compositions or therapeutic combinations of the invention can further comprise probucol or derivatives thereof (such as AGI-1067 and other derivatives disclosed in U.S. Pat. Nos. 6,121,319 and 6,147,250), which can reduce LDL levels, coadministered with or in combination with the sterol absorption inhibitor(s) discussed above.

Generally, a total daily dosage of probucol or derivatives thereof can range from about 10 to about 2000 mg/day, and preferably about 500 to about 1500 mg/day in single or 2-4 divided doses.

In another alternative embodiment, the compositions or treatments of the invention can further comprise low-density lipoprotein (LDL) receptor activators, coadministered with or in combination with the sterol absorption inhibitor(s) discussed above. Non-limiting examples of suitable LDL-receptor activators include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", Arterioscler. Thromb. 1993; 13:1005-12.

Generally, a total daily dosage of LDL receptor activator(s) can range from about 1 to about 1000 mg/day in single or 2-4 divided doses.

In another alternative embodiment, the compositions or therapeutic combinations of the invention can further comprise fish oil, which contains Omega 3 fatty acids (3-PUFA), which can reduce VLDL and triglyceride levels, coadministered with or in combination with sterol absorption inhibitor(s) discussed above. Generally, a total daily dosage of fish oil or Omega 3 fatty acids can range from about 1 to about 30 grams per day in single or 2-4 divided doses.

In another alternative embodiment, the compositions or therapeutic combinations of the invention can further comprise natural water soluble fibers, such as psyllium, guar, oat and pectin, which can reduce cholesterol levels, coadministered with or in combination with the sterol absorption inhibitor(s) discussed above. Generally, a total daily dosage of natural water soluble fibers can range from about 0.1 to about 10 grams per day in single or 2-4 divided doses.

In another alternative embodiment, the compositions or therapeutic combinations of the invention can further comprise plant sterols, plant stanols and/or fatty acid esters of plant stanols, such as sitostanol ester used in BENECOL® margarine, which can reduce cholesterol levels, coadministered with or in combination with the sterol absorption inhibitor(s) discussed above. Generally, a total daily dosage of plant sterols, plant stanols and/or fatty acid esters of plant stanols can range from about 0.5 to about 20 grams per day in single or 2-4 divided doses.

In another alternative embodiment, the compositions or therapeutic combinations of the invention can further comprise antioxidants, such as probucol, tocopherol, ascorbic acid, β-carotene and selenium, or vitamins such as vitamin $B_6$ or vitamin $B_{12}$, coadministered with or in combination with the sterol absorption inhibitor(s) discussed above. Generally, a total daily dosage of antioxidants or vitamins can range from about 0.05 to about 10 grams per day in single or 2-4 divided doses.

In another alternative embodiment, the compositions or therapeutic combinations of the invention can further comprise monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E, coadministered with or in combination with the sterol absorption inhibitor(s) discussed above. Generally, a total daily dosage of these agents can range from about 0.01 to about 1000 mg/day in single or 2-4 divided doses.

Also useful with the invention are compositions or therapeutic combinations which further comprise hormone replacement agents and compositions. Useful hormone agents and compositions for hormone replacement therapy of the present invention include androgens, estrogens, progestins, their pharmaceutically acceptable salts and derivatives thereof. Combinations of these agents and compositions are also useful.

The dosage of androgen and estrogen combinations vary, desirably from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone (17-hydroxy-17-methyl-, (17B)-androst-4-en-3-one) available from Solvay Pharmaceuticals, Inc., Marietta, Ga., under the tradename Estratest.

Estrogens and estrogen combinations may vary in dosage from about 0.01 mg up to 8 mg, desirably from about 0.3 mg to about 3.0 mg. Examples of useful estrogens and estrogen combinations include:

(a) the blend of nine (9) synthetic estrogenic substances including sodium estrone sulfate, sodium equilin sulfate, sodium 17-dihydroequilin sulfate, sodium 17-estradiol sulfate, sodium 17-dihydroequilin sulfate, sodium 17-dihydroequilenin sulfate, sodium 17-dihydroequilenin sulfate, sodium equilenin sulfate and sodium 17-estradiol sulfate; available from Duramed Pharmaceuticals, Inc., Cincinnati, Ohio, under the tradename Cenestin;

(b) ethinyl estradiol (19-nor-17-pregna-1,3,5(10)-trien-20-yne-3,17-diol; available by Schering Plough Corporation, Kenilworth, N.J., under the tradename Estinyl;

(c) esterified estrogen combinations such as sodium estrone sulfate and sodium equilin sulfate; available from Solvay under the tradename Estratab and from Monarch Pharmaceuticals, Bristol, Tenn., under the tradename Menest;

(d) estropipate (piperazine estra-1,3,5(10)-trien-17-one, 3-(sulfooxy)-estrone sulfate); available from Pharmacia & Upjohn, Peapack, N.J., under the tradename Ogen and from Women First Health Care, Inc., San Diego, Calif., under the tradename Ortho-Est; and (e) conjugated estrogens (17-dihydroequilin, 17-estradiol, and 17-dihydroequilin); available from Wyeth-Ayerst Pharmaceuticals, Philadelphia, Pa., under the tradename Premarin.

Progestins and estrogens may also be administered with a variety of dosages, generally from about 0.05 to about 2.0 mg progestin and about 0.001 mg to about 2 mg estrogen, desirably from about 0.1 mg to about 1 mg progestin and about 0.01 mg to about 0.5 mg estrogen. Examples of progestin and estrogen combinations that may vary in dosage and regimen include:

(a) the combination of estradiol (estra-1,3,5(10)-triene-3, 17-diol hemihydrate) and norethindrone (17-acetoxy-19-nor-17-pregn-4-en-20-yn-3-one); which is available from Pharmacia & Upjohn, Peapack, N.J., under the tradename Activella;

(b) the combination of levonorgestrel (d(−)-13-ethyl-17-ethinyl-17-hydroxygon-4-en-3-one) and ethinyl estradial;

available from Wyeth-Ayerst under the tradename Alesse, from Watson Laboratories, Inc., Corona, Calif., under the tradenames Levora and Trivora, Monarch Pharmaceuticals, under the tradename Nordette, and from Wyeth-Ayerst under the tradename Triphasil;

(c) the combination of ethynodiol diacetate (19-nor-17-pregn-4-en-20-yne-3,17-diol diacetate) and ethinyl estradiol; available from G.D. Searle & Co., Chicago, Ill., under the tradename Demulen and from Watson under the tradename Zovia;

(d) the combination of desogestrel (13-ethyl-11-methylene-18,19-dinor-17-pregn-4-en-20-yn-17-ol) and ethinyl estradiol; available from Organon under the tradenames Desogen and Mircette, and from Ortho-McNeil Pharmaceutical, Raritan, N.J., under the tradename Ortho-Cept;

(e) the combination of norethindrone and ethinyl estradiol; available from Parke-Davis, Morris Plains, N.J., under the tradenames Estrostep and femhrt, from Watson under the tradenames Microgestin, Necon, and Tri-Norinyl, from Ortho-McNeil under the tradenames Modicon and Ortho-Novum, and from Warner Chilcott Laboratories, Rockaway, N.J., under the tradename Ovcon;

(f) the combination of norgestrel ((±)-13-ethyl-17-hydroxy-18,19-dinor-17-preg-4-en-20-yn-3-one) and ethinyl estradiol; available from Wyeth-Ayerst under the tradenames Ovral and Lo/Ovral, and from Watson under the tradenames Ogestrel and Low-Ogestrel;

(g) the combination of norethindrone, ethinyl estradiol, and mestranol (3-methoxy-19-nor-17-pregna-1,3,5(10)-trien-20-yn-17-ol); available from Watson under the tradenames Brevicon and Norinyl;

(h) the combination of 17-estradiol(estra-1,3,5(10)-triene-3,17-diol) and micronized norgestimate (17-17-(Acetyloxyl)-13-ethyl-18,19-dinorpregn-4-en-20-yn-3-one3-oxime); available from Ortho-McNeil under the tradename Ortho-Prefest;

(i) the combination of norgestimate (18,19-dinor-17-pregn-4-en-20-yn-3-one, 17-(acetyloxy)-13-ethyl-,oxime, (17( )-(+)-) and ethinyl estradiol; available from Ortho-McNeil under the tradenames Ortho Cyclen and Ortho Tri-Cyclen; and (j) the combination of conjugated estrogens (sodium estrone sulfate and sodium equilin sulfate) and medroxyprogesterone acetate (20-dione, 17-(acetyloxy)-6-methyl-, (6( ))-pregn-4-ene-3); available from Wyeth-Ayerst under the tradenames Premphase and Prempro.

In general, a dosage of progestins may vary from about 0.05 mg to about 10 mg or up to about 200 mg if microsized progesterone is administered. Examples of progestins include norethindrone; available from ESI Lederle, Inc., Philadelphia, Pa., under the tradename Aygestin, from Ortho-McNeil under the tradename Micronor, and from Watson under the tradename Nor-QD; norgestrel; available from Wyeth-Ayerst under the tradename Ovrette; micronized progesterone (pregn-4-ene-3,20-dione); available from Solvay under the tradename Prometrium; and medroxyprogesterone acetate; available from Pharmacia & Upjohn under the tradename Provera.

The compositions, therapeutic combinations or methods of the invention can further comprise one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxtine); thermogenic agents (such as ephedrine, caffeine, theophylline, and selective 3-adrenergic agonists); alpha-blocking agents; kainite or AMPA receptor antagonists; leptin-lipolysis stimulated receptors; phosphodiesterase enzyme inhibitors; compounds having nucleotide sequences of the mahogany gene; fibroblast growth factor-10 polypeptides; monoamine oxidase inhibitors (such as befloxatone, moclobemide, brofaromine, phenoxathine, esuprone, befol, toloxatone, pirlindol, amiflamine, sercloremine, bazinaprine, lazabemide, milacemide and caroxazone); compounds for increasing lipid metabolism (such as evodiamine compounds); and lipase inhibitors (such as orlistat). Generally, a total dosage of the above-described obesity control medications can range from 1 to 3,000 mg/day, desirably from about 1 to 1,000 mg/day and more desirably from about 1 to 200 mg/day in single or 2-4 divided doses.

The compositions, therapeutic combinations or methods of the invention can further comprise one or more blood modifiers which are chemically different from the substituted azetidinone and substituted β-lactam compounds discussed above. Useful blood modifiers include but are not limited to anti-coagulants (argatroban, bivalirudin, dalteparin sodium, desirudin, dicumarol, lyapolate sodium, nafamostat mesylate, phenprocoumon, tinzaparin sodium, warfarin sodium); antithrombotic (anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab, zolimomab aritox); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate, epoprostenol, epoprostenol sodium, ticlopidine hydrochloride, aspirin, ibuprofen, naproxen, sulindae, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitors; Factor VIIa inhibitors (4H-31-benzoxazin-4-ones, 4H-3,1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl}amide trifluoroacetate, dibenzofuran-2-sulfonic acid {1-[3-(aminomethyl)-benzyl]-5-oxo-pyrrolidin-3-yl}-amide, tolulene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate); Factor Xa inhibitors (disubstituted pyrazolines, disubstituted triazolines, substituted n-[(aminoiminomethyl)phenyl]propylamides, substituted n-[(aminomethyl)phenyl]propylamides, tissue factor pathway inhibitor (TFPI), low molecular weight heparins, heparinoids, benzimidazolines, benzoxazolinones, benzopiperazinones, indanones, dibasic (amidinoaryl) propanoic acid derivatives, amidinophenyl-pyrrolidines, amidinophenyl-pyrrolines, amidinophenyl-isoxazolidines, amidinoindoles, amidinoazoles, bis-arlysulfonylaminobenzamide derivatives, peptidic Factor Xa inhibitors).

The compositions, therapeutic combinations or methods of the invention can further comprise one or more cardiovascular agents which are chemically different from the substituted azetidinone and substituted β-lactam compounds (such as compounds I-XI above) discussed above. Useful cardiovascular agents include but are not limited to calcium channel blockers (clentiazem maleate, amlodipine besylate, isradipine, nimodipine, felodipine, nilvadipine, nifedipine, teludipine hydrochloride, diltiazem hydrochloride, belfosdil, verapamil hydrochloride, fostedil); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate, nebivolol); adrenergic stimulants; angiotensin converting enzyme (ACE) inhibitors (benazepril hydrochloride, benazeprilat, captopril, delapril hydrochloride, fosinopril sodium, libenzapril, moexipril hydrochloride, pentopril, perindopril, quinapril hydrochloride, quinaprilat, ramipril, spirapril hydrochloride, spiraprilat, teprotide, enalapril maleate, lisinopril, zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate, bevantolol hydrochloride); angiotensin II receptor antagonists (candesartan, irbesartan, losartan potassium, candesartan cilexetil, telmisartan); anti-anginal agents (amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochoride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexiline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the invention can further comprise one or more antidiabetic medications for reducing blood glucose levels in a human. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguanide (such as metformin and buformin), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 2-4 divided doses.

Mixtures of any of the pharmacological or therapeutic agents described above can be used in the compositions and therapeutic combinations of the invention.

The treatment compositions of the invention generally additionally comprise a pharmaceutically acceptable carrier diluent, excipient or carrier (collectively referred to herein as carrier materials). Because of their sterol absorption inhibitory activity, such pharmaceutical compositions possess utility in treating sitosterolemia and related disorders.

In the treatment compositions used in the methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethyl-cellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. sterol absorption inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The pharmaceutical treatment compositions of the present invention can be administered to a mammal in need of such treatment in a pharmaceutically or therapeutically effective amount to treat sitosterolemia and/or reduce the level of sterol(s) in the plasma and tissues.

The term "therapeutically effective amount" means that amount of a therapeutic agent of the composition, such as the bile acid sequestrant(s), sterol absorption inhibitor(s) and other pharmacological or therapeutic agents described below, that will elicit a biological or medical response of a tissue, system, animal or mammal that is being sought by the administrator (such as a researcher, doctor or veterinarian) which includes alleviation of the symptoms of the sitosterolemic condition or disease being treated and the prevention, slowing or halting of progression of the sitosterolemic condition, reduction of the concentration of sterol(s) and/or 5α-stanol(s) in the plasma and/or tissues, and/or preventing or reducing the risk of the occurrence of a biological or medical event (such as a coronary event).

As used herein, "combination therapy" or "therapeutic combination" means the administration of two or more therapeutic agents, such as sterol absorption inhibitor(s) and bile acid sequestrant(s) or other therapeutic vascular agents, to prevent or treat sitosterolemia and/or reduce the level of sterol(s) in the plasma and tissues. As used herein, "vascular" comprises cardiovascular, cerebrovascular and combinations thereof. Such administration includes coadministration of these therapeutic agents in a substantially simultaneous manner, such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating the sitosterolemic condition and/or reduce the level of sterol(s) in the plasma and tissues. A potential advantage of the combination therapy disclosed herein may be a reduction in the required amount of an individual therapeutic compound or the overall total amount of therapeutic compounds that are effective in treating the sitosterolemic condition and/or reducing the level of sterol(s) in the plasma and tissues. Therapeutic agents can be selected to provide a broader range of complementary effects or complimentary modes of action.

The daily dose of the sterol absorption inhibitor(s) preferably ranges from about 0.1 to about 30 mg/kg of body weight per day, and more preferably about 0.1 to about 15 mg/kg. For an average body weight of 70 kg, the dosage level therefore ranges from about 1 mg to about 1000 mg of sterol absorption inhibitor(s) per day, given in a single dose or 2-4 divided doses. The exact dose, however, is determined by the attending clinician and is dependent on the potency of the compound administered, the age, weight, condition and response of the patient.

For the pharmaceutical treatment compositions of the present invention in which the sterol absorption inhibitor(s) is administered concomitantly or in combination with a bile acid sequestrant, the typical daily dose of the sequestrant preferably ranges from about 0.1 to about 80 mg/kg of body weight per day administered in single or divided dosages, usually once or twice a day. For example, preferably about 10 to about 40 mg per dose is given 1 to 2 times a day, giving a total daily dose of about 10 to about 80 mg per day. The exact dose of sterol absorption inhibitor(s) and bile acid sequestrant(s) to be administered is determined by the attending clinician and is dependent on the potency of the compound administered, the age, weight, condition and response of the patient.

Where the sterol absorption inhibitor(s) and bile acid sequestrant(s) are administered in separate dosages, the number of doses of each component given per day may not necessarily be the same, e.g., one component may have a greater duration of activity and will therefore need to be administered less frequently.

For the pharmaceutical treatment compositions of the present invention in which the sterol absorption inhibitor(s) is administered concomitantly or in combination with a lipid lowering agent, the typical daily dose of the lipid lowering agent preferably ranges from about 0.1 to about 80 mg/kg of body weight per day administered in single or divided dosages, usually once or twice a day. For example, for HMG CoA reductase inhibitors, preferably about 10 to about 40 mg per dose is given 1 to 2 times a day, giving a total daily dose of about 10 to about 80 mg per day. For other lipid lowering agents, preferably about 1 to about 1000 mg per dose is given 1 to 2 times a day, giving a total daily dose ranging from about 1 mg to about 2000 mg per day. The exact dose of sterol absorption inhibitor(s) and lipid lowering agent(s) to be administered is determined by the attending clinician and is dependent on the potency of the compound administered, the age, weight, condition and response of the patient.

Where the sterol absorption inhibitor(s) and lipid lowering agent(s) are administered in separate dosages, the number of doses of each component given per day may not necessarily be the same, e.g., one component may have a greater duration of activity and will therefore need to be administered less frequently.

The formulations and pharmaceutical compositions can be prepared using conventional pharmaceutically acceptable and conventional techniques. The following formulations exemplify some of the dosage forms of this invention. In each formulation, the term "active compound" designates a substituted azetidinone compound, a β-lactam compound or a compound of any of Formulae I-XI described herein above.

EXAMPLE A

| No. | Ingredient | mg/tablet | mg/tablet |
|---|---|---|---|
| | Tablets | | |
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weight on a suitable tablet machine.

EXAMPLE B

| No. | Ingredient | mg/tablet | mg/tablet |
|---|---|---|---|
| | Capsules | | |
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

EXAMPLE C

| No. | Ingredient | mg/tablet |
|---|---|---|
| | Tablets | |
| 1 | Active Compound I | 10 |
| 2 | Lactose monohydrate NF | 55 |
| 3 | Microcrystalline cellulose NF | 20 |
| 4 | Povidone (K29–32) USP | 4 |
| 5 | Croscarmellose sodium NF | 8 |
| 6 | Sodium lauryl sulfate | 2 |
| 7 | Magnesium stearate NF | 1 |
| | Total | 100 |

Method of Manufacture

Mix Item No. 4 with purified water in suitable mixer to form binder solution. Spray the binder solution and then water over Items 1, 2, 6 and a portion of Item 5 in a fluidized bed processor to granulate the ingredients. Continue fluidization to dry the damp granules. Screen the dried granules and blend with Item No. 3 and the remainder of Item 5. Add Item No. 7 and mix. Compress the mixture to appropriate size and weight on a suitable tablet machine.

In the present invention, the above-described tablet can be coadministered with a tablet, capsule, etc. comprising a dosage of another therapeutic agent such as are described above, for example a bile acid sequestrant as described above.

Representative formulations comprising other lipid lowering agents are well known in the art. It is contemplated that where the two active ingredients are administered as a single composition, the dosage forms disclosed above for substituted azetidinone compounds may readily be modified using the knowledge of one skilled in the art.

The treatment compositions of the present invention can inhibit the intestinal absorption of sitosterol in an animal model, as shown in the Example below. Thus, the treatment compositions of the present invention are hypositosterolemic agents by virtue of their ability to inhibit the intestinal absorption of sitosterol and can be useful in the treatment and/or prevention of vascular disease, arteriosclerosis, atherosclerosis and sitosterolemia in mammals, in particular in humans.

In other embodiments, the present invention provides a method of treating vascular disease, arteriosclerosis and/or atherosclerosis, comprising administering to a mammal in need of such treatment an effective amount of at least one treatment composition comprising at least one sterol and/or stanol absorption inhibitor to reduce plasma or tissue concentration of at least one non-cholesterol sterol, such as a phytosterol, 5α-stanol and mixtures thereof.

In another embodiment, the present invention provides a method of treating or preventing sitosterolemia comprising administering to a mammal in need of such treatment an effective amount of at least one sterol absorption inhibitor or pharmaceutically acceptable salt or solvate thereof or prodrug thereof.

In another embodiment, the present invention provides a therapeutic combination comprising:

a) a first amount of the compound of Formula (VIII)

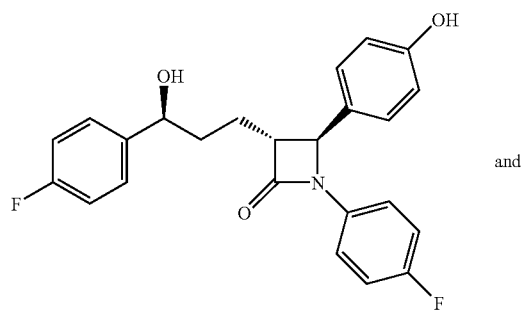

(VIII)

and b) a second amount of a lipid lowering agent, wherein the first amount and the second amount taken together in their totality comprise a therapeutically effective amount for the treatment or prevention of sitosterolemia in a mammal.

Normal concentrations or levels of sitosterol in the plasma of humans is generally less than about 0.2 milligrams/deciliter (mg/dl). Homozygous sitosterolemic humans can exhibit sitosterol levels of greater than 0.2 mg/dl, typically about 7 to about 60 mg/dl or higher. Heterozygous sitosterolemic humans can exhibit sitosterol levels of greater than 0.2 mg/dl, typically about 0.3 to about 1 mg/dl or higher.

In another embodiment of the invention, the compositions and therapeutic combinations of the present invention can reduce plasma and/or tissue concentration of at least one sterol (including but not limited to phytosterols (such as sitosterol, campesterol, stigmasterol and avenosterol)) and/or at least one stanol (including but not limited to 5α-stanols (such as cholestanol, 5α-campestanol, 5α-sitostanol)), and mixtures thereof, optionally in combination with cholesterol. The plasma and/or tissue concentration can be reduced by administering to a mammal in need of such treatment an effective amount of at least one treatment composition or therapeutic combination comprising at least one sterol absorption inhibitor or at least one stanol absorption inhibitor described above. The reduction in plasma and/or tissue concentration of sterols can range from about 1 to about 70 percent, and preferably about 10 to about 50 percent of the concentration measured prior to administration of at least one treatment composition or therapeutic combination comprising at least one sterol and/or stanol absorption inhibitor described above. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593-600 (1999), incorporated by reference herein.

In an alternative embodiment, the plasma and/or tissue concentration of sterols can be reduced by administering to a mammal in need of such treatment an effective amount of at least one treatment composition comprising at least one sterol and/or stanol absorption inhibitor and an effective amount of at least one bile acid sequestrant.

In a further embodiment, the plasma and/or tissue concentration of sterols can be reduced by administering to a mammal in need of such treatment an effective amount of at least one treatment composition comprising at least one sterol and/or stanol absorption inhibitor and an effective amount of at least one other lipid lowering agent.

Reducing the plasma or tissue concentration of non-cholesterol sterols, such as phytosterol(s) and/or 5α-stanol(s), in a mammal can be useful in the treatment and/or prevention of vascular conditions or disease, such as vascular inflammation, arteriosclerosis, atherosclerosis, hypercholesterolemia and sitosterolemia, and cardiovascular events, stroke and obesity.

Vascular disease is a term that broadly encompasses all disorders of blood vessels including small and large arteries and veins and blood flow. The most prevalent form of vascular disease is arteriosclerosis, a condition associated with the thickening and hardening of the arterial wall. Arteriosclerosis of the large vessels is referred to as atherosclerosis. Atherosclerosis is the predominant underlying factor in vascular disorders such as coronary artery disease, aortic aneurysm, arterial disease of the lower extremities and cerebrovascular disease.

The methods of the present invention can be used to prevent or reduce the risk of an occurrence of a fatal or non-fatal cardiovascular event in patients having no history of clinically evident coronary heart disease prior to the initial administration of the compounds and treatments of the present invention, as well as patients having a history of clinically evident coronary heart disease. The phrase "cardiovascular event" includes but is not limited to fatal and non-fatal acute major coronary events, coronary revascularization procedures, peripheral vascular disease, stable angina and cerebrovascular insufficiency such as stroke.

The phrase "acute major coronary event" includes fatal myocardial infarction, witnessed and unwitnessed cardiac death and sudden death occurring from 1 hour up to 24 hours after collapse, non-fatal myocardial infarction including definite acute Q-wave myocardial infarction, non-Q-wave myocardial infarction, and silent subclinical (remote) myocardial infarction, and unstable angina pectoris. As used herein, "myocardial infarction" includes both Q-wave and non-Q-wave myocardial infarction and silent subclinical (remote) myocardial infarction.

In another embodiment, the present invention provides a method of preventing or reducing risk of a cardiovascular event comprising administering to a mammal an effective amount of at least one treatment composition comprising at least one sterol and/or stanol absorption inhibitor to reduce plasma or tissue concentration of at least one non-cholesterol sterol, such as phytosterols, at least one stanol, such as 5α-stanols, and mixtures thereof.

In another embodiment, the present invention provides a method of preventing or reducing risk of a cardiovascular event comprising administering an effective amount of at least one treatment composition comprising at least one sterol absorption inhibitor to reduce plasma or tissue concentration of at least one non-cholesterol sterol, such as phytosterols, at least one stanol, such as 5α-stanols, and mixtures thereof to a mammal having no history of clinically evident coronary heart disease prior to the initial administration.

Illustrating the invention are the following examples which, however, are not to be considered as limiting the invention the their details. Unless indicated otherwise, all parts and percentages in the following examples, as well as throughout the specification, are by weight.

EXAMPLE 1

In Vivo Evaluation in Mice

In vivo activity of compound VIII in mice was determined by the following procedure:

Male ApoE knockout mice, age 6 wks, were received from Jackson Laboratory along with age-matched C57BL/J. The mice were housed 5 per cage, normal light cycle, normal diet. Twenty-six mice of each variety were weighed and housed, 1 per cage, in suspended wire cages with normal light cycle, normal diet. After three days, the mice were reweighed. Based on body weight, the mice were divided into 5 groups for each type of treatment:

Control (corn oil) and Compositions including Compound VIII at 0.3, 1, 3, and 10 mg/kg of body weight per day.

Preparation of Compositions including Compound VIII based on 22 g average mouse body weight:

| Dosage of Compound VIII (mg/ml/day) | Compound VIII (ml) + corn oil (ml) |
|---|---|
| 10 mg/kg/day in 0.1 ml corn oil | 2.2 mg/ml* 10 ml = 22 mg in 10 ml corn oil |
| 3 mg/kg: | 3 ml of 10 mg/kg + 7 ml corn oil; |
| 1 mg/kg: | 3 ml of 3 mg/kg + 6 ml corn oil; |
| 0.3 mg/kg: | 2 ml of 1 mg/kg + 4.67 ml corn oil. |

The mice were gavaged using a feeding needle 30 min before receiving $^{14}$C-cholesterol (NEN, NEC 018) and $^3$H-sitosterol (NEN, CUS 030T). The radioactive dose was prepared from:

114 μL $^3$H-sitosterol stock (1 μCi/μL in ethanol);

1.425 mL $^{14}$C-cholesterol stock (40 μCi/mL in ethanol);

5.7 mg cholesterol, Sigma C 8667;

5.7 mg β-sitosterol, Sigma, S 1270;

The ethanol was removed under $N_2$;

5.7 ml of corn oil was added, and the mixture was warmed to 60° C.; and shaken for 1 hr.

Each 0.1 ml dose contained 2 μCi $^3$H-sitosterol, 0.1 mg cold (non radioactive) sitosterol; 1 μCi $^{14}$C-cholesterol, and 0.1 mg cold (non radioactive) cholesterol. Radioactive content was verified: 5×10 μl counted in Beckman LSC (liquid simulation counter). Tritiated sitosterol was used as an "unabsorbable" marker to compare to the absorption of [$^{14}$C]-cholesterol in a mouse fecal isotope ratio cholesterol absorption model.

On the $4^{th}$, $5^{th}$, and $6^{th}$ days, feces were collected and stored at −20° C. in vials just before dosing with Control or Compound VIII late in the day. Termination of the experiment on the $7^{th}$ day involved sacrifice by exsanguination, removal and weighing of the liver. 3×~250 mg samples of liver were put in vials. The liver samples were digested with 1 ml of 1N NaOH at 60° overnight, neutralized with 0.1 ml 12N HCl and counted for $^{14}$C and $^3$H. The blood samples were allowed to clot at room temp for 1 hr, then centrifuged at 1000 G for 15 min. The serum was analyzed for total cholesterol (see Wako C I I; see Allain C C, Poon L S, Chan C S G, Richmond W, Fu P C. Enzymatic Determination of Total Serum Cholesterol. Clin. Chem. 1974; 20:470-475, which is incorporated by reference herein) and radioactivity (2×50 μL). Fecal samples were analyzed for radioactivity by combustion in a Packard Oxidizer followed by Beckman LSC.

In this experiment, Wild type mice (C57BL/6J) and mice deficient in apoprotein E (Apo E KO) were found to absorb from 0.15-0.38% of the original [$^3$H]-sitosterol dose administered into their livers. When Compound VIII was given, it was found to dose dependently inhibit the absorption and hepatic accumulation of sitosterol as shown in Table 1 below.

TABLE 1

Effect of Compound VIII on Sitosterol Absorption in Mice

| Mouse strain | Treatment | % of administered dose absorbed of [$^3$H]-sitosterol in liver (total animal liver) | | |
|---|---|---|---|---|
| | | average | ±sem | p = |
| C57BL/6J | Control | 0.1479 | ±0.0337 | |
| | Compound VIII 0.3 mg/kg | 0.1093 | ±0.0143 | |
| | Compound VIII 1 mg/kg | 0.0588 | ±0.0115 | (.046) |
| | Compound VIII 3 mg/kg | 0.0489 | ±0.0067 | (.024) |
| | Compound VIII 10 mg/kg | 0.0552 | ±0.0151 | (.040) |
| ApoE KO | Control | 0.3773 | ±0.0525 | |
| | Compound VIII 0.3 mg/kg | 0.1863 | ±0.0246 | 0.013 |
| | Compound VIII 1 mg/kg | 0.1019 | ±0.0225 | 0.0019 |
| | Compound VIII 3 mg/kg | 0.0772 | ±0.0050 | 0.0023 |
| | Compound VIII 10 mg/kg | 0.0780 | ±0.0179 | 0.0017 |

N = 4–6 mice per treatment
sem = standard error of mean
p = probability

EXAMPLE 2

In Vivo Evaluation in Humans

In a randomized multicenter, double-blind, placebo-controlled, 8-week trial, 37 human patients previously diagnosed with homozygous sitosterolemia were randomized to receive Compound VIII (n=30) or placebo (n=7):

Treatment A—Compound VIII given orally as 1 dose (10 mg) per day,

Treatment B—Placebo (matching image of Compound VIII 10 mg) given orally as 1 dose per day, every morning for 8 consecutive weeks.

During the trial, subjects were instructed to maintain (as a minimum) a National Cholesterol Education Program (NCEP) Step 1 diet Patients were instructed to maintain a diary of food intake and monitored prior to randomization, at baseline and during therapy. Results of the central diet analysis for each subject were reported as a RISCC score (Ratio of Ingested Saturated fat and Cholesterol to Calories) and as dietary components. RISCC scores indicate the potential for a diet to influence plasma lipid levels. A score ranging from 14 to 20 correlates with a NCEP step 1 diet.

Lipid/lipoproteins Determinations

Low-Density-Lipoprotein-Cholesterol (LDL-C) results were reported as direct LDL-C (plasma concentration was determined following a standard ultra centrifugation/precipitation procedure; lipid and lipoprotein analysis, see *Manual of Laboratory Operations: Lipid Research Clinics Program Report*. Washington, D.C.: US Department of Health, Education, and Welfare publication; 1974. NIH 75-628, vol 1, which is incorporated by reference herein or beta-quantification) and calculated LDL-C (plasma concentration; based on Freidewald equation: LDL-C=Total cholesterol minus (Triglycerides divided by 5) minus High-density-lipoprotein cholesterol (HDL-C)).

Total cholesterol and Triglycerides were determined enzymatically using a Hitachi 747 analyzer; see, Steiner P M, Freidel J, Bremner W F, Stein E A: Standardization of micromethods for plasma cholesterol, triglyceride and HDL-cholesterol with the Lipid Clinics' methodology [abstract]. *J Clin Chem Clin Biochem* 1981;19:850, which is incorporated by reference herein.

HDL-C was determined enzymatically after heparin and magnesium precipitation; see, Steele W B, Koehle D F, Azar M M, Blaszkowski T P, Kuba K, Dempsey M E: Enzymatic determinations of cholesterol in high density lipoprotein fractions prepared by precipitation technique. *Clin Chem* 1976; 22:98-101, which is incorporated by reference herein.

Plasma plant sterols (sitosterol and campesterol) and LDL-C were assessed at baseline (Day 1) and at endpoint (average of Weeks 6 and 8 values). See: Salen, Gerald; Shore, Virgie; Tint, G S; Forte, T: Shefer, S; Horak, I; Horak, E; Dayal, B; Nguyen, L.; Batta, A K; Lindgren, F T; Kwiterovich, Jr, P O, "Increased sitosterol absorption, decreased removal and expanded body pools compensate for reduced cholesterol synthesis in sitosterolemia with xanthomatosis", J Lipid Res, Vol. 30, pp 1319-30, (1989) and Lutjohann, D; Bjorkhem, I; Beil, U F, and von Bergmann, K, "Sterol absorption and sterol balance in phytosterolemia evaluated by deuterium-labeled sterols: effect of sitostanol treatment" J Lipid Res. Vol. 36:(8), pp 1763-73, (1995), each of which is incorporated by reference herein.

Results:

The mean (S.E.) percent (%) change from Baseline at endpoint in plant sterols and LDL-C (mean, 95% CI) are shown in Table 1 below:

TABLE 1

| Treatment | Sitosterol | Campesterol | LDL-C |
|---|---|---|---|
| A | −21.0% (2.8%) | −24.3% (2.9%) | −13.6% (−21.7%, −5.5%) |
| B (control) | 4.0% (5.3%) | 3.2% (5.5%) | 16.7% (31.6%, 64.9%) |

The coadministration of 10 mg of Compound VIII was well tolerated and caused a significant (p<0.001) reduction in sitosterol and campesterol compared to placebo.

Preparation of Compound (VIII)

Step 1): To a solution of (S)-4-phenyl-2-oxazolidinone (41 g, 0.25 mol) in $CH_2Cl_2$ (200 ml), was added 4-dimethylaminopyridine (2.5 g, 0.02 mol) and triethylamine (84.7 ml, 0.61 mol) and the reaction mixture was cooled to 0° C. Methyl-4-(chloroformyl)butyrate (50 g, 0.3 mol) was added as a solution in $CH_2Cl_2$ (375 ml) dropwise over 1 h, and the reaction was allowed to warm to 22° C. After 17 h, water and $H_2SO_4$ (2N, 100 ml), was added the layers were separated, and the organic layer was washed sequentially with NaOH (10%), NaCl (sat'd) and water. The organic layer was dried over $MgSO_4$ and concentrated to obtain a semicrystalline product.

Step 2): To a solution of $TiCl_4$ (18.2 ml, 0.165 mol) in $CH_2Cl_2$ (600 ml) at 0° C., was added titanium isopropoxide (16.5 ml, 0.055 mol). After 15 min, the product of Step 1 (49.0 g, 0.17 mol) was added as a solution in $CH_2Cl_2$ (100 ml). After 5 min., diisopropylethylamine (DIPEA) (65.2 ml, 0.37 mol) was added and the reaction mixture was stirred at 0° C. for 1 h, the reaction mixture was cooled to −20° C., and 4-benzyloxybenzylidine(4-fluoro)aniline (114.3 g, 0.37 mol) was added as a solid. The reaction mixture was stirred vigorously for 4 h at −20° C., then acetic acid was added as a solution in $CH_2Cl_2$ dropwise over 15 min, the reaction mixture was allowed to warm to 0° C., and $H_2SO_4$ (2N) was added. The reaction mixture was stirred an additional 1 h, the layers were separated, washed with water, separated and the organic layer was dried. The crude product was crystallized from ethanol/water to obtain the pure intermediate.

Step 3): To a solution of the product of Step 2 (8.9 g, 14.9 mmol) in toluene (100 ml) at 50° C., was added N,O-bis(trimethylsilyl)acetamide (BSA) (7.50 ml, 30.3 mmol). After 0.5 h, solid TBAF (0.39 g, 1.5 mmol) was added and the reaction mixture stirred at 50° C. for an additional 3 h. The reaction mixture was cooled to 22° C., $CH_3OH$ (10 ml), was added. The reaction mixture was washed with HCl (1N), $NaHCO_3$ (1N) and NaCl (sat'd.), and the organic layer was dried over $MgSO_4$.

Step 4): To a solution of the product of Step 3 (0.94 g, 2.2 mmol) in $CH_3OH$ (3 ml), was added water (1 ml) and $LiOH.H_2O$ (102 mg, 2.4 mmole). The reaction mixture was stirred at 22° C. for 1 h and then additional $LiOH.H_2O$ (54 mg, 1.3 mmole) was added. After a total of 2 h, HCl (1N) and EtOAc was added, the layers were separated, the organic layer was dried and concentrated in vacuo. To a solution of the resultant product (0.91 g, 2.2 mmol) in $CH_2Cl_2$ at 22° C., was added ClCOCOCl (0.29 ml, 3.3 mmol) and the mixture stirred for 16 h. The solvent was removed in vacuo.

Step 5): To an efficiently stirred suspension of 4-fluorophenylzinc chloride (4.4 mmol) prepared from 4-fluorophenylmagnesium bromide (1M in THF, 4.4 ml, 4.4 mmol) and $ZnCl_2$ (0.6 g, 4.4 mmol) at 4° C., was added tetrakis(triphenylphosphine)palladium (0.25 g, 0.21 mmol) followed by the product of Step 4 (0.94 g, 2.2 mmol) as a solution in THF (2 ml). The reaction was stirred for 1 h at 0° C. and then for 0.5 h at 22° C. HCl (1N, 5 ml) was added and the mixture was extracted with EtOAc. The organic layer was concentrated to an oil and purified by silica gel chromatography to obtain 1-(4-fluorophenyl)-4(S)-(4-hydroxyphenyl)-3(R)-(3-oxo-3-phenylpropyl)-2-azetidinone:

HRMS calc'd for $C_{24}H_{19}F_2NO_3$=408.1429, found 408.1411.

Step 6): To the product of Step 5 (0.95 g, 1.91 mmol) in THF (3 ml), was added (R)-tetrahydro-1-methyl-3,3-diphenyl-1H,3H-pyrrolo-[1,2-c][1,3,2]oxazaborole (120 mg, 0.43 mmol) and the mixture was cooled to −20° C. After 5 min, borohydride-dimethylsulfide complex (2M in THF, 0.85 ml, 1.7 mmol) was added dropwise over 0.5 h. After a total of 1.5 h, $CH_3OH$ was added followed by HCl (1 N) and the reaction mixture was extracted with EtOAc to obtain 1-(4-fluorophenyl)-3(R)-[3(S)-(4-fluorophenyl)-3-hydroxypropyl)]-4(S)-[4-(phenylmethoxy)phenyl]-2-azetidinone (compound 6A-1) as an oil. $^1H$ in $CDCl_3$ d $H_3$=4.68. J=2.3 Hz. CI (M+H) 500.

Use of (S)-tetra-hydro-1-methyl-3,3-diphenyl-1H,3H-pyrrolo-[1,2-c][1,3,2]oxazaborole gives the corresponding 3(R)-hydroxypropyl azetidinone (compound 6B-1). $^1H$ in $CDCl_3$ d $H_3$=4.69. J=2.3 Hz. CI (M+H) 500.

To a solution of compound 6A-1 (0.4 g, 0.8 mmol) in ethanol (2 ml), was added 10% Pd/C (0.03 g) and the reaction mixture was stirred under a pressure (60 psi) of $H_2$ gas for 16 h. The reaction mixture was filtered and the solvent was concentrated to obtain compound 6A. Mp 164-166° C.; CI (M+H) 410. $[\alpha]_D^{25}$=−28.1° (c 3, $CH_3OH$). Elemental analysis calc'd for $C_{24}H_{21}F_2NO_3$: C, 70.41; H, 5.17; N, 3.42; found C, 70.25; H, 5.19; N, 3.54.

Similarly treat compound 6B-1 to obtain compound 6B. Mp 129.5-132.5° C.; CI (M+H) 410. Elemental analysis calc'd for $C_{24}H_{21}F_2NO_3$: C 70.41; H 5.17; N 3.42; found C 70.30; H 5.14; N 3.52.

Step 6' (Alternative): To a solution of the product of Step 5 (0.14 g, 0.3 mmol) in ethanol (2 ml), was added 10% Pd/C (0.03 g) and the reaction was stirred under a pressure (60 psi) of $H_2$ gas for 16 h. The reaction mixture was filtered and the solvent was concentrated to afford a 1:1 mixture of compounds 6A and 6B.

It will be appreciated by those skilled in the art that changes could be made to the embodiments described above without departing from the broad inventive concept thereof. It is understood, therefore, that this invention is not limited to the particular embodiments disclosed, but it is intended to cover modifications which are within the spirit and scope of the invention, as defined by the appended claims.

Therefore, I claim:

1. A method of treating sitosterolemia, comprising administering to a mammal in need of such treatment an effective amount of at least one sterol absorption inhibitor, or pharmaceutically acceptable salt or solvate of the least one sterol absorption inhibitor, or prodrug of the at least one sterol absorption inhibitor or pharmaceutically acceptable salt or solvate of the least one sterol absorption inhibitor, or mixture thereof.

2. The method of claim 1, wherein the at least one sterol absorption inhibitor is represented by Formula (I):

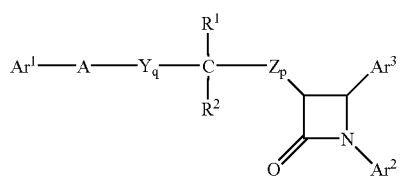
(I)

or isomers thereof, or pharmaceutically acceptable salts or solvates of the compounds of Formula (I) or of the isomers thereof, or prodrugs of the compounds of Formula (I) or of the isomers, salts or solvates thereof, wherein:
- $Ar^1$ is $R^3$-substituted aryl;
- $Ar^2$ is $R^4$-substituted aryl;
- $Ar^3$ is $R^5$-substituted aryl;
- Y and Z are independently selected from the group consisting of $-CH_2-$, $-CH$(lower alkyl)- and $-C$(dilower alkyl)-;
- A is $-O-$, $-S-$, $-S(O)-$ or $-S(O)_2-$;
- $R^1$ is selected from the group consisting of $-OR^6$, $-O(CO)R^6$, $-O(CO)OR^9$ and $-O(CO)NR^6R^7$;
- $R^2$ is selected from the group consisting of hydrogen, lower alkyl and aryl; or $R^1$ and $R^2$ together are $=O$;
- q is 1, 2 or 3;
- p is 0, 1, 2, 3 or 4;
- $R^5$ is 1-3 substituents independently selected from the group consisting of $-OR^6$, $-O(CO)R^6$, $-O(CO)OR^9$, $-O(CH_2)_{1-5}OR^9$, $-O(CO)NR^6R^7$, $-NR^6R^7$, $-NR^6(CO)R^7$, $-NR^6(CO)OR^9$, $-NR^6(CO)NR^7R^8$, $-NR^6SO_2$-lower alkyl, $-NR^6SO_2$-aryl, $-CONR^6R^7$, $-COR^6$, $-SO_2NR^6R^7$, $S(O)_{0-2}$-alkyl, $S(O)_{0-2}$-aryl, $-O(CH_2)_{1-10}-COOR^6$, $-O(CH_2)_{1-10}CONR^6R^7$, o-halogeno, m-halogeno, o-lower alkyl, m-lower alkyl, -(lower alkylene)-$COOR^6$, and $-CH=CH-COOR^6$;
- $R^3$ and $R^4$ are independently 1-3 substituents independently selected from the group consisting of $R^5$, hydrogen, p-lower alkyl, aryl, $-NO_2$, $-CF_3$ and p-halogeno;
- $R^6$, $R^7$ and $R^8$ are independently selected from the group consisting of hydrogen, lower alkyl, aryl and aryl-substituted lower alkyl; and
- $R^9$ is lower alkyl, aryl or aryl-substituted lower alkyl.

3. The method of claim 1, wherein the at least one sterol absorption inhibitor is represented by Formula (II):

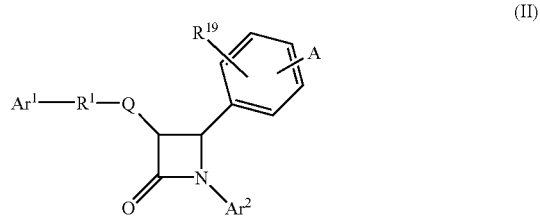
(II)

or isomers thereof, or pharmaceutically acceptable salts or solvates of the compounds of Formula (II) or of the isomers thereof, or prodrugs of the compounds of Formula (II) or of the isomers, salts or solvates thereof, wherein:
- A is selected from the group consisting of $R^2$-substituted heterocycloalkyl, $R^2$-substituted heteroaryl, $R^2$-substituted benzofused heterocycloalkyl, and $R^2$-substituted benzofused heteroaryl;
- $Ar^1$ is aryl or $R^3$-substituted aryl;
- $Ar^2$ is aryl or $R^4$-substituted aryl;
- Q is a bond or, with the 3-position ring carbon of the azetidinone, forms the spiro group

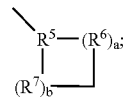

- $R^1$ is selected from the group consisting of
  - $-(CH_2)_q-$, wherein q is 2-6, provided that when Q forms a spiro ring, q can also be zero or 1;
  - $-(CH_2)_e$-G-$(CH_2)_r-$, wherein G is $-O-$, $-C(O)-$, phenylene, $-NR^8-$ or $-S(O)_{0-2}$-e is 0-5 and r is 0-5, provided that the sum of e and r is 1-6;
  - $-(C_2-C_6$ alkenylene)-; and
  - $-(CH_2)_f-V-(CH_2)_g-$, wherein V is $C_3-C_6$ cycloalkylene, f is 1-5 and g is 0-5, provided that the sum of f and g is 1-6;
- $R^5$ is

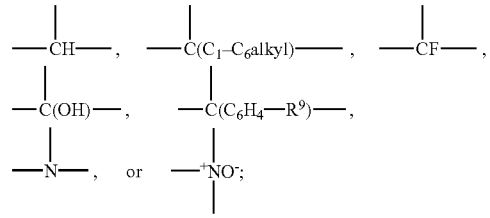

- $R^6$ and $R^7$ are independently selected from the group consisting of $-CH_2-$, $-CH(C_1-C_6$ alkyl)-, $-C$(di-$(C_1-C_6)$alkyl), $-CH=CH-$ and $-C(C_1-C_6$ alkyl)$=CH-$; or $R^5$ together with an adjacent $R^6$, or $R^5$ together with an adjacent $R^7$, form a $-CH=CH-$ or a $-CH=C(C_1-C_6$ alkyl)- group;

a and b are independently 0, 1, 2 or 3, provided both are not zero; provided that when $R^6$ is —CH=CH— or —C($C_1$-$C_6$ alkyl)=CH—, a is 1; provided that when $R^7$ is —CH=CH— or —C($C_1$-$C_6$ alkyl)=CH—, b is 1; provided that when a is 2 or 3, the $R^6$'s can be the same or different; and provided that when b is 2 or 3, the $R^7$'s can be the same or different;

and when Q is a bond, $R^1$ also can be:

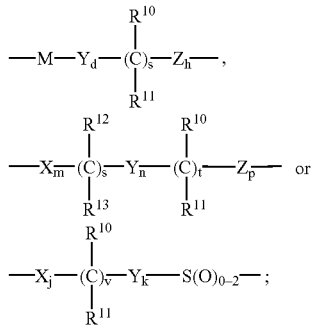

M is —O—, —S—, —S(O)— or —S(O)$_2$—;

X, Y and Z are independently selected from the group consisting of —CH$_2$—, —CH(C$_1$-C$_6$ alkyl)- and —C(di-(C$_1$-C$_6$)alkyl);

$R^{10}$ and $R^{12}$ are independently selected from the group consisting of —OR$^{14}$, —O(CO)R$^{14}$, —O(CO)OR$^{16}$ and —O(CO)NR$^{14}$R$^{15}$;

$R^{11}$ and $R^{13}$ are independently selected from the group consisting of hydrogen, (C$_1$-C$_6$)alkyl and aryl; or $R^{10}$ and $R^{11}$ together are =O, or $R^{12}$ and $R^{13}$ together are =O;

d is 1, 2 or 3;

h is 0, 1, 2, 3 or 4;

s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

$R^2$ is 1-3 substituents on the ring carbon atoms selected from the group consisting of hydrogen, (C$_1$-C$_{10}$)alkyl, (C$_2$-C$_{10}$)alkenyl, (C$_2$-C$_{10}$)alkynyl, (C$_3$-C$_6$)cycloalkyl, (C$_3$-C$_6$)cycloalkenyl, R$^{17}$-substituted aryl, R$^{17}$-substituted benzyl, R$^{17}$-substituted benzyloxy, R$^{17}$-substituted aryloxy, halogeno, —NR$^{14}$R$^{15}$, NR$^{14}$R$^{15}$(C$_1$-C$_6$ alkylene)-, NR$^{14}$R$^{15}$C(O)(C$_1$-C$_6$ alkylene)-, —NHC(O)R$^{16}$, OH, C$_1$-C$_6$ alkoxy, —OC(O)R$^{16}$, —COR$^{14}$, hydroxy(C$_1$-C$_6$)alkyl, (C$_1$-C$_6$)alkoxy(C$_1$-C$_6$)alkyl, NO$_2$, —S(O)$_{0-2}$R$^{16}$, —SO$_2$NR$^{14}$R$^{15}$ and —(C$_1$-C$_6$ alkylene)COOR$^{14}$; when $R^2$ is a substituent on a heterocycloalkyl ring, $R^2$ is as defined, or is =O or

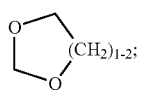

and, where $R^2$ is a substituent on a substitutable ring nitrogen, it is hydrogen, (C$_1$-C$_6$)alkyl, aryl, (C$_1$-C$_6$)

alkoxy, aryloxy, (C$_1$-C$_6$)alkylcarbonyl, arylcarbonyl, hydroxy, —(CH$_2$)$_{1-6}$CONR$^{18}$R$^{18}$,

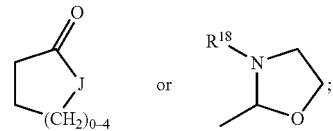

wherein J is —O—, —NH—, —NR$^{18}$— or —CH$_2$—;

$R^3$ and $R^4$ are independently selected from the group consisting of 1-3 substituents independently selected from the group consisting of (C$_1$-C$_6$)alkyl, —OR$^{14}$, —O(CO)R$^{14}$, —O(CO)OR$^{16}$, —O(CH$_2$)$_{1-5}$OR$^{14}$, —O(CO)NR$^{14}$R$^{15}$, —NR$^{14}$R$^{15}$, —NR$^{14}$(CO)R$^{15}$, —NR$^{14}$(CO)OR$^{16}$, —NR$^{14}$(CO)NR$^{15}$R$^{19}$, —NR$^{14}$SO$_2$R$^{16}$, —COOR$^{14}$, —CONR$^{14}$R$^{15}$, —COR$^{14}$, —SO$_2$NR$^{14}$R$^{15}$, S(O)$_{0-2}$R$^{16}$, —O(CH$_2$)$_{1-10}$—COOR$^{14}$, —O(CH$_2$)$_{1-10}$CONR$^{14}$R$^{15}$, —(C$_1$-C$_6$ alkylene)-COOR$^{14}$, —CH=CH—COOR$^{14}$, —CF$_3$, —CN, —NO$_2$ and halogen;

$R^8$ is hydrogen, (C$_1$-C$_6$)alkyl, aryl (C$_1$-C$_6$)alkyl, —C(O)R$^{14}$ or —COOR$^{14}$;

$R^9$ and $R^{17}$ are independently 1-3 groups independently selected from the group consisting of hydrogen, (C$_1$-C$_6$) alkyl, (C$_1$-C$_6$)alkoxy, —COOH, NO$_2$, —NR$^{14}$R$^{15}$, OH and halogeno;

$R^{14}$ and $R^{15}$ are independently selected from the group consisting of hydrogen, (C$_1$-C$_6$)alkyl, aryl and aryl-substituted (C$_1$-C$_6$)alkyl;

$R^{16}$ is (C$_1$-C$_6$)alkyl, aryl or R$^{17}$-substituted aryl;

$R^{18}$ is hydrogen or (C$_1$-C$_6$)alkyl; and $R^{19}$ is hydrogen, hydroxy or (C$_1$-C$_6$)alkoxy.

4. The method of claim 1, wherein the at least one sterol absorption inhibitor is represented by Formula (III):

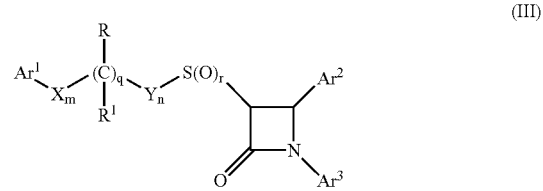

(III)

or isomers thereof, or pharmaceutically acceptable salts or solvates of the compounds of Formula (III) or of the isomers thereof, or prodrugs of the compounds of Formula (III) or of the isomers, salts or solvates thereof, wherein:

Ar$^1$ is aryl, R$^{10}$-substituted aryl or heteroaryl;

Ar$^2$ is aryl or R$^4$-substituted aryl;

Ar$^3$ is aryl or R$^5$-substituted aryl;

X and Y are independently selected from the group consisting of —CH$_2$—, —CH(lower alkyl)- and —C(dilower alkyl)-;

R is —OR$^6$, —O(CO)R$^6$, —O(CO)OR$^9$ or —O(CO)NR$^6$R$^7$;

$R^1$ is hydrogen, lower alkyl or aryl; or R and $R^1$ together are =O;

q is 0 or 1;

r is 0, 1 or 2;

m and n are independently 0, 1, 2, 3, 4 or 5; provided that the sum of m, n and q is 1, 2, 3, 4 or 5;

$R^4$ is 1-5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene) COOR$^6$ and —CH=CH—COOR$^6$;

R$^5$ is 1-5 substituents independently selected from the group consisting of —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, —CF$_3$, —CN, —NO$_2$, halogen, -(lower alkylene)COOR$^6$ and —CH=CH—COOR$^6$;

R$^6$, R$^7$ and R$^8$ are independently selected from the group consisting of hydrogen, lower alkyl, aryl and aryl-substituted lower alkyl;

R$^9$ is lower alkyl, aryl or aryl-substituted lower alkyl; and

R$^{10}$ is 1-5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$COOR$^6$, —O(CH$_2$)$_{1-10}$CONR$^6$R$^7$, —CF$_3$, —CN, —NO$_2$ and halogen.

5. The method of claim 1, wherein the at least one sterol absorption inhibitor is represented by Formula (IV):

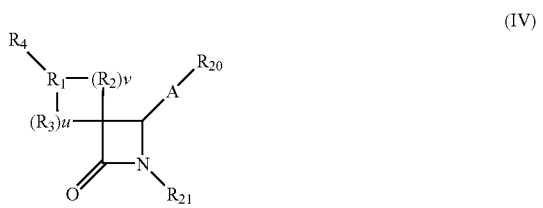

(IV)

or isomers thereof, or pharmaceutically acceptable salts or solvates of the compounds of Formula (IV) or of the isomers thereof, or prodrugs of the compounds of Formula (IV) or of the isomers, salts or solvates thereof, wherein:

R$_1$ is

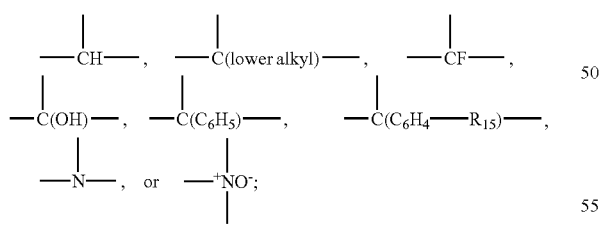

R$_2$ and R$_3$ are independently selected from the group consisting of: —CH$_2$—, —CH(lower alkyl)-, —C(di-lower alkyl)-, —CH=CH— and —C(lower alkyl)=CH—; or R$_1$ together with an adjacent R$_2$, or R$_1$ together with an adjacent R$_3$, form a —CH=CH— or a —CH=C(lower alkyl)- group;

u and v are independently 0, 1, 2 or 3, provided both are not zero; provided that when R$_2$ is —CH=CH— or —C(lower alkyl)=CH—, v is 1; provided that when R$_3$ is —CH=CH— or —C(lower alkyl)=CH—, u is 1; provided that when v is 2 or 3, the R$_2$'s can be the same or different; and provided that when u is 2 or 3, the R$_3$'s can be the same or different;

R$_4$ is selected from B—(CH$_2$)$_m$C(O)—, wherein m is 0, 1, 2, 3, 4 or 5;

B—(CH$_2$)$_q$—, wherein q is 0, 1, 2, 3, 4, 5 or 6;

B—(CH$_2$)$_e$-Z-(CH$_2$)$_r$—, wherein Z is —O—, —C(O)—, phenylene, —N(R$_8$)— or —S(O)$_{0-2}$—, e is 0, 1, 2, 3, 4 or 5 and r is 0, 1, 2, 3, 4 or 5, provided that the sum of e and r is 0, 1, 2, 3, 4, 5 or 6;

B—(C$_2$-C$_6$ alkenylene)-;

B—(C$_4$-C$_6$ alkadienylene)-;

B—(CH$_2$)$_t$-Z-(C$_2$-C$_6$ alkenylene)-, wherein Z is as defined above, and wherein t is 0, 1, 2 or 3, provided that the sum of t and the number of carbon atoms in the alkenylene chain is 2, 3, 4, 5 or 6;

B—(CH$_2$)$_f$—V—(CH$_2$)$_g$—, wherein V is C$_3$-C$_6$ cycloalkylene, f is 1, 2, 3, 4 or 5 and g is 0, 1, 2, 3, 4 or 5, provided that the sum of f and g is 1, 2, 3, 4, 5 or 6;

B—(CH$_2$)$_t$—V—(C$_2$-C$_6$ alkenylene)- or

B—(C$_2$-C$_6$ alkenylene)-V—(CH$_2$)$_t$—, wherein V and t are as defined above, provided that the sum of t and the number of carbon atoms in the alkenylene chain is 2, 3, 4, 5 or 6;

B—(CH$_2$)$_a$-Z-(CH$_2$)$_b$—V—(CH$_2$)$_d$—, wherein Z and V are as defined above and a, b and d are independently 0, 1, 2, 3, 4, 5 or 6, provided that the sum of a, b and d is 0, 1, 2, 3, 4, 5 or 6; or T—(CH$_2$)$_s$—, wherein T is cycloalkyl of 3-6 carbon atoms and s is 0, 1, 2, 3, 4, 5 or 6; or R$_1$ and R$_4$ together form the group

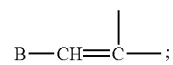

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

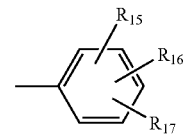

W is 1 to 3 substituents independently selected from the group consisting of lower alkyl, hydroxy lower alkyl, lower alkoxy, alkoxyalkyl, alkoxyalkoxy, alkoxycarbonylal koxy, (lower alkoxyimino)-lower alkyl, lower alkanedloyl, lower alkyl lower alkanedioyl, allyloxy, —CF$_3$, —OCF$_3$, benzyl, R$_7$-benzyl, benzyloxy, R$_7$-benzyloxy, phenoxy, R₇-phenoxy, dioxolanyl, NO₂, —N(R₈)(R₉), N(R₈)(R₉)-lower alkylene-, N(R₈)(R₉)-lower alkylenyloxy-, OH, halogeno, —ON, —N₃, —NHC(O)OR₁₀, —NHC(O)R₁₀, R₁₁O₂SNH—, (R₁₁O₂S)₂N—, —S(O)₂NH₂, —S(O)₀₋₂R₈, tert-butyldimethyl-silyloxymethyl, —C(O)R₁₂, —COOR₁₉, —CON(R₈)(R₉), —CH═CHC(O)R₁₂, -lower alkylene-C(O)R₁₂, R₁₀C(O)(lower alkylenyloxy)-, N(R₈)(R₉)C(O)(lower alkylenyloxy)- and

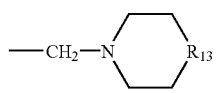

for substitution on ring carbon atoms, and the substituents on the substituted heteroaryl ring nitrogen atoms, when present, are selected from the group consisting of lower alkyl, lower alkoxy, —C(O)OR₁₀, —C(O)R₁₀, OH, N(R₈)(R₉)-lower alkylene-,N(R₈)(R₉)-lower alkylenyloxy-, —S(O)₂NH₂ and 2-(trimethylsilyl)-ethoxymethyl;

R₇ is 1-3 groups independently selected from the group consisting of lower alkyl, lower alkoxy, —COOH, NO₂, —N(R₈)(R₉), OH, and halogeno;

R₈ and R₉ are independently selected from H or lower alkyl;

R₁₀ is selected from lower alkyl, phenyl, R₇-phenyl, benzyl or R₇-benzyl;

R₁₁ is selected from OH, lower alkyl, phenyl, benzyl, R₇-phenyl or R₇-benzyl;

R₁₂ is selected from H, OH, alkoxy, phenoxy, benzyloxy,

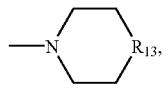

—N(R₈)(R₉), lower alkyl, phenyl or R₇-phenyl;

R₁₃ is selected from —O—, —CH₂—, —NH—, —N(lower alkyl)- or —NC(O)R₁₉;

R₁₅, R₁₆ and R₁₇ are independently selected from the group consisting of H and the groups defined for W; or R₁₅ is hydrogen and R₁₆ and R₁₇, together with adjacent carbon atoms to which they are attached, form a dioxolanyl ring;

R₁₉ is H, lower alkyl, phenyl or phenyl lower alkyl; and

R₂₀ and R₂₁ are independently selected from the group consisting of phenyl, W-substituted phenyl, naphthyl, W-substituted naphthyl, indanyl, indenyl, tetrahydronaphthyl, benzod ioxolyl, heteroaryl, W-substituted heteroaryl, benzofused heteroaryl, W-substituted benzofused heteroaryl and cyclopropyl, wherein heteroaryl is as defined above.

6. The method of claim 1, wherein the at least one sterol absorption inhibitor is represented by Formula (VA) or Formula (VB):

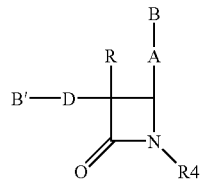

(VA)

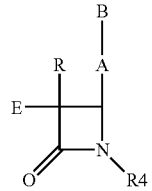

(VB)

or isomers thereof, or pharmaceutically acceptable salts or solvates of the compounds of Formula (VA) or (VB) or of the isomers thereof, or prodrugs of the compounds of Formula (VA) or (VB) or of the isomers, salts or solvates thereof, wherein:

A is —CH═CH—, —C≡C— or —(CH₂)ₚ— wherein p is 0, 1 or 2;

B is

B' is

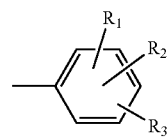 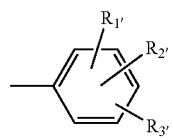

D is —(CH₂)ₘC(O)— or —(CH₂)_q— wherein m is 1, 2, 3 or 4 and q is 2, 3 or 4;

E is C₁₀ to C₂₀ alkyl or —C(O)—(C₉ to C₁₉)-alkyl, wherein the alkyl is straight or branched, saturated or containing one or more double bonds;

R is hydrogen, C₁-C₁₅ alkyl, straight or branched, saturated or containing one or more double bonds, or B—(CH₂)ᵣ—, wherein r is 0,1, 2, or 3;

R₁, R₂, R₃, R₁', R₂', and R₃' are independently selected from the group consisting of hydrogen, lower alkyl, lower alkoxy, carboxy, NO₂, NH₂, OH, halogeno, lower alkylamino, dilower alkylamino, —NHC(O)OR₅, R₆O₂SNH— and —S(O)₂NH₂;

R₄ is

wherein n is 0, 1, 2 or 3;

R₅ is lower alkyl; and

R₆ is OH, lower alkyl, phenyl, benzyl or substituted phenyl, wherein the substituents are 1-3 groups independently selected from the group consisting of lower alkyl, lower alkoxy, carboxy, $NO_2$, $NH_2$, OH, halogeno, lower alkylamino and dilower alkylamino.

7. The method of claim 1, wherein the at least one sterol absorption inhibitor is represented by Formula (VI):

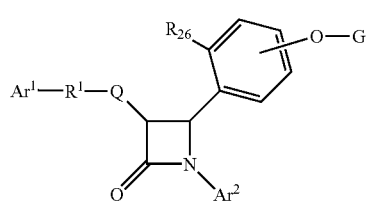

or isomers thereof, or pharmaceutically acceptable salts or solvates of the compounds of Formula (VI) or of the isomers thereof, or prodrugs of the compounds of Formula (VI) or of the isomers, salts or solvates thereof, wherein:

$R_{26}$ is H or $OG^1$;

G and $G^1$ are independently selected from the group consisting of

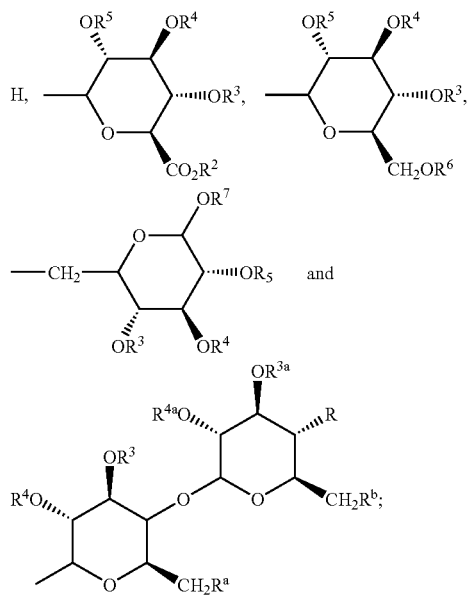

provided that when $R_{26}$ is H or OH, G is not H;

R, $R^a$ and $R^b$ are independently selected from the group consisting of H, —OH, halogeno, —$NH_2$, azido, ($C_1$-$C_6$)alkoxy($C_1$-$C_6$)-alkoxy and —W—$R^{30}$;

wherein W is independently selected from the group consisting of —NH—C(O), —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$-$C_6$)alkyl, aryl and aryl($C_1$-$C_6$)alkyl;

$R^3$, $R^4$, $R^5$, $R^7$, $R^{3a}$ and $R^{4a}$ are independently selected from the group consisting of H, ($C_1$-$C_6$)alkyl, aryl($C_1$-$C_6$)alkyl, —C(O)($C_1$-$C_6$)alkyl and —C(O)aryl;

$R^{30}$ is selected from the group consisting of $R^{32}$-substituted T, $R^{32}$-substituted-T-($C_1$-$C_6$)alkyl, $R^{32}$-substituted-($C_2$-$C_4$)alkenyl, $R^{32}$-substituted-($C_1$-$C_6$)alkyl, $R^{32}$-substituted-($C_3$-$C_7$)cycloalkyl and $R^{32}$-substituted-($C_3$-C7)cycloalkyl($C_1$-$C_6$)alkyl;

$R^{31}$ is selected from the group consisting of H and ($C_1$-$C_4$) alkyl;

T is selected from the group consisting of phenyl, furyl, thienyl, pyrrolyl, oxazolyl, isoxazolyl, thiazolyl, losthiazolyl, benzothiazolyl, thiadiazolyl, pyrazolyl, imidazolyl and pyridyl;

$R^{32}$ is independently selected from 1-3 substituents independently selected from the group consisting of halogeno, ($C_1$-$C_4$)alkyl, —OH, phenoxy, —$CF_3$, —$NO_2$, ($C_1$-$C_4$)alkoxy, methylenedioxy, oxo, ($C_1$-$C_4$)alkylsulfanyl, ($C_1$-$C_4$)alkylsulfinyl, ($C_1$-$C_4$)alkylsulfonyl, —N($CH_3$)$_2$, —C(O)—NH($C_1$-$C_4$)alkyl, —C(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

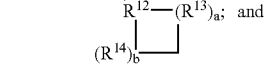

$R^1$ is selected from the group consisting of:
—($CH_2$)$_q$—, wherein q is 2-6, provided that when Q forms a spiro ring, q can also be zero or 1;
—($CH_2$)$_e$-E-($CH_2$)$_r$—, wherein E is —O—, —C(O)—, phenylene, —$NR^{22}$— or —S(O)$_{0-2}$—, e is 0-5 and r is 0-5, provided that the sum of e and r is 1-6;
—($C_2$-$C_6$)alkenylene-; and
—($CH_2$)$_f$—V—($CH_2$)$_g$—, wherein V is $C_3$-$C_6$ cycloalkylene, f is 1-5 and g is 0-5, provided that the sum of f and g is 1-6;

$R^{12}$ is

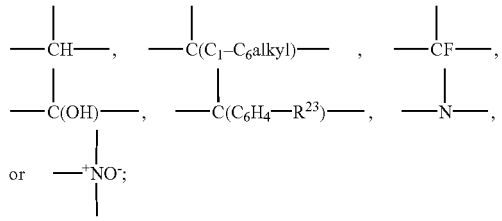

$R^{13}$ and $R^{14}$ are independently selected from the group consisting of —$CH_2$—, —CH($C_1$-$C_6$ alkyl)-, —C(di-($C_1$-$C_6$)alkyl), —CH=CH— and —C(($C_1$-$C_6$ alkyl) =CH—; or $R^{12}$ together with an adjacent $R^{13}$, or $R^{12}$ together with an adjacent $R^{14}$, form a —CH=CH— or a —CH=C($C_1$-$C_6$ alkyl)- group;

a and b are independently 0, 1, 2 or 3, provided both are not zero;

provided that when $R^{13}$ is —CH=CH— or —C($C_1$-$C_6$ alkyl)=CH—, a is 1;

provided that when R[14] is —CH═CH— or —C(C$_1$-C$_6$ alkyl)═CH—, b is 1;
provided that when a is 2 or 3, the R[13]'s can be the same or different; and
provided that when b is 2 or 3, the R[14]'s can be the same or different;
and when Q is a bond, R[1] also can be:

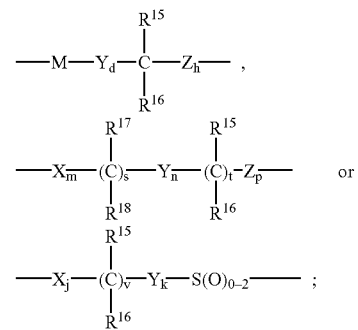

M is —O—, —S—, —S(O)— or —S(O)$_2$—;
X, Y and Z are independently selected from the group consisting of —CH$_2$—, —CH(C$_1$-C$_6$)alkyl- and —C(di-(C$_1$-C$_6$)alkyl);
R[10] and R[11] are independently selected from the group consisting of 1-3 substituents independently selected from the group consisting of (C$_1$-C$_6$)alkyl, —OR[19], —O(CO)R[19], —O(CO)OR[21], —O(CH$_2$)$_{1-5}$OR[19], —O(CO)NR[19]R[20], —NR[19]R[20], —NR[19](CO)R[20], —NR[19](CO)OR[21], —NR[19](CO)NR[20]R[25], —NR[19]SO$_2$R[21], —COOR[19], —CONR[19]R[20], —COR[19], —SO$_2$NR[19]R[20], S(O)$_{0-2}$R[21], —O(CH$_2$)$_{1-10}$—COOR[19], —O(CH$_2$)$_{1-10}$CONR[19]R[20], —(C$_1$-C$_6$ alkylene)-COOR[19], —CH═CH—COOR[19], —CF$_3$, —CN, —NO$_2$ and halogen;
R[15] and R[17] are independently selected from the group consisting of —OR[19], —O(CO)R[19], —O(CO)OR[21] and —O(CO)NR[19]R[20];
R[16] and R[18] are independently selected from the group consisting of H, (C$_1$-C$_6$)alkyl and aryl; or R[15] and R[16] together are ═O, or R[17] and R[18] together are ═O;
d is 1, 2 or 3;
h is 0, 1, 2, 3 or 4;
s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1, the sum of m, t and n is 1-5;
v is 0 or 1;
j and k are independently 1-5, provided that the sum of j, k and v is 1-5;
and when Q is a bond and R[1] is

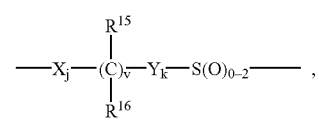

Ar[1] can also be pyridyl, isoxazolyl, furanyl, pyrrolyl, thienyl, imidazolyl, pyrazolyl, thiazolyl, pyrazinyl, pyrimidinyl or pyridazinyl;

R[19] and R[20] are independently selected from the group consisting of H, (C$_1$-C$_6$)alkyl, aryl and aryl-substituted (C$_1$-C$_6$)alkyl;
R[21] is (C$_1$-C$_6$)alkyl, aryl or R[24]-substituted aryl;
R[22] is H, (C$_1$-C$_6$)alkyl, aryl (C$_1$-C$_6$)alkyl, —C(O)R[19] or —COOR[19];
R[23] and R[24] are independently 1-3 groups independently selected from the group consisting of H, (C$_1$-C$_6$)alkyl, (C$_1$-C$_6$)alkoxy, —COOH, NO$_2$, —NR[19]R[20], —OH and halogeno; and
R[25] is H, —OH or (C$_1$-C$_6$)alkoxy.

8. The method of claim 1, wherein the at least one sterol absorption inhibitor is represented by Formula (VII):

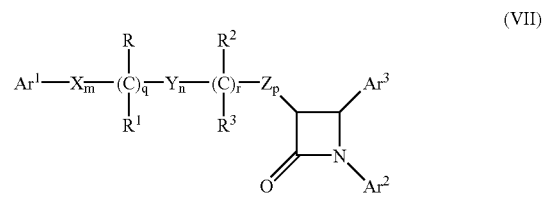

(VII)

or isomers thereof, or pharmaceutically acceptable salts or solvates of the compounds of Formula (VII) or of the isomers thereof, or prodrugs of the compounds of Formula (VII) or of the isomers, salts or solvates thereof, wherein:
Ar[1] and Ar[2] are independently selected from the group consisting of aryl and R[4]-substituted aryl;
Ar[3] is aryl or R[5]-substituted aryl;
X, Y and Z are independently selected from the group consisting of —OH$_2$—, —CH(lower alkyl)- and —C(dilower alkyl)-;
R and R[2] are independently selected from the group consisting of —OR[6], —O(CO)R[6], —O(CO)OR[9] and —O(CO)NR[6]R[7];
R[1] and R[3] are independently selected from the group consisting of hydrogen, lower alkyl and aryl;
q is 0 or 1;
r is 0 or 1;
m, n and p are independently 0, 1, 2, 3 or 4;
provided that at least one of q and r is 1, and the sum of m, n, p, q and r is 1, 2, 3, 4, 5 or 6; and
provided that when p is 0 and r is 1, the sum of m, q and n is 1, 2, 3, 4 or 5;
R[4] is 1-5 substituents independently selected from the group consisting of lower alkyl, —OR[6], —O(CO)R[6], —O(CO)OR[9], —O(CH$_2$)$_{1-5}$OR[6], —O(CO)NR[6]R[7], —NR[6]R[7], —NR[6](CO)R[7], —NR[6](CO)OR[9], —NR[6](CO)NR[7]R[8], —NR[6]SO$_2$R[9], —COOR[6], —CONR[6]R[7], —COR[6], —SO$_2$NR[6]R[7], —S(O)$_{0-2}$R[9], —O(CH$_2$)$_{1-10}$—COOR[6], —O(CH$_2$)$_{1-10}$CONR[6]R[7], -(lower alkylene)COOR[6], —CH═CH—COOR[6], —CF$_3$, —CN, —NO$_2$ and halogen;
R[5] is 1-5 substituents independently selected from the group consisting of —OR[6], —O(CO)R[6], —O(CO)OR[9], —O(CH$_2$)$_{1-5}$OR[6], —O(CO)NR[6]R[7], —NR[6]R[7], —NR[6](CO)R[7], —NR[6](CO)OR[9], —NR[6](CO)NR[7]R[8], —NR[6]SO$_2$R[9], —COOR[6], —CONR[6]R[7], —COR[6], —SO$_2$NR[6]R[7], —S(O)$_{0-2}$R[9], —O(CH$_2$)$_{1-10}$—COOR[6], —O(CH$_2$)$_{1-10}$CONR[6]R[7], -(lower alkylene)COOR[6] and —CH═CH—COOR[6];
R[6], R[7] and R[8] are independently selected from the group consisting of hydrogen, lower alkyl, aryl and aryl-substituted lower alkyl; and
R[9] is lower alkyl, aryl or aryl-substituted lower alkyl.

9. The method of claim 1, wherein the at least one sterol absorption inhibitor is represented by Formula (VIII):

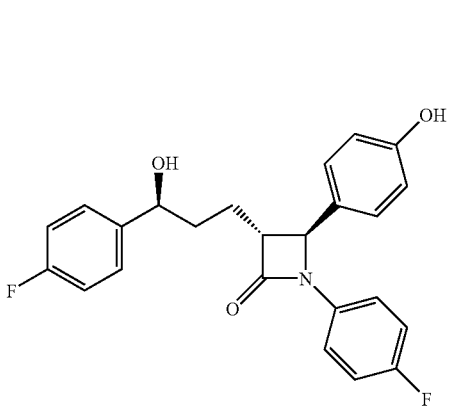

(VIII)

or pharmaceutically acceptable salts or solvates of the compound of Formula (VIII) or prodrugs of the compound of Formula (VIII) or of the salts or solvates thereof.

10. The method of claim 1, wherein the at least one sterol absorption inhibitor is represented by Formula (IX):

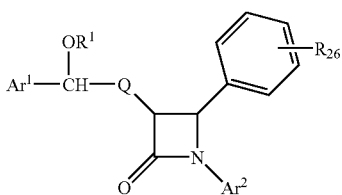

(IX)

or isomers thereof, or pharmaceutically acceptable salts or solvates of the compounds of Formula (IX) or of the isomers thereof, or prodrugs of the compounds of Formula (IX) or of the isomers, salts or solvates thereof, wherein:

$R^{26}$ is selected from the group consisting of:
a) OH;
b) $OCH_3$;
c) fluorine and
d) chlorine.

$R^1$ is selected from the group consisting of

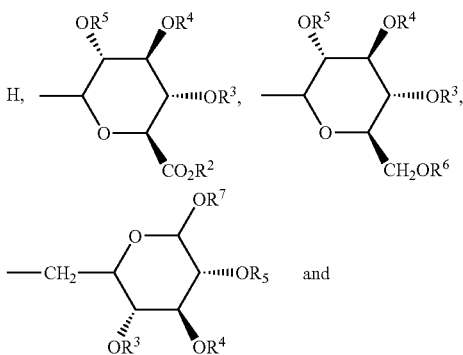

and

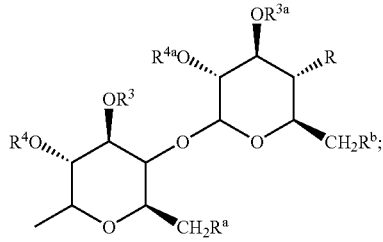

—$SO_3H$; natural and unnatural amino acids.

R, $R^a$ and $R^b$ are independently selected from the group consisting of H, —OH, halogeno, —$NH_2$, azido, ($C_1$-$C_6$)alkoxy($C_1$-$C_6$)-alkoxy and —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$-$C_6$)alkyl, aryl and aryl($C_1$-$C_6$)alkyl;

$R^3$, $R^4$, $R^5$, $R^7$, $R^{3a}$ and $R^{4a}$ are independently selected from the group consisting of H, ($C_1$-$C_6$)alkyl, aryl($C_1$-$C_6$)alkyl, —C(O)($C_1$-$C_6$)alkyl and —C(O)aryl;

$R^{30}$ is independently selected form the group consisting of $R^{32}$-substituted T, $R^{32}$-substituted-T-($C_1$-$C_6$)alkyl, $R^{32}$-substituted-($C_2$-$C_4$)alkenyl, $R^{32}$-substituted-($C_1$-$C_6$)alkyl, $R^{32}$-substituted-($C_3$-$C7$)cycloalkyl and $R^{32}$-substituted-($C_3$-$C7$)cycloalkyl($C_1$-$C_6$)alkyl;

$R^{31}$ is independently selected from the group consisting of H and ($C_1$-$C_4$)alkyl;

T is independently selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1-3 substituents independently selected from the group consisting of H, halogeno, ($C_1$-$C_4$)alkyl, —OH, phenoxy, —$CF_3$, —$NO_2$, ($C_1$-$C_4$)alkoxy, methylenedioxy, oxo, ($C_1$-$C_4$)alkylsulfanyl, ($C_1$-$C_4$)alkylsulfinyl, ($C_1$-$C_4$)alkylsulfonyl, —N($CH_3$)$_2$, —C(O)—NH($C_1$-$C_4$)alkyl, —O(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is —($CH_2$)$_q$—, wherein q is 2-6, or, with the 3-position ring carbon of the azetidinone, forms the spiro group

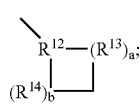

$R^{12}$ is

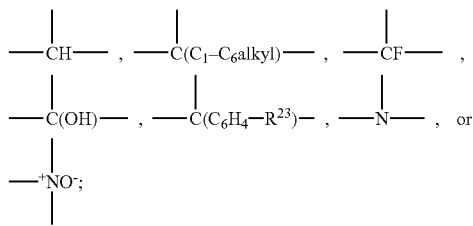

$R^{13}$ and $R^{14}$ are independently selected from the group consisting of —CH$_2$—, —CH(C$_1$-C$_6$ alkyl)-, —C(di-(C$_1$-C$_6$)alkyl), —CH═CH— and —O(C$_1$-C$_6$ alkyl)═CH—; or $R^{12}$ together with an adjacent $R^{13}$, or $R^{12}$ together with an adjacent $R^{14}$, form a —CH═CH— or a —CH═C(C$_1$-C$_6$ alkyl)- group;

a and b are independently 0, 1, 2 or 3, provided both are not zero; provided that when $R^{13}$ is —CH═CH— or —C(C$_1$-C$_6$ alkyl)═CH—, a is 1; provided that when $R^{14}$ is —CH═CH— or —C(C$_1$-C$_6$ alkyl)═CH—, b is 1; provided that when a is 2 or 3, the $R^{13}$'s can be the same or different; and provided that when b is 2 or 3, the $R^{14}$'s can be the same or different;

$R^{10}$ and $R^{11}$ are independently selected from the group consisting of 1-3 substituents independently selected from the group consisting of (C$_1$-C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$-C$_6$ alkylene)-COOR$^{19}$, —CH═CH—COOR$^{19}$, —CF$_3$, —CN, —NO$_2$ and halogen;

Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, (C$_1$-C$_6$)alkyl, aryl and aryl-substituted (C$_1$-C$_6$)alkyl;

$R^{21}$ is (C$_1$-C$_6$)alkyl, aryl or $R^{24}$-substituted aryl;

$R^{22}$ is H, (C$_1$-C$_6$)alkyl, aryl (C$_1$-C$_6$)alkyl, —C(O)R$^{19}$ or —COOR$^{19}$;

$R^{23}$ and $R^{24}$ are independently 1-3 groups independently selected from the group consisting of H, (C$_1$-C$_6$)alkyl, (C$_1$-C$_6$)alkoxy, —COOH, NO$_2$, —NR$^{19}$R$^{20}$, —OH and halogeno; and $R^{25}$ is H, —OH or (C$_1$-C$_6$)alkoxy.

11. The method of claim 10, wherein the at least one sterol absorption inhibitor is represented by Formula (X):

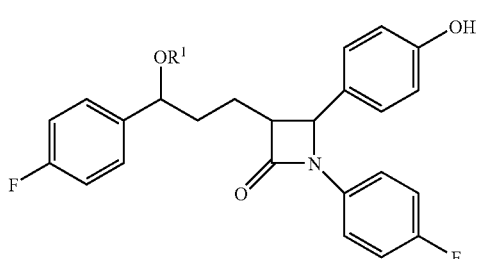

or isomers thereof, or pharmaceutically acceptable salts or solvates of the compounds of Formula (X) or of the isomers thereof, or prodrugs of the compounds of Formula (X) or of the isomers, salts or solvates thereof.

12. The method of claim 10, wherein the at least one sterol absorption inhibitor is represented by Formula (XI):

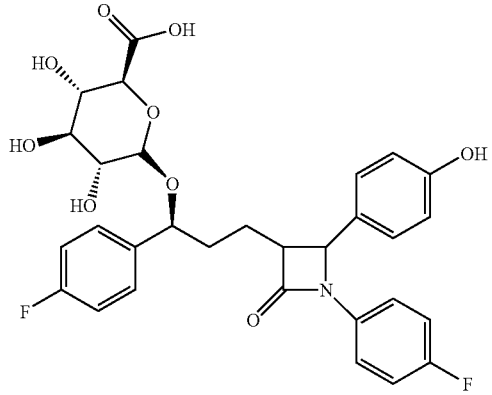

or isomers thereof, or pharmaceutically acceptable salts or solvates of the compounds of Formula (XI) or of the isomers thereof, or prodrugs of the compounds of Formula (XI) or of the isomers, salts or solvates thereof.

13. The method according to claim 1, wherein the sterol absorption inhibitor is administered to the mammal in an amount ranging from about 0.1 to about 30 milligrams of sterol absorption inhibitor per kilogram of mammal body weight per day.

14. The method according to claim 13, wherein the sterol absorption inhibitor is administered to the mammal in an amount ranging from about 0.1 to about 15 milligrams of sterol absorption inhibitor per kilogram of mammal body weight per day.

15. The method of claim 1, further comprising administering to the mammal in need of such treatment an effective amount of at least one lipid lowering agent in combination with the at least one sterol absorption inhibitor.

16. The method of claim 15, wherein the lipid lowering agent is a HMG-CoA reductase inhibitor.

17. The method of claim 16, wherein the HMG-CoA reductase inhibitor is selected from the group consisting of simvastatin, lovastatin, pravastatin, fluvastatin, atorvastatin, rosuvastatin, itavastatin and mixtures thereof.

18. The method of claim 17, wherein the HMG-CoA reductase inhibitor is simvastatin or atorvastatin.

19. The method of claim 15, wherein the sterol absorption inhibitor is administered to the mammal in an amount ranging from about 0.1 to about 30 milligrams of sterol absorption inhibitor per kilogram of mammal body weight per day.

20. The method of claim 15, wherein the lipid lowering agent is administered to the mammal in an amount ranging from about 0.1 to about 80 milligrams of lipid lowering agent per kilogram of mammal body weight per day.

21. The method of claim 15, wherein the sterol absorption inhibitor and lipid lowering agent are present in separate treatment compositions.

22. The method of claim 15, comprising:
a) a sterol absorption inhibitor represented by Formula (VIII):

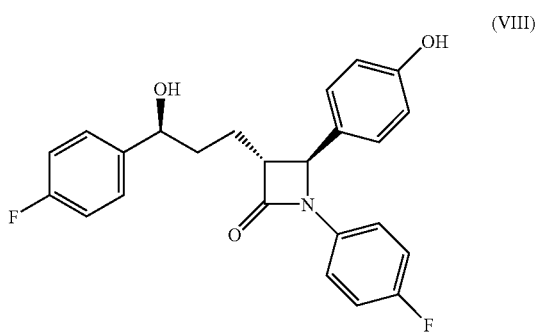

and
b) at least one HMG-CoA reductase inhibitor.

23. The method of claim 22, wherein the HMG-CoA reductase inhibitor is selected from the group consisting of lovastatin, pravastatin, fluvastatin, simvastatin, atorvastatin, rosuvastatin, itavastatin and mixtures thereof.

24. A method of treating sitosterolemia comprising administering to a mammal in need of such treatment:
(a) an effective amount of a sterol absorption inhibitor represented by Formula (VIII):

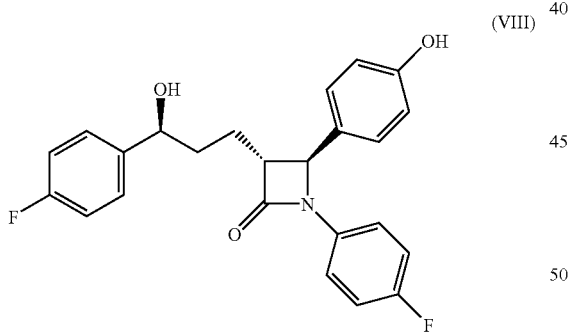

and
b) an effective amount of atorvastatin and/or simvastatin.

25. A pharmaceutical composition for the treatment or prevention of sitosterolemia, comprising an effective amount of the sterol absorption inhibitor used in the method of claim 1 in a pharmaceutically acceptable carrier.

26. A pharmaceutical composition for the treatment or prevention of sitosterolemia, comprising an effective amount of the sterol absorption inhibitor used in the method of claim 8 in a pharmaceutically acceptable carrier.

27. A pharmaceutical composition for the treatment or prevention of sitosterolemia, comprising an effective amount of the compound of Formula (VIII)

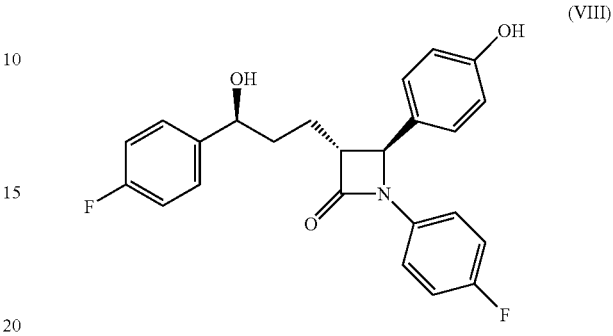

in a pharmaceutically acceptable carrier.

28. A pharmaceutical composition for the treatment or prevention of sitosterolemia, comprising:
a) an effective amount of the compound of Formula (VIII)

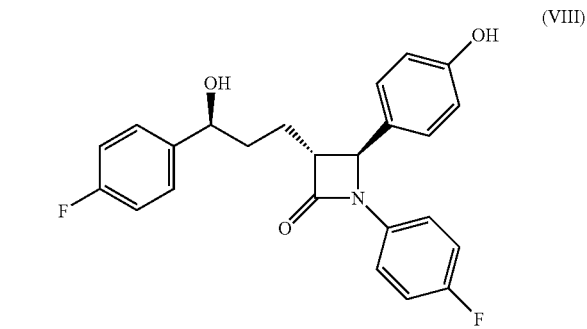

and
b) an effective amount of a lipid lowering agent in a pharmaceutically acceptable carrier.

29. The composition of claim 28, wherein the lipid lowering agent is a HMG-CoA reductase inhibitor.

30. The composition of claim 29, wherein the HMG-CoA reductase inhibitor is selected from the group consisting of lovastatin, pravastatin, fluvastatin, simvastatin, atorvastatin, rosuvastatin, itavastatin and mixtures thereof.

31. The composition of claim 30, wherein the HMG-CoA reductase inhibitor is simvastatin or atorvastatin.

32. A method of treating sitosterolemia, comprising administering to a mammal in need of such treatment: (1) an effective amount of at least one sterol absorption inhibitor, or pharmaceutically acceptable salt or solvate of the least one sterol absorption inhibitor, or prodrug of the least one sterol absorption inhibitor or pharmaceutically acceptable salt or solvate of the least one sterol absorption, or mixture thereof; and (2) an effective amount of at least one bile acid sequestrant or other lipid lowering agent.

33. A method of treating sitosterolemia comprising administering to a mammal in need of such treatment: (1) an effective amount of at least one sterol absorption inhibitor, or pharmaceutically acceptable salt or solvate of the least one sterol absorption inhibitor, or prod rug of the least one sterol absorption or pharmaceutically acceptable salt or solvate of the least one sterol absorption inhibitor, or mixture thereof; and (2) at least one sterol biosynthesis inhibitor.

34. A method of reducing plasma or tissue concentration of at least one non-cholesterol sterol, 5α-stanol, or mixture thereof, comprising administering to a mammal in need of such treatment an effective amount of at least one treatment composition comprising an effective amount of at least one sterol absorption inhibitor or at least one stanol absorption inhibitor, or pharmaceutically acceptable salt or solvate of the least one sterol absorption inhibitor or the at least one stanol absorption inhibitor, or prodrug of the least one sterol absorption inhibitor or the at least one stanol absorption inhibitor or pharmaceutically acceptable salt or solvate of the least one sterol absorption inhibitor or the at least one stanol absorption inhibitor, or mixture thereof.

35. The method according to claim 34, wherein the non-cholesterol sterol is at least one phytosterol.

36. The method according to claim 35, wherein the phytosterol is selected from the group consisting of sitosterol, campesterol, stigmasterol, avenosterol, and mixtures thereof.

37. The method according to claim 36, wherein the phytosterol is selected from the group consisting of sitosterol and campesterol.

38. The method according to claim 34, wherein the 5α-stanol is selected from the group consisting of cholestanol, 5α-campestanol, 5α-sitostanol and mixtures thereof.

39. A method of reducing plasma or tissue concentration of at least one non-cholesterol sterol, 5α-stanol, or mixture thereof, comprising administering to a sitosterolemic mammal in need of such treatment an effective amount of at least one treatment composition comprising an effective amount of at least one sterol absorption inhibitor or at least one stanol absorption inhibitor, or pharmaceutically acceptable salt or solvate of the least one sterol absorption inhibitor or the at least one stanol absorption inhibitor, or prodrug of the least one sterol absorption inhibitor or the at least one stanol absorption inhibitor or pharmaceutically acceptable salt or solvate of the least one sterol absorption inhibitor or the at least one stanol absorption inhibitor, or mixture thereof.

40. The method of 39, wherein the sterol absorption inhibitor is represented by Formula (VIII)

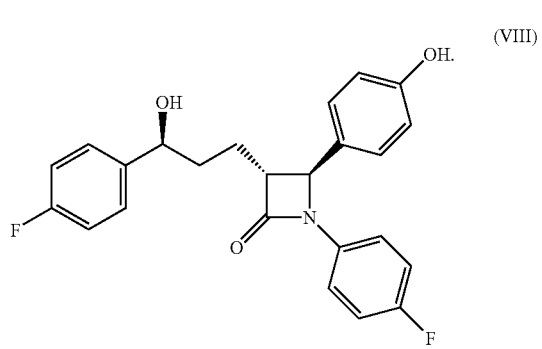

(VIII)

41. The method of claim 40, wherein the treatment composition further comprises at least one lipid lowering agent which is an HMG-CoA reductase inhibitor.

42. The method of claim 41, wherein the HMG-CoA reductase inhibitor is simvastatin or atorvastatin.

43. The method of claim 39, further comprising administering to the mammal in need of such treatment an effective amount of at least one bile acid sequestrant in combination with at least one of the sterol absorption inhibitors.

44. The method of claim 39, wherein the sterol absorption inhibitor is represented by Formula (VIII)

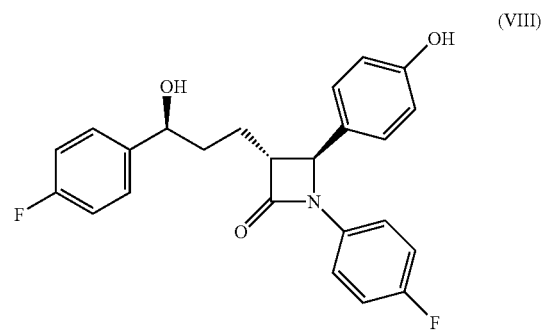

(VIII)

and the treatment composition further comprises at least one bile acid sequestrant.

45. The method of claim 44, wherein the bile acid sequestrant is selected from the group consisting of cholestyramine, colesevelam hydrochloride, and colestipol.

46. A pharmaceutical composition for the treatment or prevention of sitosterolemia, comprising:

a) an effective amount of the compound of Formula (VIII)

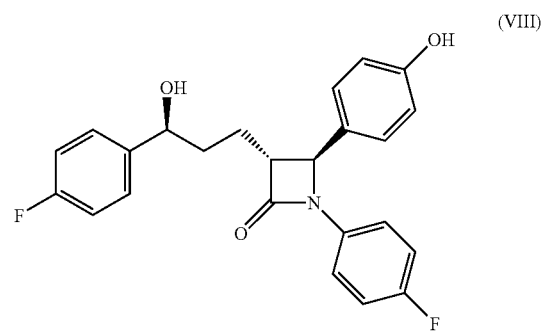

(VIII)

and b) an effective amount of a bile acid sequestrant in a pharmaceutically acceptable carrier.

47. The composition of claim 46, wherein the bile acid sequestrant is selected from the group consisting of cholestyramine, colesevelam hydrochloride, and colestipol.

48. A method of reducing plasma or tissue concentration of at least one compound selected from the group consisting of phytosterols, 5α-stanols and mixtures thereof, comprising administering to a sitosterolemic mammal in need of such treatment an effective amount of at least one sterol absorption inhibitor or a prodrug or a pharmaceutically acceptable salt thereof.

49. A method of reducing plasma or tissue concentration of at least one compound selected from the group consisting of phytosterols, 5α-stanols and mixtures thereof, comprising administering to a mammal in need of such treatment an effective amount of at least one sterol absorption inhibitor or a prodrug or a pharmaceutically acceptable salt thereof and at least one lipid lowering agent.

50. A method of reducing plasma or tissue concentration of at least one compound selected from the group consisting of phytosterols, 5α-stanols and mixtures thereof, comprising administering to a sitosterolemic mammal in need of such treatment an effective amount of at least one sterol absorption inhibitor or a prodrug or a pharmaceutically acceptable salt thereof and at least one lipid lowering agent.

51. A method of reducing plasma or tissue concentration of at least one compound selected from the group consisting of phytosterols, 5α-stanols and mixtures thereof, comprising administering to a mammal in need of such treatment an effective amount of at least one sterol absorption inhibitor or a prodrug or a pharmaceutically acceptable salt thereof and at least one bile acid sequestrant.

52. A therapeutic combination comprising:

a) a first amount of the compound of Formula (VIII)

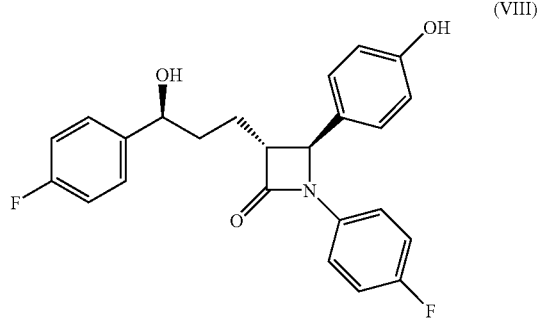

and b) a second amount of a lipid lowering agent, wherein the first amount and the second amount together comprise a therapeutically effective amount for the treatment or prevention of sitosterolemia in a mammal.

53. A therapeutic combination comprising:

a) a first amount of the compound of Formula (VIII)

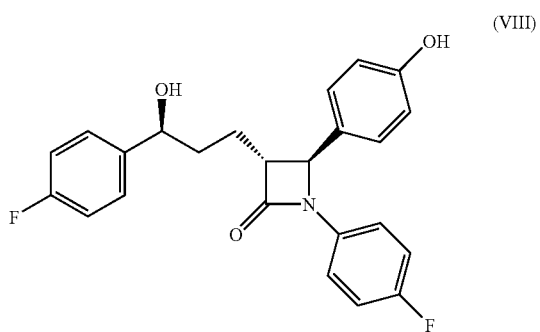

and b) a second amount of a bile acid sequestrant, wherein the first amount and the second amount together comprise a therapeutically effective amount for the treatment or prevention of sitosterolemia in a mammal.

* * * * *

UNITED STATES PATENT AND TRADEMARK OFFICE
CERTIFICATE OF CORRECTION

PATENT NO. : 7,417,039 B2  Page 1 of 1
APPLICATION NO. : 10/057629
DATED : August 26, 2008
INVENTOR(S) : Harry R. Davis It is certified that error appears in the above-identified patent and that said Letters Patent is hereby corrected as shown below:

In the Claims:

| | |
|---|---|
| Col. 58, line 65 | Please correct "nyla koxy" to -- nylalkoxy -- |
| Col. 58, line 66 | Please correct "alkanediol" to -- alkanedioyl -- |
| Col. 59, line 3 | Please correct "-ON,-" to -- CN, -- |
| Col. 59, line 64 | Please correct "benzod ioxolyl" to -- benzodioxolyl -- |
| Col. 62, line 8 | Please correct "losthiazolyl" to -- iosthiazolyl -- |
| Col. 62, line 44 | Please correct "off" to -- of f -- |
| Col. 64, line 33 | Please correct "-OH$_2$-" to -- -CH$_2$- -- |
| Col. 66, line 45 | Please correct "-O(O)-" to -- -C(O)- -- |
| Col. 71, line 2 | Please correct "prod rug" to -- prodrug -- |
| Col. 71, line 40 | Please correct "the least" to -- the at least -- |

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,417,039 B2 | Page 1 of 1 |
| APPLICATION NO. | : 10/057629 | |
| DATED | : August 26, 2008 | |
| INVENTOR(S) | : Davis | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 1159 days Delete the phrase "by 1159 days" and insert -- by 1259 days --

Signed and Sealed this

Thirtieth Day of March, 2010

David J. Kappos
*Director of the United States Patent and Trademark Office*